(12) United States Patent
Fisher, Jr. et al.

(10) Patent No.: US 12,409,260 B2
(45) Date of Patent: Sep. 9, 2025

(54) DEVICES AND METHODS FOR TREATING A CORONAVIRUS INFECTION AND SYMPTOMS THEREOF

(71) Applicant: Aethlon Medical, Inc., San Diego, CA (US)

(72) Inventors: Charles J. Fisher, Jr., Cardiff-by-the-Sea, CA (US); Rosalia De Necochea Campion, Oceanside, CA (US); Steven P. Larosa, South Hamilton, MA (US); Annette Marleau, San Diego, CA (US); Michael Jacobs, San Diego, CA (US)

(73) Assignee: Aethlon Medical, Inc., San Diego, CA (US)

(*) Notice: Subject to any disclaimer, the term of this patent is extended or adjusted under 35 U.S.C. 154(b) by 385 days.

(21) Appl. No.: 17/918,085

(22) PCT Filed: Apr. 8, 2021

(86) PCT No.: PCT/US2021/026377
§ 371 (c)(1),
(2) Date: Oct. 10, 2022

(87) PCT Pub. No.: WO2021/211351
PCT Pub. Date: Oct. 21, 2021

(65) Prior Publication Data
US 2023/0158222 A1  May 25, 2023

Related U.S. Application Data

(60) Provisional application No. 63/008,786, filed on Apr. 12, 2020.

(51) Int. Cl.
*A61M 1/34* (2006.01)
*A61M 1/36* (2006.01)

(52) U.S. Cl.
CPC ........ *A61M 1/3486* (2014.02); *A61M 1/3679* (2013.01); *A61M 2202/206* (2013.01)

(58) Field of Classification Search
CPC .............. A61M 1/3486; A61M 1/3679; A61M 2202/206
See application file for complete search history.

(56) References Cited

U.S. PATENT DOCUMENTS 6,692,908 B1 * 2/2004 Foung ................. C07K 16/109
 435/339
2002/0033181 A1 * 3/2002 Groth ..................... A61P 31/12
 604/4.01

(Continued)

FOREIGN PATENT DOCUMENTS

| WO | WO 2009/023332 | 2/2009 |
| WO | WO 2010/065765 | 6/2010 |
| WO | WO 2021/211351 | 10/2021 |

OTHER PUBLICATIONS

Wang, C. H., Liu, C. Y., Wan, Y. L., Chou, C. L., Huang, K. H., Lin, H. C., ... & Kuo, H. P. (2005). Persistence of lung inflammation and lung cytokines with high-resolution CT abnormalities during recovery from SARS. Respiratory research, 6, 1-12. (Year: 2005).*

(Continued)

*Primary Examiner* — Adam Marcetich
(74) *Attorney, Agent, or Firm* — Knobbe, Martens, Olson & Bear, LLC

(57) ABSTRACT

The devices and methods of the present invention can be used to capture and remove COVID-19 mediating nanoparticles and/or exosomes associated with COVID-19 or similar disease from the circulatory system of patients in need thereof, including those with post-COVID-19 syndrome or similar post-disease sequelae so-called "long haul" symptoms of COVID-19 or similar disease. The present invention benefits patients by providing lectin based extracorporeal (Continued)

methods for binding and physically removing SARS-CoV-2 virions, or fragments thereof, from the circulatory system. Also provided are lectin based extracorporeal methods of binding and physically removing non-viral COVID-19 mediating nanoparticles. Also disclosed herein are devices and methods for reducing the levels of biomarkers and markers of morbidity/mortality of diseases such as COVID-19 and similar diseases, including cytokines, such as IL-6, Troponin T, and D-dimer.

11 Claims, 20 Drawing Sheets

Specification includes a Sequence Listing.

(56) References Cited

U.S. PATENT DOCUMENTS

| | | | | |
|---|---|---|---|---|
| 2004/0062754 | A1* | 4/2004 | O'Brien | A61P 31/14 514/454 |
| 2005/0274672 | A1* | 12/2005 | Tu | B01D 61/145 210/645 |
| 2007/0248612 | A1* | 10/2007 | Wilson | A61K 35/16 435/339 |
| 2011/0218512 | A1* | 9/2011 | Tullis | A61K 38/13 604/500 |
| 2011/0284463 | A1* | 11/2011 | Tullis | A61M 1/3486 210/638 |
| 2012/0037564 | A1* | 2/2012 | Tullis | C12N 7/00 210/635 |
| 2012/0164628 | A1* | 6/2012 | Duffin | G01N 33/54366 435/5 |
| 2017/0333914 | A1* | 11/2017 | Kang | B03C 1/288 |
| 2020/0046953 | A1* | 2/2020 | Vase | A61B 5/031 |
| 2020/0325169 | A1* | 10/2020 | Sowemimo-Coker | A61M 1/3437 |
| 2022/0154170 | A1* | 5/2022 | Overbaugh | C07K 14/005 |
| 2022/0241399 | A1* | 8/2022 | Lusso | A61K 39/12 |

OTHER PUBLICATIONS

Lessler, J., Reich, N. G., Brookmeyer, R., Perl, T. M., Nelson, K. E., & Cummings, D. A. (2009). Incubation periods of acute respiratory viral infections: a systematic review. The Lancet infectious diseases, 9(5), 291-300. (Year: 2009).*

Odedra, A., Lalloo, D. G., Kennedy, G., Llewellyn, S., & McCarthy, J. S. (2019). Safety and effectiveness of apheresis in the treatment of infectious diseases: A systematic review. Journal of Infection, 79(6), 513-520. (Year: 2019).*

Yükselmiş, Girit S, Ça ğ, Özçetin M. A child with acute liver failure associated with influenza A and resolved with plasma exchange treatment. Hong Kong Journal of Emergency Medicine. 2018;25(5):281-285. doi: 10.1177/1024907918754441 (Year: 2018).*

Koch, Benjamin et al., "Lectin Affinity Plasmapheresis for Middle East Respiratory Syndrome-Coronavirus and Marburg Virus Glycoprotein Elimination" Blood Purif, 2018, pp. 126-133, vol. 46.

Ronco, Claudio et al., "Coronavirus Epidemic and Extracorporeal Therapies in Intensive Care: si vis pacem para bellum" Blood Purif, 2020, pp. 255-258, vol. 49.

International Search Report for PCT/US2021/026377 dated Sep. 23, 2021.

Grassmann et al., "A circulating microRNA profile is associated with late-stage newvascular age-related macular degeneration", Plos One, vol. 9(9):1-8, retreived from the internet at https://journals.plos.org/plosone/article?id=10.1371/journal.pone.0107461 (2014).

Liu et al., "Tumour-suppressive microRNA-424-5p directly targets CCNE1 as potential prognostic markers in epithelial ovarian cancer", Cell Cycle, vol. 17(3):309-318 (2018).

Sabine et al., "Associations of circulating plasma microRNAs with age, body mas index and sex in a population-based study", BMC Medical Genomics, Biomed Central Ltd., London, UK, vol. 8(61):1-9 (2015).

Zhan-Peng et al., "MicroRNA expression profiling in exosomes derived from gastric cancer stem-like cells", Oncotarget, vol. 8(55):93839-93855, retreived from https://pmc.ncbi.nlm/nih.gov/articles/PMC5706839 (2017).

Zhang et al., "Serum microRNA panel for early diagnosis of the onset of hepatocellular carcinoma", Medicine, vol. 96(2):1-8 (2017).

Extended European Search Report in application No. 21788894.0, dated Oct. 28, 2024, in 13 pages.

Buttner et al., "Extracorporeal virus elimination for the treatment of severe Ebola virus disease—First experience with lectin affinity plasmapheresis", Blood Purification, vol. 38(3-4):286-291 (2015).

International Preliminary Report on Patentability and Written Opinion in application No. PCT/US2021/26377, mailed on Oct. 13, 2022, in 8 pages.

Extended European Search Report in application No. 21788894.0, dated Mar. 25, 2024, in 15 pages.

* cited by examiner

Pre-treatment

| T = 0 | Mean | Mode |
|---|---|---|
| Day 1 | 101 ±5 | 93 ±3 |
| Day 2 | 94 ±2 | 84 ±2 |
| Day 3 | 92 ±2 | 78 ±4 |
| Day 4 | 102 ±2 | 86 ±9 |

Post-treatment

| T = 0 | Mean | Mode |
|---|---|---|
| Day 1 | 83 ±2 | 69 ±3 |
| Day 2 | 99 ±5 | 83 ±4 |
| Day 3 | 97 ±4 | 87 ±5 |
| Day 4 | 95 ±2 | 76 ±5 |

FIG. 7B cont.

SEQUENCE LISTING

<160> NUMBER OF SEQ ID NOS: 3

<210> SEQ ID NO 1
<211> LENGTH: 22
<212> TYPE: RNA
<213> ORGANISM: Homo sapiens

<400> SEQUENCE: 1
cagcagcaau ucauguuuug aa                                                   22

<210> SEQ ID NO 2
<211> LENGTH: 22
<212> TYPE: RNA
<213> ORGANISM: Homo sapiens

<400> SEQUENCE: 2
ccaauauuac ugugcugcuu ua                                                   22

<210> SEQ ID NO 3
<211> LENGTH: 22
<212> TYPE: RNA
<213> ORGANISM: Caenorhabditis elegans

<400> SEQUENCE: 3
ucaccgggug uaaaucagcu ug                                                   22

DEVICES AND METHODS FOR TREATING A CORONAVIRUS INFECTION AND SYMPTOMS THEREOF

CROSS-REFERENCE TO RELATED APPLICATIONS

This application is a U.S. National Phase Application of PCT International Application Number PCT/US2021/026377, filed on Apr. 8, 2021, designating the United States of America and published in the English language, which is an International Application of and claims the benefit of priority to U.S. Provisional Application No. 63/008,786, filed on Apr. 12, 2020. The disclosures of the above-referenced applications are hereby expressly incorporated by reference in their entireties.

REFERENCE TO SEQUENCE LISTING

The present application is being filed along with a Sequence Listing in electronic format. The Sequence Listing is provided in a file entitled SeqList-AETH-034NP, which was created on Oct. 10, 2022 and is 736 bytes in size. The information in the electronic Sequence Listing is hereby expressly incorporated by reference in its entirety.

FIELD

The present invention is related to the field of therapeutic methodologies and devices for treating or inhibiting viral infections including coronavirus infections, beta coronavirus infections, or COVID-19 infections, including COVID-19 variant infections, and sequela associated with said infections.

BACKGROUND

The 2019-20 coronavirus pandemic is an ongoing pandemic of coronavirus disease 2019 (COVID-19), caused by severe acute respiratory syndrome coronavirus 2 (SARS-CoV-2). The SARS-CoV-2 virus is mainly spread during close contact and by small droplets produced when the infected cough, sneeze, or talk. People may also become infected by touching a contaminated surface and then their face. The virus can survive on surfaces for up to 72 hours. It is most contagious during the first three days after onset of symptoms, although spread may be possible before symptoms appear and in later stages of the disease. Common symptoms include fever, cough, and shortness of breath. Complications may include pneumonia, acute respiratory distress syndrome, cardiac complications, neurological complications, septic shock, and death. Vaccines have only recently been approved. The emergence of many SARS-CoV-2 variants has led to concerns regarding the efficacy of current vaccines.

The COVID-19 pandemic has led to significant loss of human life. Approximately 15-20% of patients develop severe respiratory distress syndrome or septic shock. The treatment of these critically ill patients is particularly difficult, requiring sedation, supplemental oxygen, and life support ventilators. Furthermore, some patients exhibit persistent symptoms even after clearance of the virus. These so-called "long hauler" patients with post-COVID-19 syndrome are reported to have debilitating sequela including those affecting the pulmonary, cardiac, and neurological systems. Morbidity and mortality associated with COVID-19 are highest in the elderly and among people with comorbidities.

Accordingly, there is an urgent need for therapeutic interventions, particularly for patients critically ill with or at severe risk for advanced COVID-19 disease.

SUMMARY

Aspects of the present invention described herein include devices and methods for the capture and removal of coronavirus, beta coronavirus, or COVID-19 viral particles, including COVID-19 variant viral particles, or subcellular nanoparticles related thereto, e.g., exosomes, or both from the circulatory system of a subject, which is or has been infected with such virus or that presents sequela resulting from such infections or both, even when circulating virus in said subject is diminished, as compared to the initial infection of said subject, or absent altogether. These subcellular nanoparticles may include viral particles or components thereof, or other molecules such as cytokines, chemokines, or miRNAs that cause or are associated with a coronavirus infection or a symptom or sequela thereof such as a coagulation disorder or hypoxia. Some of the alternatives set forth herein directly benefit COVID-19 patients, which have either an on-going infection or after clearance of the infection, by providing lectin based extracorporeal methods, which bind and physically remove the subcellular nanoparticles, such as exosomes, or viral particles or both, from the patient's blood thereby treating or inhibiting the COVID-19 infection or a symptom or sequela thereof. Some alternatives described herein provide lectin based extracorporeal methods for binding and physically removing non-viral COVID-19 mediating nanoparticles, such as exosomes, from the circulatory system, thereby reducing exosome mediated COVID-19 infection or sequelae thereof and improving the levels or amounts of total lymphocyte count or to reduce the disease severity or the onset of lymphopenia. For patients severely affected by or at high risk for severe COVID-19 disease due to a SARS-CoV infection, the devices and methods described herein can be used to reduce time spent on mechanical ventilators, reduce the likelihood of cardiac complications or blood clotting, reduce the likelihood of multiorgan failure, reduce the likelihood of acute kidney disease, sepsis and/or other complications. Additional embodiments concern more generally the use of one or more of the lectin based extracorporeal methods, which bind and physically remove the subcellular nanoparticles, such as exosomes, or viral particles or both, from a patient's blood to treat, inhibit, reduce or improve a coagulopathy or hypoxia in said patient, preferably but not necessarily a patient that is infected or has been infected with virus e.g., COVID-19. Coagulopathy is a condition in which the coagulation system is activated and fibrin forms within blood vessels. This condition can cause impaired blood flow and oxygenation of tissues.

Aspects of the methods described herein can be used to inhibit onset of a coagulopathy, such as a COVID-19 associated coagulopathy, or the amount or level of a marker thereof, such as the amount or level of D-dimer, C-reactive protein, and/or T-Troponin. For example, for severely affected COVID-19 patients having systemic inflammation and/or compounds that contribute to coagulopathy, the devices and methods described herein can be used to suppress or reduce the production or presence of circulating chemokines and/or cytokines such as IL-1, IL-6, IL-10, IL-15, CXCL10, CCL2, Myeloperoxidase, VCAM-1, TNF alpha, C-reactive protein (CRP), D-dimer, or Troponin-T or any combination thereof. Optionally, a measure of the levels or amounts of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a sample of plasma or blood of the patient is made before the lectin based extracorporeal method is performed and after the lectin based extracorporeal method is completed (e.g., at 4 days or more after therapy).

The present invention also relates to methods for using lectins (e.g., *Galanthus nivalis* agglutinin (GNA), *Narcissus pseudonarcissus* agglutinin (NPA) or *Nostoc ellipsosporum* cyanovirin (referred herein as cyanovirin)) that bind to coronavirus, beta coronavirus, or COVID-19 viral particles, including COVID-19 variant viral particles, or subcellular nanoparticles related thereto, e.g., exosomes, or both, in particular SARS-CoV-2 virions, or fragments thereof, and non-viral subcellular nanoparticles, such as exosomes, related thereto to remove them from infected blood or plasma in an extracorporeal setting. Accordingly, some alternatives provide a method for treating or inhibiting a coronavirus infection, or a symptom or sequela thereof, in an individual comprising obtaining blood or plasma from the individual, passing the blood or plasma through a filter membrane, preferably a porous hollow fiber membrane, wherein lectin molecules (e.g., *Galanthus nivalis* agglutinin (GNA), *Narcissus pseudonarcissus* agglutinin (NPA) or *Nostoc ellipsosporum* cyanovirin) are immobilized within the exterior portion of the membrane, preferably at a porous portion of the membrane, thereby collecting pass-through blood or plasma or both and reinfusing the pass-through blood or plasma or both into the individual.

Passage of the blood through the hollow fibers having immobilized lectin, for example, causes the SARS-CoV-2 virions and fragments thereof and non-viral subcellular nanoparticles, such as exosomes, which contain glycoproteins, to bind to the lectins thereby reducing the viral load and the amount of non-viral subcellular nanoparticles, such as exosomes, in the effluent. In some embodiments, lectins that bind viral envelope proteins e.g., the spike protein, of many subtypes, variants, or mutants of coronavirus are employed in the devices described herein. The methods described herein effectively reduce the number of SARS-CoV-2 virions and fragments thereof and non-viral subcellular nanoparticles, such as exosomes, in the blood and rapidly allow a patient to recover from the infection or symptom or sequela thereof.

Thus, an object of the invention is to provide a method for reducing the COVID-19 viral load in the blood of an individual infected with COVID-19. In one embodiment, COVID-19 virions or protein fragments thereof or combinations thereof are removed from the blood of an individual infected with the virus. Optionally, a measure of viral exposure or the level of circulating virus in the individual (e.g., as detected in blood or plasma) is made such as, measuring the SARS CoV-2 RNA levels in plasma and nasopharyngeal samples (e.g., isolated from a nasal swab) from the patient are detected e.g., before each lectin based extracorporeal method is performed, every 2 hours during therapy and/or after the therapy is completed.

Another object of the present invention is to provide a method for reducing the COVID-19 viral load or the amount of subcellular nanoparticles, such as exosomes, or both in the blood or plasma of a patient that is or has been infected with COVID-19 by extracorporeal circulation of the patient's blood through a cartridge comprising hollow fibers containing immobilized lectins (e.g., *Galanthus nivalis* agglutinin (GNA), *Narcissus pseudonarcissus* agglutinin (NPA) or *Nostoc ellipsosporum* cyanovirin) having affinity for viral COVID-19 glycoproteins or other subcellular nanoparticles, such as exosomes. Preferably, said patient is identified, diagnosed or selected as one having a COVID-19 infection or having had a COVID-19 infection prior to implementation of this method and, optionally, the viral load of COVID-19 or a marker of COVID-19 infection is measured in said subject, e.g., in a biological sample such as blood, nasal fluid, or saliva, prior to or after implementation of the method or both. In some embodiments, the patient receiving the method is selected as one having a diminished, reduced, or no amount of circulating COVID-19 viral particles in the blood or plasma, as compared to an initial infection, yet said patient presents sequela resulting from COVID-19 infection, e.g., a "long hauler" patient or a patient having sequela resulting from COVID-19 infection but no or a negligible amount of COVID-19 viral particles in the patient's plasma or blood.

Another object of the present invention is to provide a method for reducing the amount or level of IL-1, IL-6, IL-10, IL-15, CXCL10, CCL2, Myeloperoxidase, VCAM-1, TNF alpha, C-reactive protein (CRP), D-dimer, or Troponin-T or any combination thereof in the blood or plasma of a patient that is preferably infected with a virus or has been infected with a virus e.g., COVID-19 by extracorporeal circulation of the patient's blood through a cartridge comprising hollow fibers containing immobilized lectins (e.g., *Galanthus nivalis* agglutinin (GNA), *Narcissus pseudonarcissus* agglutinin (NPA) or *Nostoc ellipsosporum* cyanovirin) having affinity for viral COVID-19 glycoproteins or other subcellular nanoparticles, such as exosomes. Preferably, said patient is identified, diagnosed or selected as one having a COVID-19 infection or having had a COVID-19 infection prior to implementation of this method and, optionally, the viral load of COVID-19 or a marker of COVID-19 infection, or the levels or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof is measured in said subject e.g., in a biological sample such as blood, nasal fluid (e.g., isolated from a nasal swab), or saliva, prior to or after implementation of the method or both. In some embodiments, the patient receiving the method is selected as one having a diminished, reduced, or no amount of circulating COVID-19 viral particles in the blood or plasma, as compared to an initial infection, yet said patient presents sequela resulting from COVID-19 infection, e.g., a "long hauler" patient or a patient having sequela resulting from COVID-19 infection but no amount or a negligible amount of COVID-19 viral particles in the patient's plasma or blood.

Another object of the present invention is to provide a method for reducing the biomarker D-dimer in the blood or plasma of a patient, preferably but not necessarily a patient that is or has been infected with a virus e.g., COVID-19 by extracorporeal circulation of the patient's blood through a cartridge comprising hollow fibers containing immobilized lectins (e.g., *Galanthus nivalis* agglutinin (GNA), *Narcissus pseudonarcissus* agglutinin (NPA) or *Nostoc ellipsosporum* cyanovirin) having affinity for viral COVID-19 glycoproteins or other subcellular nanoparticles, such as exosomes. Preferably, said patient is identified, diagnosed or selected as one having a COVID-19 infection or having had a COVID-19 infection or being in need for a therapy, with elevated D-dimer levels (e.g., a patient having a coagulopathy or being at risk of having a coagulopathy) prior to implementation of this method and, optionally, the viral load of COVID-19 or a marker of COVID-19 infection, or IL-1, IL-6, IL-10, IL-15, CXCL10, CCL2, Myeloperoxidase, VCAM-1, TNF alpha, C-reactive protein (CRP), or Troponin-T levels, or any combination thereof is measured in said subject, e.g., in a biological sample such as blood, nasal fluid (e.g., an isolate from a nasal swab), or saliva, prior to or after implementation of the method or both. In some embodiments, the patient receiving the method is selected as one having a diminished, reduced, or no amount of circulating COVID-19 viral particles in the blood, as compared to an initial infection, yet said patient presents sequela resulting from COVID-19 infection, e.g., a "long hauler" patient or a patient having sequela resulting from COVID-19 infection but no or a negligible amount of COVID-19 viral particles in the patient's plasma or blood.

Another object of the present invention is to provide a method for reducing the biomarker Troponin T in the plasma or blood of a patient that is preferably but not necessarily infected with a virus or has been infected with a virus e.g., COVID-19 by extracorporeal circulation of the patient's blood through a cartridge comprising hollow fibers containing immobilized lectins (e.g., *Galanthus nivalis* agglutinin (GNA), *Narcissus pseudonarcissus* agglutinin (NPA) or *Nostoc ellipsosporum* cyanovirin) having affinity for viral COVID-19 glycoproteins or other subcellular nanoparticles, such as exosomes. Preferably, said patient is identified, diagnosed or selected as one having a COVID-19 infection or having had a COVID-19 infection prior to implementation of this method and, optionally, the viral load of COVID-19 or a marker of COVID-19 infection, or the levels or amount of IL-1, IL-6, IL-10, IL-15, CXCL10, CCL2, Myeloperoxidase, VCAM-1, TNF alpha, C-reactive protein (CRP), or D-dimer or any combination thereof is measured in said subject, e.g., in a biological sample such as blood, nasal fluid (e.g., isolated from a nasal swab), or saliva, prior to or after implementation of the method or both. In some embodiments, the patient receiving the method is selected as one having a diminished, reduced, or no amount of circulating COVID-19 viral particles in the blood or plasma, as compared to an initial infection, yet said patient presents sequela resulting from COVID-19 infection, e.g., a "long hauler" patient or a patient having sequela resulting from COVID-19 infection but no or a negligible amount of COVID-19 viral particles in the patient's plasma or blood.

Another object of the present invention is to provide a method for reducing subcellular nanoparticles, such as exosomes, comprising miR-424-5p (miR-424), miR-16-2-3p (miR-16), or both in the plasma or blood of a patient that is, preferably infected with a virus or has been infected with virus e.g., COVID-19, by extracorporeal circulation of the patient's blood through a cartridge comprising hollow fibers containing immobilized lectins (e.g., *Galanthus nivalis* agglutinin (GNA), *Narcissus pseudonarcissus* agglutinin (NPA) or *Nostoc ellipsosporum* cyanovirin) having an affinity for subcellular nanoparticles, such as exosomes, in particular exosomes comprising miR-424, miR-16, or both. Preferably, said patient is identified, diagnosed or selected as one having a COVID-19 infection or having had a COVID-19 infection prior to implementation of this method and, optionally, the viral load of COVID-19 or a marker of COVID-19 infection, or the levels or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof or the amount of exosomes comprising miR-424, miR-16, or both, is measured in said subject, e.g., in a biological sample such as blood, nasal fluid (e.g., isolated from a nasal swab), or saliva, prior to or after implementation of the method or both. In some embodiments, the patient receiving the method is selected as one having a diminished, reduced, or no amount of circulating COVID-19 viral particles in the blood, as compared to an initial infection, yet said patient presents sequela resulting from COVID-19 infection, e.g., a "long hauler" patient or patient having sequela resulting from COVID-19 infection but no or a negligible amount of COVID-19 viral particles in the patient's plasma or blood.

Another object of the present invention is to provide an apparatus comprising hollow fibers, wherein the exterior surface of the fibers is in close proximity with immobilized lectins (e.g., *Galanthus nivalis* agglutinin (GNA), *Narcissus pseudonarcissus* agglutinin (NPA) or *Nostoc ellipsosporum* cyanovirin) for use in removing COVID-19 and/or non-viral glycoproteins or other subcellular nanoparticles from a subject.

Preferred aspects of the present invention are related to the following numbered alternatives:

1. A method for reducing SARS-CoV-2 virions, or portions thereof, in a COVID-19 patient in need thereof, comprising:
   a) introducing blood or plasma from a patient infected with COVID-19 into an extracorporeal device comprising a lectin that binds to SARS-CoV-2 virions, or portions thereof;
   b) contacting the blood or plasma from the patient with the lectin in the extracorporeal device for a time sufficient to allow the SARS-CoV-2 virions, or portions thereof, present in the blood or plasma, to bind to said lectin;
   c) reintroducing the blood or plasma obtained after (b) into said patient, wherein the blood or plasma obtained after (b) has a reduced amount of the SARS-CoV-2 virions, or portions thereof, as compared to the blood or plasma of said patient prior to (b); and
   d) optionally, detecting or identifying SARS-CoV-2 virions, or portions thereof, in a sample from said patient, such as a nasal (e.g., isolated from a nasal swab), blood, or plasma sample, prior to (a) or after (b) or both and/or, optionally selecting or identifying a patient having COVID-19 to receive a therapy that reduces SARS-CoV-2 virions, or fragments thereof.

2. A method for reducing COVID-19 mediating nanoparticles in a COVID-19 patient in need thereof, comprising:
   a) introducing blood or plasma from a patient infected with COVID-19 into an extracorporeal device comprising a lectin that binds to COVID-19 mediating nanoparticles;
   b) contacting the blood or plasma from the patient with the lectin in the extracorporeal device for a time sufficient to allow the COVID-19 mediating nanoparticles to bind to said lectin;
   c) reintroducing the blood or plasma obtained after (b) into said patient, wherein the blood or plasma obtained after (b) has a reduced amount of the COVID-19 mediating nanoparticles, as compared to the blood or plasma of said patient prior to (b); and
   d) optionally, detecting or identifying SARS-CoV-2 virions, or portions thereof, or COVID-19 mediating nanoparticles in a sample from said patient, such as a nasal (e.g., isolated from a nasal swab), blood, or plasma sample, prior to (a) or after (b) or both and/or, optionally selecting or identifying a patient having COVID-19 to receive a therapy that reduces COVID-19 mediating nanoparticles.

3. A method for reducing exosomes comprising a COVID-19 antigen in a COVID-19 patient, comprising:
a) introducing blood or plasma from a patient infected with COVID-19 into an extracorporeal device comprising a lectin that binds to the exosomes comprising the COVID-19 antigen;
b) contacting the blood or plasma from the patient with the lectin in the extracorporeal device for a time sufficient to allow the exosomes comprising the COVID-19 antigen to bind to said lectin;
c) reintroducing the blood or plasma obtained after (b) into said patient, wherein the blood or plasma obtained after (b) has a reduced amount of the exosomes comprising the COVID-19 antigen, as compared to the blood or plasma of said patient prior to (b); and
d) optionally, detecting or identifying SARS-CoV-2 virions, or portions thereof or the exosomes comprising the COVID-19 antigen in a sample from said patient, such as a nasal (e.g., isolated from a nasal swab), blood, or plasma sample, prior to (a) or after (b) or both and/or, optionally selecting or identifying a patient having COVID-19 to receive a therapy that reduces exosomes comprising a COVID-19 antigen.

4. A method for reducing interleukin 6 (IL-6) in a COVID-19 patient comprising:
a) introducing blood or plasma from a patient infected with COVID-19 into an extracorporeal device comprising a lectin that binds to SARS-CoV-2 virions or fragments thereof or exosomes comprising a COVID-19 antigen;
b) contacting the blood or plasma from the patient with the lectin in the extracorporeal device for a time sufficient to allow the SARS-CoV-2 virions or fragments thereof or the exosomes comprising the COVID-19 antigen to bind to said lectin;
c) reintroducing the blood or plasma obtained after (b) into said patient, wherein the blood or plasma obtained after (b) has a reduced amount of the SARS-CoV-2 virions or fragments thereof, or the exosomes comprising the COVID-19 antigen, as compared to the blood or plasma of said patient prior to (b); and
d) optionally, measuring the level or amount of IL-6 in a sample from said patient, such as a blood or plasma sample, prior to (a) or after (b) or both and, optionally selecting or identifying a patient having COVID-19 to receive a therapy that reduces IL-6 levels.

5. A method for reducing the amount of circulating D-dimer in a COVID-19 patient comprising:
a) introducing blood or plasma from a patient infected with COVID-19 into an extracorporeal device comprising a lectin that binds to SARS-CoV-2 virions or fragments thereof or exosomes comprising a COVID-19 antigen;
b) contacting the blood or plasma from the patient with the lectin in the extracorporeal device for a time sufficient to allow the SARS-CoV-2 virions or fragments thereof or the exosomes comprising the COVID-19 antigen to bind to said lectin;
c) reintroducing the blood or plasma obtained after (b) into said patient, wherein the blood or plasma obtained after (b) has a reduced amount of the SARS-CoV-2 virions or fragments thereof or the exosomes comprising the COVID-19 antigen, as compared to the blood or plasma of said patient prior to (b); and
d) optionally, measuring the level or amount of D-dimer in a sample from said patient, such as a blood or plasma sample, prior to (a) or after (b) or both and, optionally selecting or identifying a patient having COVID-19 to receive a therapy that reduces D-dimer.

6. A method for reducing the amount of Troponin T in a COVID-19 patient comprising:
a) introducing blood or plasma from a patient infected with COVID-19 into an extracorporeal device comprising a lectin that binds to SARS-CoV-2 virions or fragments thereof or exosomes comprising a COVID-19 antigen;
b) contacting the blood or plasma from the patient with the lectin in the extracorporeal device for a time sufficient to allow the SARS-CoV-2 virions or fragments thereof or the exosomes comprising the COVID-19 antigen to bind to said lectin;
c) reintroducing the blood or plasma obtained after (b) into said patient, wherein the blood or plasma obtained after (b) has a reduced amount of the SARS-CoV-2 virions or fragments thereof or the exosomes comprising the COVID-19 antigen, as compared to the blood or plasma of said patient prior to (b); and
d) optionally, measuring the level or amount of Troponin T in a sample from said patient, such as a blood or plasma sample, prior to (a) or after (b) or both and, optionally selecting or identifying a patient having COVID-19 to receive a therapy that reduces Troponin T.

7. A method of treating or inhibiting a coronavirus infection e.g., a beta corona virus infection, or a symptom or sequela thereof, in a patient in need thereof, comprising:
a) introducing blood or plasma comprising coronavirus or a portion thereof from a patient having a coronavirus infection, or a symptom or sequela thereof, into an extracorporeal device comprising a lectin that binds to said coronavirus or a portion thereof;
b) contacting the blood or plasma from the patient with the lectin in the extracorporeal device for a time sufficient to allow the coronavirus or a portion thereof present in the blood or plasma, to bind to said lectin;
c) reintroducing the blood or plasma obtained after (b) into said patient, wherein the blood or plasma obtained after (b) has a reduced amount of the coronavirus, or portion thereof, as compared to the blood or plasma of said patient prior to (b); and
d) optionally, detecting or identifying the coronavirus or portions thereof in a sample from said patient, such as a nasal (e.g., isolated from a nasal swab), blood or plasma sample, prior to (a) or after (b) or both and/or, optionally selecting or identifying a patient having a coronavirus infection, or a symptom or sequela, thereof to receive a therapy that reduces said coronavirus or a portion thereof.

8. A method of treating or inhibiting a coronavirus infection e.g., a beta corona virus infection, or a symptom or sequela thereof, in a patient in need thereof, comprising:
a) introducing blood or plasma comprising exosomes associated with the coronavirus infection, or the symptom or sequela thereof, from a patient having a coronavirus infection, or a symptom or sequela thereof, into an extracorporeal device comprising a lectin that binds to said exosomes;
b) contacting the blood or plasma from the patient with the lectin in the extracorporeal device for a time sufficient to allow the exosomes present in the blood or plasma to bind to said lectin;

c) reintroducing the blood or plasma obtained after (b) into said patient, wherein the blood or plasma obtained after (b) has a reduced amount of the exosomes as compared to the blood or plasma of said patient prior to (b); and d) optionally, detecting or identifying the exosomes in a sample from said patient, such as a nasal, blood or plasma sample, prior to (a) or after (b) or both and/or, optionally selecting or identifying a patient having a coronavirus infection, or a symptom or sequela thereof, to receive a therapy that reduces said exosomes.

9. A method of treating or inhibiting a coronavirus infection e.g., a beta corona virus infection, or a symptom or sequela thereof, in a patient in need thereof, wherein the symptom or sequela thereof comprises COVID-19-associated coagulopathy (CAC), comprising:

a) introducing blood or plasma comprising exosomes associated with CAC from a patient having CAC into an extracorporeal device comprising a lectin that binds to said exosomes;

b) contacting the blood or plasma from the patient with the lectin in the extracorporeal device for a time sufficient to allow the exosomes present in the blood or plasma to bind to said lectin;

c) reintroducing the blood or plasma obtained after (b) into said patient, wherein the blood or plasma obtained after (b) has a reduced amount of the exosomes as compared to the blood or plasma of said patient prior to (b); and d) optionally, detecting or identifying the exosomes in a sample from said patient, such as a nasal, blood or plasma sample, prior to (a) or after (b) or both and/or, optionally selecting or identifying a patient having CAC to receive a therapy that reduces said exosomes.

10. The method of any one of alternatives 1-9, wherein the patient does not comprise a coronavirus infection prior to step (a) but exhibits symptoms or sequela of the coronavirus infection.

11. The method of any one of alternatives 1-9, wherein the patient has cleared the coronavirus infection prior to step (a), but the patient still exhibits symptoms or sequela of the coronavirus infection.

12. The method of any one of alternatives 1-11, wherein the blood or plasma of the patient does not comprise the coronavirus prior to step (a), but the patient still exhibits symptoms or sequela of the coronavirus infection.

13. The method of any one of alternatives 1-12, further comprising determining whether the patient has early acute lung injury (ALI), early acute respiratory distress syndrome (ARDS), dyspnea, respiratory frequency ≥30 breaths/min, blood oxygen saturation ≤93%, partial pressure of arterial oxygen to fraction of inspired oxygen ratio of <300, lung infiltrates >50%, respiratory failure within 24 to 48 hours, elevated ferritin, elevated lactate, elevated lactate dehydrogenase (LDH), low absolute lymphocyte count (ALC), low platelet count, elevated prothrombin time/international normalized ratio (PT/INR), septic shock, or multiple organ dysfunction or failure, or any combination thereof prior to (a) or after (b) or both.

14. The method of any one of alternatives 1-12, further comprising determining whether the patient has an elevated IL-6 level or amount either before (a) or after (b) or both.

15. The method of alternative 13, wherein the elevated serum IL-6 level is greater than or equal to 2 pg/mL.

16. The method of any one of alternatives 1-15, further comprising determining whether the patient has an elevated D-dimer level or amount either before (a) or after (b) or both.

17. The method of alternative 16, wherein the elevated serum D-Dimer level is greater than or equal to 500 ng/mL.

18. The method of any one of alternatives 1-17, further comprising determining whether the patient has an elevated Troponin T level or amount either before (a) or after (b) or both.

19. The method of alternative 17, wherein the elevated serum Troponin T level is greater than or equal to 15 ng/L.

20. The method of any one of alternatives 1-19, wherein the lectin is *Galanthus nivalis* agglutinin (GNA).

21. The method of any one of alternatives 1-20, wherein the extracorporeal device comprises a hollow fiber cartridge comprising the lectin and wherein the blood or plasma flows through hollow fibers of the hollow fiber cartridge.

22. The method of alternative 21, wherein the hollow fibers of the hollow fiber cartridge comprise a pore size that excludes cellular components of the blood or plasma from contacting the lectin.

23. The method of alternative 22, wherein the pore size is 200 nm or about 200 nm.

24. The method of any one of alternatives 20-23, wherein the lectin is immobilized or adsorbed on to a solid support, and the hollow fiber cartridge comprises the lectin immobilized or adsorbed on the solid support.

25. The method of alternative 24, wherein the solid support comprises diatomaceous earth.

26. The method of any one of alternatives 1-25, further comprising isolating coronavirus virions, or portions thereof, bound to the lectin of the extracorporeal device.

27. The method of any one of alternatives 1-25, further comprising isolating exosomes associated with the coronavirus infection, or the symptom or sequela thereof, bound to the lectin of the extracorporeal device.

28. The method of alternative 27, further comprising determining the contents of the isolated exosomes.

29. The method of alternative 27 or 28, wherein the exosomes associated with the coronavirus infection, or the symptom or sequela thereof, comprise miR-424-5p, or miR-16-2-3p, or both.

30. The method of any one of alternatives 1-29, further comprising observing or measuring a reduction in number of coronavirus virions, or portions thereof; number of exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T, or any combination thereof, in a sample of the patient's blood taken after (b) relative to a sample of the patient's blood taken before (b).

31. The method of any one of alternatives 1-30, further comprising observing an improvement in the coronavirus infection, or the symptom or sequela thereof, in the patient following (b) or (c) or both.

32. The method of alternative 31, wherein observing the improvement in the coronavirus infection, or the symptom or sequela thereof, comprises determining an improvement in early ALI, early ARDS, respiratory frequency, blood oxygen saturation, partial pressure of arterial oxygen to fraction of inspired oxygen ratio, lung infiltrates, respiratory failure, ferritin, lactate, LDH, ALC, platelet count, PT/INR, septic shock, or multiple organ dysfunction or failure, or any combination thereof, in the patient.

33. The method of alternative 31 or 32, wherein observing the improvement in the coronavirus infection, or the symptom or sequela thereof, comprises observing a reduction in number of coronavirus virions, or portions thereof; exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T, or any combination thereof in the patient relative to before the treatment.

34. The method of any one of alternatives 7-33, wherein the coronavirus infection is caused by a coronavirus selected from SARS-CoV-2, SARS-CoV-1, MERS-CoV, HCoV-229E, HCoV-OC43, HCoV NL63, or HCoV-HKU1.

35. The method of alternative 34, wherein the SARS-CoV-2 is a SARS-CoV-2 variant.

36. The method of alternative 34, wherein the SARS-CoV-2 variant is selected from 20I/501Y.V1 (B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429).

37. The method of any one of alternatives 1-36, wherein the extracorporeal device is primed with an anticoagulant, preferably heparin, to prevent clotting of blood prior to (a).

38. The method of any one of alternatives 1-37, wherein the blood is flowed at a rate of about 50 to about 600 mL/min, preferably about 200 to about 400 mL/min, preferably about 200 to about 240 ml/min through said extracorporeal device.

39. The method of any one of alternatives 1-38, wherein reintroducing the blood back to the patient comprises flushing the extracorporeal device with saline.

40. The method of any one of alternatives 1-39, wherein the blood or plasma is contacted with the extracorporeal device for 0.1, 0.2, 0.3, 0.4, 0.5, 0.6, 0.7, 0.8, 0.9, 1, 2, 3, 4, 5, 6, 7, 8, 9, or 10 hours, or any amount of time within a range defined by any two of the aforementioned times.

41. The method of any one of alternatives 1-40, wherein steps (a), (b), (c), and optionally (d) is repeated every day for 1, 2, 3, 4, 5, 6, 7, 8, 9, 10, 11, 12, 13, 14, or 15 days.

42. An extracorporeal device comprising a lectin for use in the treatment of a coronavirus infection, or a symptom or sequela thereof, or to reduce the levels or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a patient in need thereof.

43. An extracorporeal device comprising a lectin for use in the treatment of COVID-19-associated coagulopathy in a patient in need thereof.

44. An extracorporeal device comprising a lectin for use in a method of treating a coronavirus infection, or a symptom or sequela thereof, in a patient in need thereof, the method comprising flowing blood from the patient through the extracorporeal device such that the blood comes in contact with the lectin, thereby resulting in processed blood; and reintroducing the processed blood back to the patient.

45. The extracorporeal device for use of any one of alternatives 42-44, wherein the lectin is *Galantus nivalis* agglutinin.

46. The extracorporeal device for use of any one of alternatives 42-45, wherein the extracorporeal device comprises a hollow fiber cartridge comprising the lectin, wherein the blood of the patient flows through hollow fibers of the hollow fiber cartridge.

47. The extracorporeal device for use of alternative 46, wherein the lectin is immobilized or adsorbed onto a solid support, and the hollow fiber cartridge comprises the lectin immobilized or adsorbed on the solid support.

48. The extracorporeal device for use of alternative 47, wherein the solid support is diatomaceous earth.

49. The extracorporeal device for use of any one of alternatives 42-48, wherein the lectin selectively binds to coronavirus virions, or portions thereof; exosomes associated with the coronavirus infection, or the symptoms or sequela thereof, or any combination thereof.

50. The extracorporeal device for use of any one of alternatives 42-49, wherein the coronavirus infection is caused by a coronavirus selected from SARS-CoV-2, SARS-CoV-1, MERS-CoV, HCoV-229E, HCoV-OC43, HCoV NL63, or HCoV-HKU1.

51. The extracorporeal device for use of alternative 50, wherein the SARS-CoV-2 is a SARS-CoV-2 variant.

52. The extracorporeal device for use of alternative 51, wherein the SARS-CoV-2 variant is selected from 20I/501Y.V1 (B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429).

53. The extracorporeal device for use of any one of alternatives 36-52, wherein the extracorporeal device is used for 0.1, 0.2, 0.3, 0.4, 0.5, 0.6, 0.7, 0.8, 0.9, 1, 2, 3, 4, 5, 6, 7, 8, 9, or 10 hours at a time, or any amount of time within a range defined by any two of the aforementioned times.

54. The extracorporeal device for use of any one of alternatives 36-53, wherein the extracorporeal device is used every day for 1, 2, 3, 4, 5, 6, 7, 8, 9, 10, 11, 12, 13, 14, or 15 days.

55. A method for reducing exosomes comprising miR-424-5p, or miR-16-2-3p, or both in a patient, preferably a patient having a coronavirus infection, such as COVID-19, or a patient that has had a coronavirus infection, such as COVID-19, comprising:
a) introducing blood or plasma from said patient into an extracorporeal device comprising a lectin that binds to the exosomes, e.g., GNA, NPA, or cyanovirin;
b) contacting the blood or plasma from the patient with the lectin in the extracorporeal device for a time sufficient to allow the exosomes to bind to said lectin;
c) reintroducing the blood or plasma obtained after (b) into said patient, wherein the blood or plasma obtained after (b) has a reduced amount of the exosomes, as compared to the blood or plasma of said patient prior to (b); and
d) optionally, detecting or identifying exosomes having miR-424-5p, or miR-16-2-3p, or both in a sample from said patient, such as a nasal (e.g., isolated from a nasal swab), blood, or plasma sample, prior to (a) or after (b) or both and/or, optionally selecting or identifying a patient having COVID-19 to receive a therapy that reduces exosomes comprising miR-424-5p, or miR-16-2-3p, or both.

56. The method of alternative 55, wherein the patient does not comprise a coronavirus infection, such as COVID-19, prior to step (a) but exhibits symptoms or sequela of the coronavirus infection.

57. The method of any one of alternatives 55 or 56, wherein the patient has cleared the coronavirus infection, such as COVID-19, prior to step (a), but the patient still exhibits symptoms or sequela of the coronavirus infection.

58. The method of any one of alternatives 55-57, wherein the blood or plasma of the patient does not comprise the coronavirus, such as COVID-19, prior to step (a), but the patient still exhibits symptoms or sequela of the coronavirus infection.

59. The method of any one of alternatives 55-58, further comprising determining whether the patient has early acute lung injury (ALI), early acute respiratory distress syndrome (ARDS), dyspnea, respiratory frequency ≥30 breaths/min, blood oxygen saturation ≤93%, partial pressure of arterial oxygen to fraction of inspired oxygen ratio of <300, lung infiltrates >50%, respiratory failure within 24 to 48 hours, elevated ferritin, elevated lactate, elevated lactate dehydrogenase (LDH), low absolute lymphocyte count (ALC), low platelet count, elevated prothrombin time/international normalized ratio (PT/INR), septic shock, or multiple organ dysfunction or failure, or any combination thereof prior to (a) or after (b) or both.

60. The method of any one of alternatives 55-59, further comprising determining whether the patient has an elevated IL-6 level or amount either before (a) or after (b) or both.

61. The method of alternative 60, wherein the elevated serum IL-6 level is greater than or equal to 2 pg/mL.

62. The method of any one of alternatives 55-61, further comprising determining whether the patient has an elevated D-dimer level or amount either before (a) or after (b) or both.

63. The method of alternative 62, wherein the elevated serum D-Dimer level is greater than or equal to 500 ng/mL.

64. The method of any one of alternatives 55-63, further comprising determining whether the patient has an elevated Troponin T level or amount either before (a) or after (b) or both.

65. The method of alternative 64, wherein the elevated serum Troponin T level is greater than or equal to 15 ng/L.

66. The method of any one of alternatives 55-65, wherein the lectin is *Galanthus nivalis* agglutinin (GNA).

67. The method of any one of alternatives 55-66, further comprising observing or measuring a reduction in number of coronavirus virions, or portions thereof; number of exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T, or any combination thereof, in a sample of the patient's blood taken after (b) relative to a sample of the patient's blood taken before (b).

68. The method of any one of alternatives 55-67, wherein the coronavirus infection is caused by a coronavirus selected from SARS-CoV-2, SARS-CoV-1, MERS-CoV, HCoV-229E, HCoV-OC43, HCoV NL63, or HCoV-HKU1.

69. The method of alternative 68, wherein the SARS-CoV-2 is a SARS-CoV-2 variant. The method of alternative 34, wherein the SARS-CoV-2 variant is selected from 20I/501Y.V1 (B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429).

70. A method for reducing the amount of SARS-CoV-2 virions, or fragments thereof, in a COVID-19 patient, comprising:
(a) providing an extracorporeal device comprising a hollow fiber cartridge comprising a lectin that selectively binds to the outer surfaces of SARS-CoV-2 virions, or fragments thereof;
(b) removing blood from a COVID-19 patient;
(c) processing the blood from the hollow fiber cartridge such that the lectin is in contact with the blood;
(d) reducing at least a portion of SARS-CoV-2 virions, or fragments thereof such that said portion of SARS-CoV-2 virions, or fragments thereof is retained in the hollow fiber cartridge; and
(e) reintroducing the blood without said portion of SARS-CoV-2 virions, or fragments thereof to the patient.

71. A method for reducing the amount of COVID-19 mediating nanoparticles in a COVID-19 patient, comprising:
(a) providing an extracorporeal device comprising a hollow fiber cartridge comprising a lectin that selectively binds to the outer surfaces of COVID-19 mediating nanoparticles;
(b) removing blood from a COVID-19 patient;
(c) processing the blood from the hollow fiber cartridge such that the lectin is in contact with the blood;
(d) reducing at least a portion of COVID-19 mediating nanoparticles such that said portion of COVID-19 mediating nanoparticles is retained in the hollow fiber cartridge; and
(e) reintroducing the blood without said portion of COVID-19 mediating nanoparticles to the patient.

72. A method for reducing the amount of COVID-19 mediating exosomes, in a COVID-19 patient, comprising:
(a) providing an extracorporeal device comprising a hollow fiber cartridge comprising a lectin that selectively binds to the outer surfaces of COVID-19 mediating exosomes;
(b) removing blood from a COVID-19 patient;
(c) processing the blood from the hollow fiber cartridge such that the lectin is in contact with the blood;
(d) reducing at least a portion of COVID-19 mediating exosomes such that said portion of COVID-19 mediating exosomes is retained in the hollow fiber cartridge; and
(e) reintroducing the blood without said portion of COVID-19 mediating exosomes to the patient.

73. A method for reducing the amount of circulating IL-1, IL-6, IL-10, IL-15, CXCL10, CCL2, Myeloperoxidase, VCAM-1, TNF alpha, C-reactive protein (CRP), D-dimer, or Troponin-T or any combination thereof in a COVID-19 patient comprising:
(a) providing an extracorporeal device comprising a hollow fiber cartridge comprising a lectin that selectively binds to the outer surfaces SARS-CoV-2 virions or fragments thereof or COVID-19 mediating exosomes;
(b) removing blood from a COVID-19 patient;
(c) measuring the levels of IL-1, IL-6, IL-10, IL-15, CXCL10, CCL2, Myeloperoxidase, VCAM-1, TNF alpha, C-reactive protein (CRP), D-dimer, or Troponin-T or any combination thereof in the plasma or blood;
(d) processing the blood from the hollow fiber cartridge such that the lectin is in contact with the blood;
(e) reducing at least a portion of COVID-19 mediating exosomes such that said portion of SARS-CoV-2 virions or fragments thereof or COVID-19 mediating exosomes is retained in the hollow fiber cartridge;
(f) measuring the levels of IL-1, IL-6, IL-10, IL-15, CXCL10, CCL2, Myeloperoxidase, VCAM-1, TNF alpha, C-reactive protein (CRP), D-dimer, or Troponin-T or any combination thereof in the plasma or blood; and
(g) reintroducing the blood without said portion of surfaces SARS-CoV-2 virions or fragments thereof or COVID-19 mediating exosomes to the patient.

74. A method for reducing the amount of circulating D-dimer in a COVID-19 patient comprising:
(a) providing an extracorporeal device comprising a hollow fiber cartridge comprising a lectin that selectively binds to the outer surfaces SARS-CoV-2 virions or fragments thereof or COVID-19 mediating exosomes;
(b) removing blood from a COVID-19 patient;
(c) measuring the levels of D-dimer in the plasma or blood;
(d) processing the blood from the hollow fiber cartridge such that the lectin is in contact with the blood;
(e) reducing at least a portion of COVID-19 mediating exosomes such that said portion of SARS-CoV-2 virions or fragments thereof or COVID-19 mediating exosomes is retained in the hollow fiber cartridge; measuring the levels of D-dimer in the blood; and reintroducing the blood without said portion of surfaces SARS-CoV-2 virions or fragments thereof or COVID-19 mediating exosomes to the patient.

75. A method for reducing the amount of Troponin T in a COVID-19 patient comprising:
(a) providing an extracorporeal device comprising a hollow fiber cartridge comprising a lectin that selectively binds to the outer surfaces SARS-CoV-2 virions or fragments thereof or COVID-19 mediating exosomes;
(b) removing blood from a COVID-19 patient;
(c) measuring the levels of Troponin T in the plasma or blood;
(d) processing the blood from the hollow fiber cartridge such that the lectin is in contact with the blood;
(e) reducing at least a portion of COVID-19 mediating exosomes such that said portion of SARS-CoV-2 virions or fragments thereof or COVID-19 mediating exosomes is retained in the hollow fiber cartridge;
(f) measuring the levels of Troponin T in the plasma or blood; and
(g) reintroducing the blood without said portion of surfaces SARS-CoV-2 virions or fragments thereof or COVID-19 mediating exosomes to the patient.

76. The method of alternatives 70-75, wherein the lectin is GNA.

BRIEF DESCRIPTION OF THE DRAWINGS

In addition to the features described above, additional features and variations will be readily apparent from the following descriptions of the drawings and exemplary embodiments. It is to be understood that these drawings depict typical embodiments and are not intended to be limiting in scope.

DETAILED DESCRIPTION

Figures 1, 2, 3:
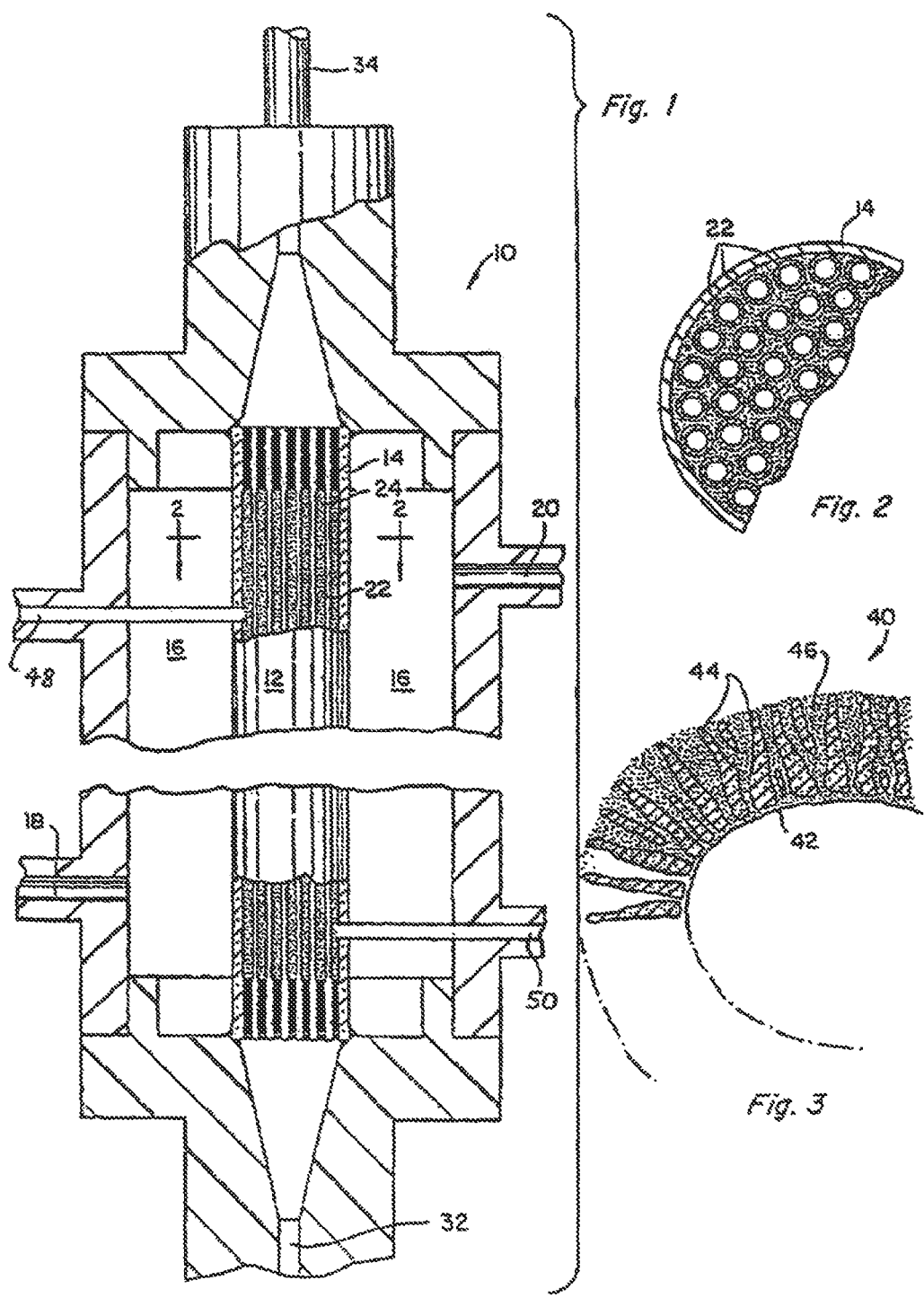
FIG. 1 is a schematic illustration of a longitudinal cross section of an affinity cartridge.
FIG. 2 is a schematic illustration of a horizontal cross section at plane 2 in FIG. 1.
FIG. 3 is an illustration of a channel from FIG. 2. A hollow fiber membrane structure 40 is composed of a tubular section comprising a relatively tight ultrafiltration membrane 42 and relatively porous exterior portion 44 in which may be immobilized affinity molecules 46, such as lectins.

Disclosed herein are extracorporeal devices and their uses to treat or inhibit a coronavirus infection, e.g., a beta corona virus infection, such as COVID-19, or a symptom or sequela associated with the coronavirus infection. The severe impact of the widespread COVID-19 pandemic has necessitated rapid development of effective and safe therapeutics and prophylaxes of the causative agent, SARS-CoV-2. While some vaccines and treatments have now been approved, it has become apparent that the emergence of SARS-CoV-2 mutants and variants, including those having greater virulence and/or potential to evade current therapeutics, threaten to prolong the pandemic. Furthermore, many patients who have overcome a COVID-19 infection continue to exhibit debilitating symptoms and sequela, including permanent lung scarring and fibrosis, heart complications and failure, strokes, seizures, and immunological disorders such as Guillain-Barre syndrome. The devices disclosed herein function in ways that are effective against SARS-CoV-2 variants, as well as, treating or inhibiting the underlying causes of sequela associated with a current or past COVID-19 infection, including within a subpopulation of patients that do not have circulating viral particles but continue to present sequelae associated with COVID-19 infection e.g., the "long hauler" patient.

Definitions

Unless defined otherwise, all technical and scientific terms used herein have the same meaning as is commonly understood by one of ordinary skill in the art. All patents, applications, published applications and other publications referenced herein are expressly incorporated by reference in their entireties unless stated otherwise. In the event that there are a plurality of definitions for a term herein, those in this section prevail unless stated otherwise.

The articles "a" and "an" are used herein to refer to one or to more than one (for example, at least one) of the grammatical object of the article. By way of example, "an element" means one element or more than one element.

The terms "about" or "around" as used herein refer to a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

Unless defined otherwise, all technical and scientific terms used herein have the same meaning as is commonly understood by one of ordinary skill in the art to which this disclosure belongs. If there is a plurality of definitions for a term herein, those in this section prevail unless stated otherwise. The practice of the present disclosure will employ, unless indicated specifically to the contrary, conventional methods of molecular biology and recombinant DNA techniques within the skill of the art, many of which are described below for the purpose of illustration.

The terms "individual", "subject", or "patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice, guinea pigs, or the like.

The terms "function" and "functional" as used herein refer to a biological, enzymatic, or therapeutic function.

The term "isolated" as used herein refers to material that is substantially or essentially free from components that normally accompany it in its native state. For example, an "isolated cell," as used herein, includes a cell that has been purified from the milieu or organisms in its naturally occurring state, a cell that has been removed from a subject or from a culture, for example, it is not significantly associated with in vivo or in vitro substances.

"Formulation", "pharmaceutical composition", and "composition" as used interchangeably herein are equivalent terms referring to a composition of matter for administration to a subject.

The term "pharmaceutically acceptable" means compatible with therapy for a subject, and in particular, a human.

The terms "agent" refers to an active agent that has biological activity and may be used in a therapy. Also, an "agent" can be synonymous with "at least one agent," "compound," or "at least one compound," and can refer to any form of the agent, such as a derivative, analog, salt or a prodrug thereof. The agent can be present in various forms, components of molecular complexes, and pharmaceutically acceptable salts (e.g., hydrochlorides, hydrobromides, sulfates, phosphates, nitrates, borates, acetates, maleates, tartrates, or salicylates). The term "agent" can also refer to any pharmaceutical molecules or compounds, therapeutic molecules or compounds, matrix forming molecules or compounds, polymers, synthetic molecules and compounds, natural molecules and compounds, and any combination thereof.

The term "purity" of any given substance, compound, or material as used herein refers to the actual abundance of the substance, compound, or material relative to the expected abundance. For example, the substance, compound, or material may be at least 80, 85, 90, 91, 92, 93, 94, 95, 96, 97, 98, 99, or 100% pure, including all decimals in between. Purity may be affected by unwanted impurities, including but not limited to side products, isomers, enantiomers, degradation products, solvent, carrier, vehicle, or contaminants, or any combination thereof. Purity can be measured technologies including but not limited to chromatography, liquid chromatography, gas chromatography, spectroscopy, UV-visible spectrometry, infrared spectrometry, mass spectrometry, nuclear magnetic resonance, gravimetry, or titration, or any combination thereof.

Some embodiments disclosed herein related to selecting a subject or patient in need for any one or more of the extracorporeal methods described herein. In some embodiments, a patient is selected for any one or more of the extracorporeal methods described herein who is in need of treatment or inhibition of a coronavirus infection, e.g., a beta corona virus infection, such as a SARS-CoV-2 infection. In some embodiments, a patient is selected for any one or more of the extracorporeal methods described herein who has previously received a therapy for a coronavirus infection, such as a SARS-CoV-2 infection. In some embodiments, a patient is selected for any one or more of the extracorporeal methods described herein who has previously received a therapy for being at risk of a coronavirus infection e.g., a beta corona virus infection, such as a SARS-CoV-2 infection. In some embodiments, a patient is selected for any one or more of the extracorporeal methods described herein who has developed a recurrence of a coronavirus infection, e.g., a beta corona virus infection, such as a SARS-CoV-2 infection. In some embodiments, a patient is selected for any one or more of the extracorporeal methods described herein who has developed resistance to therapies for a coronavirus infection, e.g., a beta corona virus infection, such as a SARS-CoV-2 infection. In some embodiments, a patient is selected for any one or more of the extracorporeal methods described herein who exhibits a symptom or sequela of a coronavirus infection, e.g., a beta corona virus infection, such as a SARS-CoV-2 infection. In some embodiments, a patient is selected for any one or more of the extracorporeal methods described herein who has cleared a coronavirus infection, e.g., a beta corona virus infection, e.g., has no amount or a diminished or reduced amount of circulating viral particles in the plasma or blood, but continues to exhibit a symptom or sequela of the coronavirus infection, e.g., a beta corona virus infection, such as a SARS-CoV-2 infection. In some embodiments, a patient is selected for any one or more of the extracorporeal methods described herein who has developed a coagulopathy, such as a COVID-19 associated coagulopathy, or who is at risk of developing a coagulopathy (e.g., a patient having levels or amounts of IL-1, IL-6, IL-10, IL-15, CXCL10, CCL2, Myeloperoxidase, VCAM-1, TNF alpha, C-reactive protein (CRP), D-dimer, or Troponin-T or any combination thereof, that exceed levels of a control or baseline, such as the level or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof found in a healthy patient or a patient that does not have a coagulopathy or a patient that is not at risk of a coagulopathy). These patients having a coagulopathy or that are at risk of developing a coagulopathy may or may not have or have had a viral infection, such as COVID-19. In some embodiments, a patient is selected for any one or more of the extracorporeal methods described herein who has developed hypoxia (e.g., a patient having oxygen levels that are reduced as compared to a healthy patient or a patient that does not have hypoxia. These patients having hypoxia may or may not have or have had a viral infection, such as COVID-19. In some embodiments, a patient is selected for any one or more of the extracorporeal methods described herein who may have any combination of the aforementioned selection criteria. Such selections may be made by clinical or diagnostic evaluation of the subject as is routine in the field.

The terms "treat", "treating", "treatment", "therapeutic", or "therapy" as used herein has its ordinary meaning as understood in light of the specification, and do not necessarily mean total cure or abolition of the disease or condition. The term "treating" or "treatment" as used herein (and as well understood in the art) also means an approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable. "Treating" and "treatment" as used herein also include prophylactic treatment. Treatment methods comprise administering to a subject a therapeutically effective amount of an active agent or use of a therapeutic device. The administering step may consist of a single administration or may comprise a series of administrations. The compositions are administered or applied to the subject in an amount, for a duration, or for a number or repetitions sufficient to treat the patient. The length of the treatment period depends on a variety of factors, such as the severity of the condition, the age and genetic profile of the patient. It will also be appreciated that the treatment or prophylaxis may be modified over the course of a particular treatment or prophylaxis regime. In some instances, chronic administration or application may be required. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from or developing a disease or condition.

The term "inhibit" as used herein has its ordinary meaning as understood in light of the specification, and may refer to the reduction or prevention of a viral infection, such as SARS-CoV-2, or a symptom or sequela thereof. The reduction can be by 10%, 20%, 30%, 40%, 50%, 60%, 70%, 80%, 90%, or 100%, or an amount that is within a range defined by any two of the aforementioned values. As used herein, the term "delay" has its ordinary meaning as understood in light of the specification, and refers to a slowing, postponement, or deferment of an event, such as a viral infection, or a symptom or sequela thereof, to a time which is later than would otherwise be expected. The delay can be a delay of 0%, 10%, 20%, 30%, 40%, 50%, 60%, 70%, 80%, 90%, 100%, or an amount within a range defined by any two of the aforementioned values. The terms inhibit and delay may not necessarily indicate a 100% inhibition or delay. A partial inhibition or delay may be realized.

The terms "nucleic acid" or "nucleic acid molecule" as used herein refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, or phosphoramidate. The term "nucleic acid molecule" also includes so-called "peptide nucleic acids," which comprise naturally-occurring or modified nucleic acid bases attached to a polyamide backbone. Nucleic acids can be either single stranded or double stranded. "Oligonucleotide" can be used interchangeable with nucleic acid and can refer to either double stranded or single stranded DNA or RNA. A nucleic acid or nucleic acids can be contained in a nucleic acid vector or nucleic acid construct (e.g. plasmid, virus, bacteriophage, cosmid, fosmid, phagemid, bacterial artificial chromosome (BAC), yeast artificial chromosome (YAC), or human artificial chromosome (HAC)) that can be used for amplification and/or expression of the nucleic acid or nucleic acids in various biological systems. Typically, the vector or construct will also contain elements including but not limited to promoters, enhancers, terminators, inducers, ribosome binding sites, translation initiation sites, start codons, stop codons, polyadenylation signals, origins of replication, cloning sites, multiple cloning sites, restriction enzyme sites, epitopes, reporter genes, selection markers, antibiotic selection markers, targeting sequences, peptide purification tags, or accessory genes, or any combination thereof.

A nucleic acid or nucleic acid molecule can comprise one or more sequences encoding different peptides, polypeptides, or proteins. These one or more sequences can be joined in the same nucleic acid or nucleic acid molecule adjacently, or with extra nucleic acids in between, e.g. linkers, repeats or restriction enzyme sites, or any other sequence that is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, or 300 bases long, or any length in a range defined by any two of the aforementioned lengths. The term "downstream" on a nucleic acid as used herein refers to a sequence being after the 3'-end of a previous sequence, on the strand containing the encoding sequence (sense strand) if the nucleic acid is double stranded. The term "upstream" on a nucleic acid as used herein refers to a sequence being before the 5'-end of a subsequent sequence, on the strand containing the encoding sequence (sense strand) if the nucleic acid is double stranded. The term "grouped" on a nucleic acid as used herein refers to two or more sequences that occur in proximity either directly or with extra nucleic acids in between, e.g. linkers, repeats, or restriction enzyme sites, or any other sequence that is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, or 300 bases long, or any length in a range defined by any two of the aforementioned lengths, but generally not with a sequence in between that encodes for a functioning or catalytic polypeptide, protein, or protein domain.

The terms "peptide", "polypeptide", and "protein" as used herein refers to macromolecules comprised of amino acids linked by peptide bonds. The numerous functions of peptides, polypeptides, and proteins are known in the art, and include but are not limited to enzymes, structure, transport, defense, hormones, or signaling. Peptides, polypeptides, and proteins are often, but not always, produced biologically by a ribosomal complex using a nucleic acid template, although chemical syntheses are also available. By manipulating the nucleic acid template, peptide, polypeptide, and protein mutations such as substitutions, deletions, truncations, additions, duplications, or fusions of more than one peptide, polypeptide, or protein can be performed. These fusions of more than one peptide, polypeptide, or protein can be joined in the same molecule adjacently, or with extra amino acids in between, e.g. linkers, repeats, epitopes, or tags, or any other sequence that is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, or 300 bases long, or any length in a range defined by any two of the aforementioned lengths. The term "downstream" on a polypeptide as used herein refers to a sequence being after the C-terminus of a previous sequence. The term "upstream" on a polypeptide as used herein refers to a sequence being before the N-terminus of a subsequent sequence.

As used herein, a "lectin" is a protein that bind selectively to polysaccharides and glycoproteins. Although many are insufficiently specific to be useful, certain lectins are highly selective for enveloped viruses. Among lectins which have this property are those derived from *Galanthus nivalis* in the form of *Galanthus nivalis* agglutinin ("GNA"), *Narcissus pseudonarcissus* in the form of *Narcissus pseudonarcissus* agglutinin ("NPA") and a lectin derived from blue green algae *Nostoc ellipsosporum* called "cyanovirin". GNA is non-toxic and sufficiently safe that it has been incorporated into genetically engineered rice and potatoes (Bell et al. Transgenic Res 10(1): 35-42, 2001; Rao et al. Plant J 15(4): 469-477, 1998). These lectins bind to glycoproteins having a high mannose content such as found in HIV surface proteins (Chervenak et al. Biochemistry 34(16): 5685-5695, 1995).

As used herein, a "high mannose glycoprotein" refers to a glycoprotein having mannose-mannose linkages in the form of α-1→3 or α-1→6 mannose-mannose linkages.

The term "coronavirus" as used herein refers to the family of enveloped, positive-sense, single stranded RNA viruses belonging to the family Coronaviridae that infect mammals and birds. In humans, coronavirus infections can cause mild symptoms as a common cold, or more severe respiratory conditions such as severe acute respiratory syndrome (SARS), acute respiratory distress syndrome (ARDS), coughing, congestion, sore throat, shortness of breath, pneumonia, bronchitis, and hypoxia. Other symptoms include but are not limited to fever, fatigue, myalgia, and gastrointestinal symptoms such as vomiting, diarrhea, and abdominal pain. To infect host cells, enveloped viruses must fuse with the host cell membrane and deliver their genome into the cell. The viral envelope comprises spike ("S"), envelope ("E"), membrane ("M"), and hemagglutinin esterase ("HE") transmembrane structural proteins. Coronaviruses have average diameters of 80-120 nm and virion surfaces that are densely covered in projections of trimeric S glycoproteins that are decorated with N-linked glycosylation sequences. The S protein comprises a receptor binding domain ("RBD"), a highly immunogenic region that determines the host receptor specificity of the virus strain. The viral nucleocapsid comprises multiple nucleocapsid ("N" or "NP") proteins coating the RNA genome. During infection, the S protein attaches to a host cell receptor and initiate entry into the host cell through endocytosis or fusion of the envelope membrane. The RNA genome is translated by the host ribosome to produce new structural proteins and RNA-dependent RNA polymerases, which replicate the viral genome. Viral particles are assembled in the host endoplasmic reticulum and are shed by Golgi-mediated exocytosis. More information about the structure and infection cycle of coronaviruses can be found in Fehr A R & Perlman S. "Coronaviruses: An Overview of Their Replication and Pathogenesis" *Methods Mol. Biol.* (2015); 1282:1-23, hereby expressly incorporated by reference in its entirety.

The terms "SARS-CoV-2" and "2019-nCoV" as used herein refers to the coronavirus strain or strains responsible for the human coronavirus disease 2019 (COVID-19) pandemic. The contagiousness, long incubation period, and modern globalization has led to worldwide spread of the virus. Development of SARS and other respiratory issues in infected individuals has resulted in immense stress on medical infrastructure. Treatments and vaccines for SARS-CoV-2 and other coronaviruses in humans are starting to be approved, but additional testing is necessary. The embodiments disclosed herein can be applied to other coronaviruses, including but not limited to HCoV-229E, HCoV-OC43, SARS-CoV-1, HCoV NL63, HCoV-HKU1, and MERS-CoV, as well as SARS-CoV-2 variants, including but not limited to 20I/501 Y.V1 (B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429). It is envisioned that the devices and methods of use will be effective against a coronavirus infection caused by other SARS-CoV-2 variants that are identified or that are currently unknown.

According to the National Institute for Health and Care Excellence (NICE) of the United Kingdom, a COVID-19 infection is categorized as any of the following "acute COVID-19" is associated with signs and symptoms of COVID-19 for up to 4 weeks; "ongoing symptomatic COVID-19" is associated with signs and symptoms of COVID-19 from 4 to 12 weeks; and "post-COVID-19 syndrome" is associated with signs and symptoms that develop during or after an infection consistent with COVID19, continue for more than 12 weeks and are not explained by an alternative diagnosis.

As used herein "COVID-19-associated coagulopathy" (CAC) refers to thrombotic complications associated with a COVID-19 infection. As SARS-CoV-2 is able to infect vascular endothelial cells through ACE2, significant inflammation and damage to the cardiovascular system may be experienced by the patient over the course of the disease. Some hallmarks associated with CAC involves a decrease in platelet count, increase in the circulating D-dimer, prolongation of the prothrombin time (PT), and the presence of macro-thrombosis and/or micro-thrombosis. Additional information on CAC can be found in Iba et al. *J. Clin. Med.* (2021) 10; 191, which is hereby incorporated by reference in its entirety.

As used herein, a "SARS-CoV-2 derived glycoprotein" includes any glycoprotein contained or expressed by the SARS-CoV-2 virus. For example, a SARS-CoV-2 derived glycoprotein encompassed by the present invention is the SARS-CoV-2 S (spike) protein, comprising the outermost glycoprotein-decorated moieties of the viral envelope, or subunits thereof, including the S1, S2, and RBD subunits.

As used herein, the "SARS-CoV-2 S spike protein" or "COVID-19 spike protein" includes the S protein which is a class I viral fusion protein consisting of a single chain of approximately 1,300 amino acids that trimerizes after folding, comprising an N-terminal S1 subunit with the receptor-binding domain, and a C-terminal S2 subunit responsible for membrane fusion. During viral assembly, coronavirus proteins undergo numerous post-translational modifications, including heavy glycosylation that has an essential role in viral pathogenesis. The S trimers on the coronavirus surface are extensively decorated with N-linked glycans that represent critical moieties for viral function. The N-linked glycan moieties on the coronavirus surfaces are critical for both viral assembly and functions. These glycans are needed for stability during the generation of S proteins; inhibition of N-glycosylation by tunicamycin resulted in the synthesis of "spikeless" virions. The coating of the viral envelope by N-glycans also masks immunogenic protein epitopes, forming a glycan shield that allows coronaviruses to evade the host immune system and host proteases. Coronavirus glycoproteins are therefore principal antigenic determinants that represent primary targets of therapeutic interventions and vaccines. These highly conserved glycoproteins on SARS-CoV-2 and other coronaviruses, e.g., a beta corona virus such as COVID-19 and variants thereof, are therefore believed to be ideal targets for the lectin-based affinity devices described herein. Accordingly, it is contemplated that the devices and procedures described herein are useful for the removal of SARS-CoV-2 and other coronaviruses, e.g., a beta corona virus such as COVID-19 and variants thereof, as well as exosomes having antigens from said virus, even if such virus mutate overtime e.g., generate new variants.

As used herein, "exosomes" are nanoparticles of 200 nm in size or less that are a part of a communication system that conveys signals to near or distant target cells and reprograms their functions. The contents of exosomes vary, and can include nucleic acids, proteins, and lipids. They can be transferred from host to recipient cells to alter cellular function. They function as a mode of intercellular communication and molecular transfer, and facilitate the direct extracellular transfer of specific proteins, and lipids, as well as, miRNA, mRNA, and DNA between cells. Exosomes are present in the systemic circulation and are distributed throughout the body. In normal, healthy individuals, a basal level of exosome release aids in cell-to-cell communication and promotes elimination of cellular debris. However, it is contemplated that an increase in exosome quantity reflects an altered physiological state. Exosomes are released in abundance in pathological states where they are deployed by activated cells in large quantities and transfer their membrane composition and internal cargo to distant tissues via the circulatory system, for instance. Additional information about exosomes and purification of constituent material may be found in PCT Publication WO 2016/172598, which is hereby expressly incorporated by reference in its entirety.

As used herein, "COVID-19 mediating nanoparticle" includes any nanoparticle, i.e., 200 nm or less in size, that contains or expresses a SARS-CoV-2 derived glycoprotein, or a subcellular nanoparticle associated with COVID-19, or a symptom or sequela thereof, which is not necessarily derived from a SARS-CoV-2 particle. For example, a COVID-19 mediating nanoparticle may be a SARS-CoV-2 virion, or fragments thereof such as SARS-CoV-2-derived glycoprotein, as well as, a non-viral COVID-19 mediating nanoparticle or an exosome.

As used herein, the term "portion" refers to an amount of a material that is less than a whole. A minor portion refers to an amount that is, for example, less than 50%, and a major portion refers, for example, to an amount greater than 50%. Thus, a unit of coronavirus particles, COVID-19 mediating nanoparticles, or exosomes that is less than the entire amount of coronavirus particles, COVID-19 mediating nanoparticles, or exosomes removed from a subject is a portion of the removed coronavirus particles, COVID-19 mediating nanoparticles, or exosomes. In reference to the disclosure herein, coronavirus particles, COVID-19 mediating nanoparticles, or exosomes, or a unit thereof may refer to the entire amount of the coronavirus particles, COVID-19 mediating nanoparticles, or exosomes removed from a subject, or an amount that is less than the entire amount of coronavirus particles, COVID-19 mediating nanoparticles, or exosomes removed from a subject. In some embodiments, the subject includes warm-blooded animals, preferably mammals, including humans. In a preferred embodiment, the subject is a primate. In a more preferred embodiment, the subject is a human.

As used herein, the term "microRNA" or "miRNA" refers to highly conserved non-coding RNA molecules, about 21-25 nucleotides in length that play critical roles in regulating post-transcriptional gene expression by targeting messenger RNA (mRNA) of protein-coding genes. Mature miRNAs exist in the cellular cytoplasm as RNA duplexes to which an argonaute (Ago2) protein and a glycine-tryptophan repeat-containing protein bind, forming the core of a multi-subunit complex called the miRNA-mediating silencing complex (miRISC). The miRNA duplex contains two strands identified with either the suffix "-5p" (from the 5' arm of pre-miRNA) or "-3p" (from the 3' arm of the pre-miRNA). One of the strands of the duplex is typically discarded (passenger strand) while the retained strand guides mRNA target selection (guide strand). However, in some cases, two mature miRNAs excised from the 5' and 3' arms of the same stem-loop pre-miRNA have been reported to be functional and target on different mRNA. Once assembled into the miRISC through base-pairing interactions between nucleotides 2 and 8 of the miRNA and complementary nucleotides predominantly in the 3'-untranslated regions (UTR) of mRNAs, miRNAs act as repressors of translation. Each miRNA binds to many specific target mRNAs and often not to those in the same molecular pathway. miRNAs exist as both free-floating entities in plasma and other biofluids and also packaged into exosomes. It is believed that extracellular, non-exosomal miRNAs in circulation are by-products of dead cells stably bound to the Ago2 protein. Exosomes, which are produced in large quantities by diseased and activated cells, are packed with a full complement of the parent cell's cargo, including miRNA.

Some miRNAs have been identified as ubiquitously associated with various diseases. Specific miRNAs have been described as "fine-tuners" of immune responses that can either promote an inflammatory state or have anti-inflammatory effects by regulating toll-like receptor signaling. miRNAs are also non-antigenic, allowing them to escape immune surveillance, which can be beneficial for the virus. In viral infections, certain miRNAs may serve both as antiviral tools that stimulate the innate and adaptive immune systems while others have roles in viral propagation. Host miRNAs can be regulated by viruses and viruses can also usurp cellular resources to produce their own miRNAs that participate in immune evasion and maintaining infection. The presence of the various viral and host miRNAs may be monitored when evaluating the outcome of a therapeutic strategy.

Exosomes are believed to be crucial in disseminating pathogenic material as well as host-derived molecules during viral infections, thereby contributing to viral infectivity and disease complications. For example, dissemination of miRNAs via exosomes can serve as a mechanism that viruses use to escape the immune system and allow for continual infection of host cells. An example is the infection of hepatocytes with hepatitis B virus (HBV), which leads to the release of exosomal miRNAs from virus-infected cells that attenuate the production of cytokines involved in antiviral immunity. It has been hypothesized that extracellular vesicles produced in response to many viruses including coronaviruses contribute to coagulopathy as well as to maintaining the pathological state and promoting the spread of infection. In COVID-19, viral and/or host miRNAs transported in exosomes and dispersed systemically may act as mediators of thrombosis, immune dysfunction, and multi-organ injury. The existence of miRNA that is transferred between cells via exosomes and that has a distinctive pathogenic role from infectious virions is an important component to understanding the pathogenesis of COVID-19. The devices disclosed herein, by virtue of its affinity for high-mannose glycoprotein moieties, has the capacity to bind and remove SARS-CoV2 as well as exosomes from the circulatory system.

Where a range of values is provided, it is understood that the upper and lower limit, and each intervening value between the upper and lower limit of the range is encompassed within the embodiments.

The term "% w/w" or "% wt/wt" as used herein has its ordinary meaning as understood in light of the specification and refers to a percentage expressed in terms of the weight of the ingredient or agent over the total weight of the composition multiplied by 100. The term "% v/v" or "% vol/vol" as used herein has its ordinary meaning as understood in the light of the specification and refers to a percentage expressed in terms of the liquid volume of the compound, substance, ingredient, or agent over the total liquid volume of the composition multiplied by 100.

COVID-19 Symptoms and Sequela

As information concerning SARS-CoV-2 pathogenesis has emerged, it has become apparent that this virus not only targets the respiratory tract but, in more serious cases, is also capable of eliciting massive systemic inflammation and exploiting the vulnerabilities of other organs, which may lead to respiratory failure, acute cardiac injury, acute kidney injury, neurological disorders, sepsis, or other complications. There is also evidence for "RNAemia" (i.e., the presence of viral RNA in blood) in COVID-19 patients, which indicates that a systemic viral load may promote inflammation and tissue injury as further described herein.

COVID-19 Disease—Cytokine Storm. Recent data suggest that SARS-CoV-2-induced immunopathological events underlie ARDS as well as other systemic sequelae that occur in COVID-19. A subset of patients with COVID-19, in particular those with severe disease, show evidence of the "cytokine storm" in blood: unbridled and dysregulated inflammation that is believed to culminate in tissue damage, pulmonary edema, and deterioration of normal immune functions. When moderate vs. severe cases of COVID-19 are compared, severe cases more frequently presented with dyspnea, and hypoalbuminemia, with higher levels of alanine aminotransferase, lactate dehydrogenase, C-reactive protein (CRP), ferritin and D-dimer as well as markedly elevated systemic levels of cytokines and receptors; namely, IL-2R, IL-6, IL-10, and TNF-α. Due to the association that exists between severe inflammation and poor outcomes in COVID-19 patients, inflammatory markers may serve as surrogates for evaluating the outcomes of a therapeutic intervention in COVID-19 patients by measuring changes in specific cytokines, chemokines and combinations thereof including IL-1 beta, IL-6, IL-8, IL-10, granulocyte-colony stimulating factor (G-CSF), interferon gamma-induced protein 10 (IP-10), monocyte chemoattractant protein-1 (MCP-1), and macrophage inflammatory proteins (MIP-1 alpha and MIP-1 beta). Circulating cytokines such as IL-6 have been shown to be a biomarker for COVID-19 infection severity (Zhang et al. *J. Translational Medicine* (2020) 18(1):406).

COVID-19 Disease—Immune Suppression. The elevated levels of cytokines in the pathogenesis of COVID-19 also correlate with attrition of CD4+ T cells, CD8+ T cells, and natural killer (NK) cells in SARS-CoV-2 infections. The total numbers of CD4+ and CD8+ T cells are dramatically reduced in COVID-19 patients, especially among patients ≥60 years of age and in those requiring ICU care. The virus either directly or indirectly leads to lymphocyte loss and/or the inflammatory process, fueled by by-products of the infection, and causes lymphocyte apoptosis. There is evidence that the absolute numbers of lymphocytes in blood and/or percentages of lymphocytes among white blood cells are indicative of disease progression and outcomes for COVID-19 patients, whereby patients with moderate to severe disease symptoms who recover present with improvements in the lymphocyte levels and critically-ill patients who die do not recover from lymphopenia. Hence, absolute counts for lymphocytes can be used to identify the presence of lymphopenia using laboratory reference ranges known in the art and may be used to predict COVID-19 patients' status and prognosis. Additionally, the numbers of specific lymphocytes (e.g., T cells and NK cells) and of specific lymphocyte subsets (CD4+ T cells and CD8+ T cells) in the peripheral blood of patients with COVID-19 can serve to identify the status of the immune system, in particular of cell types that are involved in anti-viral responses.

COVID-19 Disease—RNAemia. Viral RNA in plasma ("RNAemia") in hospital-admitted patients who tested positive for COVID-19 have been demonstrated. RNAemia has also been observed in critically ill patients with COVID-19 and correlated with elevated levels of the pro-inflammatory cytokine IL-6. This indicates that systemic SARS-CoV-2 viral loads correlate with the severity of COVID-19. Accordingly, reducing viral loads or the circulating viral RNA using the methods described herein will improve the recovery of critically ill patients with COVID-19.

The term "viral load" as used herein refers to the amount of viral particles, viral RNA, or fragments thereof in a biological fluid, such as blood or plasma. "Viral load" encompasses all viral particles (either infectious, replicative, or non-infective), and fragments thereof. Therefore, viral load represents the total number of viral particles and/or fragments thereof circulating in the biological fluid. Viral load can therefore be a measure of any of a variety of indicators of the presence of a virus, such as viral copy number per unit of blood or plasma or units of viral proteins or fragments thereof per unit of blood or plasma. The presence of SARS-CoV-2 viral RNA in circulation correlates with poor outcomes. The changes in circulating viral burden can be evaluated by RT-PCR. Viral clearance may be quantitated by elution of viral particles bound to lectin, including those disclosed herein.

COVID-19 Disease—Cardiac Complications. Myocardial injury is significantly associated with fatal outcome of COVID-19, while the prognosis of patients with underlying cardiovascular disease (CVD) but without myocardial injury is relatively favorable. Myocardial injury is associated with cardiac dysfunction and arrhythmias. Inflammation may be a potential mechanism for myocardial injury. Use of any one or more of the methods described herein may be considered for patients at high risk of myocardial injury and such methods can be employed multiple times (e.g., one, two, three, four, five, six, seven, eight, nine, or ten times) over a therapy period.

As disclosed herein, "troponin" is a type of protein found in the muscles of your heart. Troponin, and subunits thereof (e.g. troponin C, troponin I, troponin T) is not normally found in the blood. When heart muscles become damaged, troponin is sent into the bloodstream. As heart damage increases, greater amounts of troponin are released in the blood.

Among COVID-19 patients, those who are at risk of myocardial injury, as assessed by elevated troponin T levels, are older and have a higher prevalence of hypertension, coronary artery disease, heart failure, and diabetes. Patients with myocardial injury also have evidence of more severe systemic inflammation, including greater leukocyte counts and higher levels of C-reactive protein and procalcitonin as well as high levels of other biomarkers of myocardial injury and stress, such as elevated creatine kinase, myoglobin, and N-terminal pro-B-type natriuretic peptide (NT-proBNP). These patients also have a higher incidence of systemic inflammation as well as a need for assisted ventilation than COVID-19 patients without myocardial injury. Troponins may include and/or be referred as: cardiac troponin I (cTnI), cardiac troponin T (cTnT), cardiac troponin (cTN), cardiac-specific troponin I and troponin T. Circulating troponin T has been shown to be a biomarker for COVID-19 infection severity (Gaze. *Ann. Clin. Biochem.* (2020) 57(3):202-205).

COVID-19 Disease—Multiorgan Failure, Sepsis, Acute Kidney Disease, Neurological Disorders, Olfactory Disorders, Hyperinflammation & Other Complications. For critically ill patients with COVID-19, improvements in markers of systemic inflammation and/or injury to organs may serve as measurements of a clinically effective therapeutic intervention. The markers that are expected to be reduced in response to a therapeutic intervention may include C-reactive protein (CRP), ferritin, lactate dehydrogenase, alanine aminotransferase (ALT), interleukin-6 (IL-6), IL-1 beta, tumor necrosis factor-alpha (TNF-α), macrophage inflammatory protein 1-alpha, granulocyte-colony-stimulating factor, interferon-gamma inducible protein 10 and/or monocyte chemoattractant protein 1. To evaluate clinical outcomes related to a therapeutic intervention for COVID-19, evaluations of survival, the duration and need for assisted ventilation, the multiorgan systems failure, and cardiac complications may be monitored.

COVID-19 Disease—Coagulation. A D-dimer test looks for D-dimer in blood. D-dimer is a protein fragment produced by the degradation of cross-linked fibrin, which is the major component of blood clotting. During blood clotting, thrombin activates Factor XWII, which then crosslinks fibrin at their D regions. The activity of the serine protease plasmin degrades the crosslinked fibrin, producing circulating D-dimer. SARS-CoV-2 infection has been attributed to dysregulation of blood clotting in patients, resulting in potentially lethal thrombosis, stroke, and pulmonary embolism. Circulating D-dimer has been shown to be a biomarker for COVID-19 infection severity (Yao et al. *J. Intensive Care.* (2020) 8:49). Other names: fragment D-dimer, fibrin degradation fragment.

Exemplary Lectin-Based Hemofiltration Devices

Disclosed herein are extracorporeal devices and methods of use for the treatment of viral diseases, such as a coronavirus infection, or a symptom or sequela associated with the disease, including long-term sequela that a patient may experience even after clearance of the viral infection, such as those seen in recovering COVID-19 patients. The extracorporeal devices comprise a lectin that binds to various glycoprotein-containing biological components, such as exosomes. When used for hemofiltration, the extracorporeal device with the lectin is able to filter, for example, viral particles having glycoproteins (including SARS-CoV-2 and constituent subcomponents), non-viral COVID-19 mediating nanoparticles, and circulating glycoprotein-laden exosomes.

In some embodiments, the devices, systems and methods of the invention comprise one or more hollow fiber cartridges containing an affinity agent that is a lectin, which preferably is GNA. Other lectins include NPA, Concanavalin A and cyanovirin. Examples of extracorporeal devices comprising lectins that can be used in the methods disclosed herein may be found in WO 2007/103572, WO 2009/023332, and WO 2010/065765, each of which is hereby expressly incorporated by reference in its entirety.

The extracorporeal devices disclosed herein are useful for capturing circulating viral particles comprising glycoproteins, including enveloped viral particles that, during replication, incorporate host cell membrane that include a rich set of glycoproteins and other molecules. In the case of SARS-CoV-2 and other coronaviruses, the S glycoprotein is also expressed and decorates the viral envelope.

Throughout the COVID-19 pandemic, it has become apparent that many patients may experience long-term side effects from a SARS-CoV-2 infection, or post-COVID-19 syndrome. The inflammatory process that the body undergoes to fight against the virus may lead to severe complications affecting a wide range of systemic organs. In some cases, the damage done by inflammation may be more severe than the infection itself. As shown herein, the extracorporeal devices disclosed herein are also useful in treating or inhibiting these long-term sequelae of a coronavirus infection, resulting in improved prognosis of chronic issues caused by the infection. This therapy may involve the depletion of exosomes from the patient, which may comprise one or more miRNAs that negatively impact the patient, even if the patient no longer has an active viral infection.

Accordingly, in some embodiments, the present invention relates to extracorporeal devices comprising a lectin for removing pathogenic organisms, fragments thereof, or other biological components from blood or plasma from a patient. In some embodiments, the extracorporeal device comprises one or more hollow fiber cartridges comprising the lectin. In accordance with hollow fiber membrane technology provided herein or otherwise known in the art, embodiments of the invention involves a size exclusion mechanism for subcellular nanoparticles (including but not limited to viral particles, COVID-19 mediating nanoparticles, exosomes, and the like) to contact the affinity matrix, wherein larger blood components (including cells) are restricted from passing through the pores of the hollow fibers into the extracapillary space of the device where the affinity agent resides. In some embodiments, the pore sizes range from 20-500 nanometers. In some embodiments, the pore sizes are 200 nm or about 200 nm.

By way of example, blood or plasma is run through an extracorporeal circulation circuit that uses a hollow fiber cartridge with the membranes of said hollow fibers having sufficient permeability for the subcellular nanoparticles found in the blood or plasma to be removed through the membrane of the hollow fibers and into an area outside of the fibers containing a substrate that is bound to a single or plurality of agents (e.g. lectins) capable of adhering to said subcellular nanoparticles in a manner such that said subcellular nanoparticles are attached to said agent and do not substantially re-enter the hollow fibers. Within the knowledge of one skilled in the art are available numerous types of hollow fiber systems. Selection of said hollow fiber system is dependent on the desired blood or plasma volume and rate of passage of said blood or plasma volume through the hollow fiber system. Specifically, hollow fiber cartridges may be used having lengths of 250 mm and containing 535 hollow fibers supplied by Amicon, and having the fiber dimensions: I.D. 180 micron and O.D. 360 micron, and the total contact surface area in the cartridge is 750 cm2. Alternatively, the "Plasmaflux P2" hollow fiber filter cartridge (sold by Fresenius) or Plasmart PS60 cartridges (sold by Medical srl) may be used.

Regardless of the hollow fiber system used, the concept needed for application of the present invention is that said hollow fiber filters are required to allow passage of blood cells through the interior of said hollow fiber and allow diffusion of subcellular nanoparticles to the exterior. In order to allow such diffusion, the pores on the membrane of the hollow fiber need to be of a diameter sufficient to allow particles ranging from the size of 20 nanometers to 500 nanometers in diameter, depending on the particles of interest. In some embodiments, the pores on the membrane of the hollow fiber need to be of a diameter sufficient to allow particles ranging from the size of 50 nanometers to 300 nanometers in diameter. In some embodiments, the pores on the membrane of the hollow fiber need to be of a diameter sufficient to allow particles ranging from the size of 80 nanometers to 200 nanometers in diameter. During experimentation with different hollow fibers, one skilled in the art would find it useful to utilize particles of similar size ranges as the subcellular nanoparticles in order to calibrate and quantitate the ability of various pore sizes of hollow filters. One method of performing this is through the utilization of commercially available MACS™ Beads (Milteny Biotech), which have a size of 60 nanometers. Fluorescent, spherical latex beads ranging in size from 25 to 1000 nm are also available for this purpose (e.g., from Duke Scientific (Palo Alto, Calif.)).

The substrate or matrix to be used in practicing the present invention needs to allow sufficient permeation of flow so that non-cellular blood components that enter the space exterior to the hollow fiber are distributed throughout the substrate or matrix material, so that substantial contact is made between the subcellular nanoparticles permeating the hollow fiber filter and the binding agent that is attached to the substrate or matrix. Suitable substrates or matrices are known to one skilled in the art. Said substrates or matrices include silica gel, dextran, agarose, nylon polymers, polymers of acrylic acid, co-polymers of ethylene and maleic acid anhydride, aminopropylsilica, aminocelite, glass beads, diatomaceous earth, silicate containing diatomaceous earth or other substrates or matrices known in the art. Examples of such are described in the following patents, each of which are incorporated by reference herein in their entirety: Lentz U.S. Pat. No. 4,708,713, Motomura U.S. Pat. No. 5,667,684, Takashima et al U.S. Pat. No. 5,041,079, and Porath and Janson U.S. Pat. No. 3,925,152. The agents that are attached to said substrate may be chosen based on known affinity to subcellular nanoparticles.

In some embodiments, methods of the present invention are carried out by using an affinity cartridge using the device illustrated in FIG. 1. In this device, blood or plasma is passed through the lumen of a hollow fiber ultrafiltration membrane that is in intimate contact, on the non-blood wetted side of the membrane, with immobilized lectins, which form a means to accept and immobilize viruses and other subcellular nanoparticles. Thus, the device retains intact glycoproteins (which may be a part of a larger structure) bound by lectin while allowing other components to pass through the lumen.

SARS-CoV-2 is the prototypic virus for which this invention is described, but the invention can be adapted to the removal of any coronavirus or other virus. An exemplary device, described in detail in FIGS. 1-3, includes multiple channels of hollow fiber ultrafiltration membrane that forms a filtration chamber. An inlet port and an effluent port are in communication with the filtration chamber. The ultrafiltration membrane is preferably an anisotropic membrane with the tight or retention side facing the bloodstream. The membrane is conveniently formed of any number of polymers known to the art, for example, polysulfone, polyethersulfone, polyamides, polyimides, cellulose acetate, and polyacrylamide. Preferably, the membrane has pores 200-700 nm in diameter, which will allow passage of subcellular nanoparticles, e.g., SARS-CoV-2 virions, or fragments thereof, such as SARS-CoV-2-derived glycoproteins, (e.g., SARS-CoV-2 virions of 110 nm diameter), and non-viral COVID-19 mediating nanoparticles (e.g., exosomes) but not most blood cells (red blood cells, 2,000 nm diameter, lymphocytes, 7,000-12,000 nm diameter; macrophages, 10,000-18,000 nm diameter). A diagram of an exemplary device is shown in FIG. 1. The device comprises a cartridge 10 comprising a blood-processing chamber 12 formed of suitable material such as polycarbonate 14. Around chamber 12 is an optional exterior chamber 16. A temperature controlling fluid can be circulated into chamber 16 through port 18 and out of port 20. The device includes an inlet port 32 for the blood and an outlet port 34 for the effluent. The device also provides one or more ports 48 and 50, for accessing the extra-channel space in the cartridge. As shown in FIGS. 1 and 2, chamber 12 contains a plurality of ultrafiltration membranes 22. These membranes preferably have a 0.3 mm inside diameter and 0.5 min outside diameter. FIG. 3 is a cross sectional representation of a channel 22 and shows the anisotropic nature of the membrane. As shown in FIG. 3, a hollow fiber membrane structure 40 is composed of a single polymeric material which is formed into a tubular section comprising a relatively tight ultrafiltration membrane 42 and relatively porous exterior portion 44 in which may be immobilized lectins 46. During the operation of the device, a solution containing the lectins is loaded on to the device through port 48. The lectins are allowed to immobilize to the exterior 22 of the membrane in FIG. 2. Unbound lectins can be collected from port 50 by washing with saline or other solutions. The cartridge housing is made of polycarbonate and the fibers are held in place with polyurethane potting material. The lectins are found in the extra-lumen (or extra-capillary or extra-channel) covalently bound to a solid resin material 150-300 microns (or wider) in diameter. The resin is made of a porous silicon dioxide material (SiO2), preferably diatomaceous earth. Approximately 35-45 grams of lectin bound resin is loaded into the extra-lumen space around the fibers through the polycarbonate side ports of the cartridge. During operation, blood runs along the length of the fibers and the plasma exits the pores and comes into contact with the lectin that is bound to the solid resin substrate.

For binding of lectins to the ultrafiltration membrane, the polymers of the ultrafiltration membrane are first activated, e.g., made susceptible for combining chemically with proteins, by using processes known in the art. Any number of different polymers can be used. To obtain a reactive polyacrylic acid polymer, for example, carbodiimides can be used (Valuev et al., 1998, Biomaterials, 19:41-3). Once the polymer has been activated, the lectins can be attached directly or via a linker to form in either case an affinity matrix. Suitable linkers include, but are not limited to, avidin, strepavidin, biotin, protein A, or protein G. The lectins may also be directly bound to the polymer of the ultrafiltration membrane using coupling agents such as bifunctional reagents, or may be indirectly bound. In some embodiments, GNA covalently coupled to agarose can be used to form an affinity matrix.

Accordingly, one aspect of the invention provides a lectin affinity hemodialysis cartridge, comprising: a filtration chamber configured to receive blood or plasma; a lectin, optionally coupled to agarose, diatomaceous earth, or aminocelite disposed within said filtration chamber; and a porous hollow fiber membrane, wherein said membrane has pores of 200-500 nm in diameter; wherein the lectin is selected from the group consisting of: *Galanthus nivalis* agglutinin (GNA), *Narcissus pseudonarcissus* agglutinin (NPA), cyanovirin, and Concanavalin A, and mixtures thereof wherein the cartridge is configured to remove subcellular nanoparticles from the blood or plasma.

Processes that can be used to isolate lectins such as GNA are generally known in the art. For example, Van Damme et al. demonstrate isolating the lectin from *Galantus nivalis* (snowdrop) bulbs by affinity purification with mannose or other sugars (Van Damme et al. *FEBS Letters* (1987) 215 (1):140-144). Use of purified GNA for affinity purification purposes have been previously demonstrated, such as for isolating glycoproteins like immunoglobulins (Shibuya et al. *Archives Biochem. Biophys.* (1988) 267(2):676-680). Each of the references above are hereby expressly incorporated by reference in its entirety.

The present invention also provides a device with a filtration chamber further comprises an inlet port and an outlet port; wherein a channel of said hollow fiber membrane is in fluidic communication with said inlet and said outlet ports; said cartridge having an extra-channel space within said chamber which surrounds said hollow fiber membrane; and wherein said lectin is, optionally, covalently coupled to agarose, diatomaceous earth or aminocelite that is disposed within said extra-channel space proximate to an exterior surface of said membrane.

For some methods of the present invention, blood or plasma having subcellular nanoparticles (which may or may not contain SARS-CoV-2 viral particles) is withdrawn from a patient and contacted with an ultrafiltration membrane. In some embodiments, the blood is first separated into its plasma and cellular components. The blood or plasma is then contacted with the lectins to remove the subcellular nanoparticles by binding between glycoproteins and lectins. The plasma can then be recombined with the cellular components and returned to the patient. Alternatively, the cellular components may be returned to the patient separately. The therapy can be repeated periodically until a desired response has been achieved. In some embodiments, the therapy can be carried out for 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, or 24 hours within a 24 hour period, or any amount of time within a range defined by any two of the aforementioned times. In some embodiments, the therapy can be repeated every day for 1, 2, 3, 4, 5, 6, 7, 8, 9, 10, 11, 12, 13, 14, or 15 days.

In some embodiments, the methods and devices of the present invention additionally comprise affinity agents that are monoclonal antibodies that bind to SARS-CoV-19 derived glycoproteins, such as the S1 spike protein described herein, in the extracorporeal circuit. In certain embodiments of the invention, the methods and devices of the present invention comprise a GNA affinity agent and a monoclonal antibody affinity agent.

One skilled in the art will recognize that a biological sample can be taken from, but not limited to the following bodily fluids: peripheral blood, plasma, serum, ascites, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, nasal fluid (e.g., a nasal swab isolate) stool water, urine, pancreatic juice, lavage fluids from sinus cavities, bronchopulmonary aspirates or other lavage fluids. A biological sample may also include the blastocyst cavity, umbilical cord blood, or maternal circulation that may be of fetal or maternal origin. The biological sample may also be a tissue sample or biopsy.

Methods of Therapy or Use

The present invention relates to methods for using lectins for hemofiltration of blood or plasma in an extracorporeal setting. Accordingly, the present invention provides methods for reducing subcellular nanoparticles, such as those associated with COVID-19 or a symptom or sequela thereof, from the circulatory system of an individual comprising the steps of obtaining blood or plasma from the individual, passing the blood or plasma through a porous hollow fiber membrane where lectin molecules are immobilized within the porous exterior portion of the membrane, collecting pass-through blood or plasma, and reinfusing the pass-through blood or plasma into the individual.

In some non-limiting embodiments, the devices and methods of the present invention have the ability to capture and physically remove the SARS-CoV-2 S1 (spike) protein with a high efficiency. Accordingly, the present invention provides methods for capturing and physically removing COVID-19 mediating nanoparticles from the circulatory system of an individual comprising the steps of obtaining blood or plasma from the individual, passing the blood or plasma through a porous hollow fiber membrane wherein lectin molecules are immobilized within the porous exterior portion of the membrane, collecting pass-through blood or plasma and reinfusing the pass-through blood or plasma into the individual. However, in some embodiments, the devices and methods disclosed herein can be used for a patient who no longer has an active viral infection, but still exhibits a symptom or sequela thereof.

Once a subject in need is identified, for example, a subject with severe COVID-19 disease, at risk for severe COVID-19 disease (e.g., a subject in need of oxygen therapy), or has overcome COVID-19 but still has one or more symptoms or sequelae, a method of depleting subcellular nanoparticles that may be associated with COVID-19 may include the following steps: a) providing a hollow fiber cartridge comprising a lectin or other affinity binding agent that selectively binds to the outer surfaces of the subcellular nanoparticles; b) removing a biological sample, e.g., blood or plasma, from a subject using the system, the biological sample having a concentration of the subcellular nanoparticles; c) processing the biological sample using the hollow fiber cartridge such that the affinity agents are in contact with the biological sample; d) capturing at least a portion of the subcellular nanoparticles from the biological sample such that said portion of the subcellular nanoparticles is retained in the hollow fiber cartridge; and e) reintroducing the biological sample without said portion of captured subcellular nanoparticles to the patient without removing the biological sample from the system before the biological sample is ready to be administered to the patient. Optionally, a biological sample from said subject, such as a nasal fluid (e.g., an isolate from a nasal swab), blood or plasma, from said subject is obtained before or after the therapy or both and said biological sample is analyzed for the level or amount of subcellular nanoparticles.

For use in critically-ill patients with COVID-19, the capture of SARS-CoV-2 virions from the circulatory system may have several positive benefits as follows: (1) Diminishing the systemic load of SARS-CoV-2; (2) Reducing the severity of the systemic inflammatory response (e.g., cytokine storm) occurring during the infection; (3) Improving the functions of immune cells including cells with anti-viral functions; and (4) Reduction of continuous cellular infection, progressive damage to affected organs, and/or disease-related symptoms due to the virus itself and/or the inflammatory response.

As described herein, it has demonstrated that the extracorporeal devices are able to capture exosomes from the blood or plasma from a patient. In some embodiments, the patient may have an on-going coronavirus infection, such as COVID-19. In other embodiments, the patient may no longer have an active coronavirus infection (e.g., has a reduced amount or no amount of circulating virus that is detected by conventional approaches), but the patient still exhibits a symptom or sequela of the coronavirus infection. In some embodiments, the exosomes depleted by the extracorporeal devices may comprise miR-424-5p, miR-16-2-3p, or both. These miRNAs may be involved in negative effects of the coronavirus symptom or sequela on the patient, even if the patient no longer has an active coronavirus infection.

Disclosed herein in some embodiments are methods for reducing SARS-CoV-2 virions, or portions thereof, in a COVID-19 patient in need thereof. In some embodiments, the methods comprise (a) introducing blood or plasma from a patient infected with COVID-19 into an extracorporeal device comprising a lectin (e.g., *Galanthus nivalis* agglutinin (GNA), *Narcissus pseudonarcissus* agglutinin (NPA) or *Nostoc ellipsosporum* cyanovirin) that binds to SARS-CoV-2 virions, or portions thereof; (b) contacting the blood or plasma from the patient with the lectin in the extracorporeal device for a time sufficient to allow the SARS-CoV-2 virions, or portions thereof, present in the blood or plasma, to bind to said lectin; (c) reintroducing the blood or plasma obtained after (b) into said patient, wherein the blood or plasma obtained after (b) has a reduced amount of the SARS-CoV-2 virions, or portions thereof, as compared to the blood or plasma of said patient prior to (b); and (d) optionally, detecting or identifying SARS-CoV-2 virions, or portions thereof, in a sample from said patient, such as a nasal, blood, or plasma sample, prior to (a) or after (b) or both and/or, optionally selecting or identifying a patient having COVID-19 to receive a therapy that reduces SARS-CoV-2 virions, or fragments thereof, as compared to a control level or amount (e.g., a level or amount found in a sample from healthy patient or a patient not experiencing inflammation or COVID-19 infection or a sequela associated therewith). In some embodiments, the patient does not comprise a coronavirus infection prior to step (a) but exhibits symptoms or sequela of the coronavirus infection. In some embodiments, the patient has cleared the coronavirus infection prior to step (a), but the patient still exhibits symptoms or sequela of the coronavirus infection. In some embodiments, the blood or plasma of the patient does not comprise the coronavirus prior to step (a), but the patient still exhibits symptoms or sequela of the coronavirus infection. In some embodiments, the methods further comprise determining whether the patient has early acute lung injury (ALI), early acute respiratory distress syndrome (ARDS), dyspnea, respiratory frequency ≥30 breaths/min, blood oxygen saturation ≤93%, partial pressure of arterial oxygen to fraction of inspired oxygen ratio of <300, lung infiltrates >50%, respiratory failure within 24 to 48 hours, elevated ferritin, elevated lactate, elevated lactate dehydrogenase (LDH), low absolute lymphocyte count (ALC), low platelet count, prolonged prothrombin time/international normalized ratio (PT/INR), septic shock, or multiple organ dysfunction or failure, or any combination thereof prior to (a) or after (b) or both. In some embodiments, the methods further comprise determining whether the patient has an elevated IL-6 level or amount in a blood or plasma sample, as compared to a control level or amount (e.g., a level or amount found in a blood or plasma sample from a healthy patient or a patient not experiencing inflammation or COVID-19 infection or a sequela associated therewith) either before (a) or after (b) or both. In some embodiments, the elevated serum IL-6 level is greater than equal to 2 pg/mL. In some embodiments, the methods further comprise determining whether the patient has an elevated D-dimer level or amount in a blood or plasma sample, as compared to a control level or amount (e.g., a level or amount found in a blood or plasma sample from a healthy patient or a patient not experiencing inflammation or COVID-19 infection or a sequela associated therewith) either before (a) or after (b) or both. In some embodiments, the elevated serum D-Dimer level is greater than or equal to 500 ng/mL. In some embodiments, the methods further comprise determining whether the patient has an elevated Troponin T level or amount in a blood or plasma sample, as compared to a control level or amount (e.g., a level or amount found in a blood or plasma sample from a healthy patient or a patient not experiencing inflammation or COVID-19 infection or a sequela associated therewith) either before (a) or after (b) or both. In some embodiments, the elevated serum Troponin T level is greater than or equal to 15 ng/L. In some preferred embodiments, the lectin is *Galanthus nivalis* agglutinin (GNA). In some embodiments, the extracorporeal device comprises a hollow fiber cartridge comprising the lectin and wherein the blood or plasma flows through hollow fibers of the hollow fiber cartridge. In some embodiments, the hollow fibers of the hollow fiber cartridge comprise a pore size that excludes cellular components of the blood or plasma from contacting the lectin. In some embodiments, the pore size is 20-500 nm or about 20-500 nm. In some embodiments, the pore size is 200 nm or about 200 nm. In some embodiments, the lectin is immobilized or adsorbed on to a solid support, and the hollow fiber cartridge comprises the lectin immobilized or adsorbed on the solid support. In some embodiments, the solid support comprises agarose, diatomaceous earth, or aminocelite. In some embodiments, the solid support comprises diatomaceous earth. In some embodiments, the methods further comprise isolating coronavirus virions, or portions thereof, bound to the lectin of the extracorporeal device. In some embodiments, the methods further comprise isolating exosomes associated with the coronavirus infection, or the symptom or sequela thereof, bound to the lectin of the extracorporeal device. In some embodiments, the methods further comprise determining the contents of the isolated exosomes. In some embodiments, the exosomes associated with the coronavirus infection, or the symptom or sequela thereof, comprise miR-424-5p, or miR-16-2-3p, or both. In some embodiments, the methods further comprise observing or measuring a reduction in number of coronavirus virions, or portions thereof; number of exosomes associated with the coronavirus infection, or the symptom or sequela thereof; measuring the levels or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof, in a sample of the patient's blood or plasma taken after (b) relative to a sample of the patient's blood or plasma taken before (b). In some embodiments, the methods further comprise observing an improvement in the coronavirus infection, or the symptom or sequela thereof, in the patient following (b) or (c) or both. In some embodiments, observing the improvement in the coronavirus infection, or the symptom or sequela thereof, comprises determining an improvement in early ALI, early ARDS, respiratory frequency, blood oxygen saturation, partial pressure of arterial oxygen to fraction of inspired oxygen ratio, lung infiltrates, respiratory failure, ferritin, lactate, LDH, ALC, platelet count, PT/INR, septic shock, or multiple organ dysfunction or failure, or any combination thereof, in the patient. In some embodiments, observing the improvement in the coronavirus infection, or the symptom or sequela thereof, comprises observing a reduction in number of coronavirus virions, or portions thereof; or exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a biological sample such as blood from the patient before or after the therapy or both. In some embodiments, the COVID-19 is caused by a SARS-CoV-2 variant. In some embodiments, the variant is selected from 20I/501Y.V1

(B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429). In some embodiments, the extracorporeal device is primed with an anticoagulant, preferably heparin, to prevent clotting of blood prior to (a). In some embodiments, the blood is flowed at a rate of about 50 to about 600 mL/min, preferably about 200 to about 400 mL/min through said extracorporeal device, preferably about 200 to about 240 mL/min or 200 to 240 mL/min or most preferably 240 mL/min. In some embodiments, the flow of blood is started at an initial flow rate of 100 ml/min and increased gradually to 200 ml/min (e.g., in a stepwise increase over a five-minute period). In some embodiments, reintroducing the blood back to the patient comprises flushing the extracorporeal device with saline. In some embodiments, the blood or plasma is contacted with the extracorporeal device for 0.1, 0.2, 0.3, 0.4, 0.5, 0.6, 0.7, 0.8, 0.9, 1, 2, 3, 4, 5, 6, 7, 8, 9, or 10 hours, or any amount of time within a range defined by any two of the aforementioned times. In some embodiments, steps (a), (b), (c), and optionally (d) is repeated every day for 1, 2, 3, 4, 5, 6, 7, 8, 9, 10, 11, 12, 13, 14, or 15 days. In some embodiments, the methods further comprise administering an additional antiviral therapy to the patient. In some embodiments, the additional antiviral therapy comprises administration of favipiravir, favilavir, remdesivir, tocilizumab, galidesivir, sarilumab, lopinavir, ritonavir, darunavir, ribavirin, interferon-α, pegylated interferon-α, interferon alfa-2b, convalescent serum, or any combination thereof.

Also disclosed herein some embodiments are methods for reducing COVID-19 mediating nanoparticles in a COVID-19 patient in need thereof. In some embodiments, the methods comprise (a) introducing blood or plasma from a patient infected with COVID-19 into an extracorporeal device comprising a lectin that binds to COVID-19 mediating nanoparticles (e.g., *Galanthus nivalis* agglutinin (GNA), *Narcissus pseudonarcissus* agglutinin (NPA) or *Nostoc ellipsosporum* cyanovirin); (b) contacting the blood or plasma from the patient with the lectin in the extracorporeal device for a time sufficient to allow the COVID-19 mediating nanoparticles to bind to said lectin; (c) reintroducing the blood or plasma obtained after (b) into said patient, wherein the blood or plasma obtained after (b) has a reduced amount of the COVID-19 mediating nanoparticles, as compared to the blood or plasma of said patient prior to (b); and (d) optionally, detecting or identifying SARS-CoV-2 virions, or portions thereof, or COVID-19-mediating nanoparticles in a sample from said patient, such as a nasal (e.g., obtained from a nasal swab), blood, or plasma sample, prior to (a) or after (b) or both and/or, optionally selecting or identifying a patient having COVID-19 to receive a therapy that reduces COVID-19-mediating nanoparticles, as compared to a control level or amount (e.g., a level or amount found in a sample from a healthy patient or a patient not experiencing inflammation or COVID-19 infection or a sequela associated therewith). In some embodiments, the patient does not comprise a coronavirus infection prior to step (a) but exhibits symptoms or sequela of the coronavirus infection. In some embodiments, the patient has cleared the coronavirus infection prior to step (a), but the patient still exhibits symptoms or sequela of the coronavirus infection. In some embodiments, the blood or plasma of the patient does not comprise the coronavirus prior to step (a), but the patient still exhibits symptoms or sequela of the coronavirus infection. In some embodiments, the methods further comprise determining whether the patient has early acute lung injury (ALI), early acute respiratory distress syndrome (ARDS), dyspnea, respiratory frequency ≥30 breaths/min, blood oxygen saturation ≤93%, partial pressure of arterial oxygen to fraction of inspired oxygen ratio of <300, lung infiltrates >50%, respiratory failure within 24-48 hours, elevated ferritin, elevated lactate, elevated lactate dehydrogenase (LDH), low absolute lymphocyte count (ALC), low platelet count, elevated prothrombin time/international normalized ratio (PT/INR), septic shock, or multiple organ dysfunction or failure, or any combination thereof prior to (a) or after (b) or both. In some embodiments, the methods further comprise determining whether the patient has an elevated IL-6 level or amount in a blood or plasma sample either before (a) or after (b) or both, as compared to a control level or amount (e.g., a level or amount found in a blood or plasma sample from a healthy patient or a patient not experiencing inflammation or COVID-19 infection or a sequela associated therewith). In some embodiments, the elevated serum IL-6 level is greater than equal to 2 pg/mL. In some embodiments, the methods further comprise determining whether the patient has an elevated D-dimer level or amount in a blood or plasma sample, as compared to a control level or amount (e.g., a level or amount found in a blood or plasma sample from a healthy patient or a patient not experiencing inflammation or COVID-19 infection or a sequela associated therewith) either before (a) or after (b) or both. In some embodiments, the elevated serum D-Dimer level is greater than or equal to 500 ng/mL. In some embodiments, the methods further comprise determining whether the patient has an elevated Troponin T level or amount in a blood or plasma sample, as compared to a control level or amount (e.g., a level or amount found in a blood or plasma sample from a healthy patient or a patient not experiencing inflammation or COVID-19 infection or a sequela associated therewith) either before (a) or after (b) or both. In some embodiments, the elevated serum Troponin T level is greater than or equal to 15 ng/L. In some preferred embodiments, the lectin is *Galanthus nivalis* agglutinin (GNA). In some embodiments, the extracorporeal device comprises a hollow fiber cartridge comprising the lectin and wherein the blood or plasma flows through hollow fibers of the hollow fiber cartridge. In some embodiments, the hollow fibers of the hollow fiber cartridge comprise a pore size that excludes cellular components of the blood or plasma from contacting the lectin. In some embodiments, the pore size is 20-500 nm or about 20-500 nm. In some embodiments, the pore size is 200 nm or about 200 nm. In some embodiments, the lectin is immobilized or adsorbed on to a solid support, and the hollow fiber cartridge comprises the lectin immobilized or adsorbed on the solid support. In some embodiments, the solid support comprises agarose, diatomaceous earth, or aminocelite. In some embodiments, the solid support comprises diatomaceous earth. In some embodiments, the methods further comprise isolating coronavirus virions, or portions thereof, bound to the lectin of the extracorporeal device. In some embodiments, the methods further comprise isolating exosomes associated with the coronavirus infection, or the symptom or sequela thereof, bound to the lectin of the extracorporeal device. In some embodiments, the methods further comprise determining the contents of the isolated exosomes. In some embodiments, the exosomes associated with the coronavirus infection, or the symptom or sequela thereof, comprise miR-424-5p, or miR-16-2-3p, or both. In some embodiments, the methods further comprise observing or measuring a reduction in number of coronavirus virions, or portions thereof; number of exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a biological sample such as blood or plasma from the patient before or after the therapy or both. In some embodiments, the methods further comprise observing an improvement in the coronavirus infection, or the symptom or sequela thereof, in the patient following (b) or (c) or both. In some embodiments, observing the improvement in the coronavirus infection, or the symptom or sequela thereof, comprises determining an improvement in early ALI, early ARDS, respiratory frequency, blood oxygen saturation, partial pressure of arterial oxygen to fraction of inspired oxygen ratio, lung infiltrates, respiratory failure, ferritin, lactate, LDH, ALC, platelet count, PT/INR, septic shock, or multiple organ dysfunction or failure, or any combination thereof, in the patient. In some embodiments, observing the improvement in the coronavirus infection, or the symptom or sequela thereof, comprises observing a reduction in number of coronavirus virions, or portions thereof, exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a biological sample such as blood or plasma from the patient before or after the therapy or both. In some embodiments, the COVID-19 is caused by a SARS-CoV-2 variant. In some embodiments, the variant is selected from 20I/501Y.V1 (B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429). In some embodiments, the extracorporeal device is primed with an anticoagulant, preferably heparin, to prevent clotting of blood prior to (a). In some embodiments, the blood is flowed at a rate of about 50 to about 600 mL/min, preferably about 200 to about 400 mL/min, preferably about 200 to about 240 mL/min, through said extracorporeal device. In some embodiments, the flow of blood is started at an initial flow rate of 100 ml/min and increased gradually to 200 ml/min (e.g., in a stepwise increase over a five-minute period). In some embodiments, reintroducing the blood back to the patient comprises flushing the extracorporeal device with saline. In some embodiments, the blood or plasma is contacted with the extracorporeal device for 0.1, 0.2, 0.3, 0.4, 0.5, 0.6, 0.7, 0.8, 0.9, 1, 2, 3, 4, 5, 6, 7, 8, 9, or 10 hours, or any amount of time within a range defined by any two of the aforementioned times. In some embodiments, steps (a), (b), (c), and optionally (d) is repeated every day for 1, 2, 3, 4, 5, 6, 7, 8, 9, 10, 11, 12, 13, 14, or 15 days. In some embodiments, the methods further comprise administering an additional antiviral therapy to the patient. In some embodiments, the additional antiviral therapy comprises favipiravir, favilavir, remdesivir, tocilizumab, galidesivir, sarilumab, lopinavir, ritonavir, darunavir, ribavirin, interferon-α, pegylated interferon-α, interferon alfa-2b, convalescent serum, or any combination thereof.

Also disclosed herein in some embodiments are methods for reducing exosomes comprising a COVID-19 antigen in a COVID-19 patient. In some embodiments, the methods comprise a) introducing blood or plasma from a patient infected with COVID-19 into an extracorporeal device comprising a lectin that binds to the exosomes comprising the COVID-19 antigen (e.g., *Galanthus nivalis* agglutinin (GNA), *Narcissus pseudonarcissus* agglutinin (NPA) or *Nostoc ellipsosporum* cyanovirin); (b) contacting the blood or plasma from the patient with the lectin in the extracorporeal device for a time sufficient to allow the exosomes comprising the COVID-19 antigen to bind to said lectin; (c) reintroducing the blood or plasma obtained after (b) into said patient, wherein the blood or plasma obtained after (b) has a reduced amount of the exosomes comprising the COVID-19 antigen, as compared to the blood or plasma of said patient prior to (b); and (d) optionally, detecting or identifying SARS-CoV-2 virions, or portions thereof or the exosomes comprising the COVID-19 antigen in a sample from said patient, such as a nasal, blood, or plasma sample, prior to (a) or after (b) or both and/or, optionally selecting or identifying a patient having COVID-19 to receive a therapy that reduces exosomes comprising a COVID-19 antigen, as compared to a control level or amount (e.g., a level or amount found in a blood or plasma sample from a healthy patient or a patient not experiencing inflammation or COVID-19 infection or a sequela associated therewith). In some embodiments, the patient does not comprise a coronavirus infection prior to step (a) but exhibits symptoms or sequela of the coronavirus infection. In some embodiments, the patient has cleared the coronavirus infection prior to step (a), but the patient still exhibits symptoms or sequela of the coronavirus infection. In some embodiments, the blood or plasma of the patient does not comprise the coronavirus prior to step (a), but the patient still exhibits symptoms or sequela of the coronavirus infection. In some embodiments, the methods further comprise determining whether the patient has early acute lung injury (ALI), early acute respiratory distress syndrome (ARDS), dyspnea, respiratory frequency ≥30 breaths/min, blood oxygen saturation ≤93%, partial pressure of arterial oxygen to fraction of inspired oxygen ratio of <300, lung infiltrates >50%, respiratory failure within 24-48 hours, elevated ferritin, elevated lactate, elevated lactate dehydrogenase (LDH), low absolute lymphocyte count (ALC), low platelet count, elevated prothrombin time/international normalized ratio (PT/INR), septic shock, or multiple organ dysfunction or failure, or any combination thereof prior to (a) or after (b) or both, as compared to a control level or amount (e.g., a level or amount found in a sample from a healthy patient or a patient not experiencing inflammation or COVID-19 infection or a sequela associated therewith). In some embodiments, the methods further comprise determining whether the patient has an elevated IL-6 level or amount in a blood or plasma sample, as compared to a control level or amount (e.g., a level or amount found in a blood or plasma sample from a healthy patient or a patient not experiencing inflammation or COVID-19 infection or a sequela associated therewith), either before (a) or after (b) or both. In some embodiments, the elevated serum IL-6 level is greater than equal to 2 pg/mL. In some embodiments, the methods further comprise determining whether the patient has an elevated D-dimer level or amount in a blood or plasma sample, as compared to a control level or amount (e.g., a level or amount found in a blood or plasma sample from a healthy patient or a patient not experiencing inflammation or COVID-19 infection or a sequela associated therewith), either before (a) or after (b) or both. In some embodiments, the elevated serum D-Dimer level is greater than or equal to 500 ng/mL. In some embodiments, the methods further comprise determining whether the patient has an elevated Troponin T level or amount in a blood or plasma sample, as compared to a control level or amount (e.g., a level or amount found in a blood or plasma sample from a healthy patient or a patient not experiencing inflammation or COVID-19 infection or a sequela associated therewith), either before (a) or after (b) or both. In some embodiments, the elevated serum Troponin T level is greater than or equal to 15 ng/L. In some preferred embodiments, the lectin is *Galanthus nivalis* agglutinin (GNA). In some embodiments, the extracorporeal device comprises a hollow fiber cartridge comprising the lectin and, wherein the blood or plasma flows through hollow fibers of the hollow fiber cartridge. In some embodiments, the hollow fibers of the hollow fiber cartridge comprise a pore size that excludes cellular components of the blood or plasma from contacting the lectin. In some embodiments, the pore size is 20-500 nm or about 20-500 nm. In some embodiments, the pore size is 200 nm or about 200 nm. In some embodiments, the lectin is immobilized or adsorbed on to a solid support, and the hollow fiber cartridge comprises the lectin immobilized or adsorbed on the solid support. In some embodiments, the solid support comprises agarose, diatomaceous earth, or aminocelite. In some embodiments, the solid support comprises diatomaceous earth. In some embodiments, the methods further comprise isolating coronavirus virions, or portions thereof, bound to the lectin of the extracorporeal device. In some embodiments, the methods further comprise isolating exosomes associated with the coronavirus infection, or the symptom or sequela thereof, bound to the lectin of the extracorporeal device. In some embodiments, the methods further comprise determining the contents of the isolated exosomes. In some embodiments, the exosomes associated with the coronavirus infection, or the symptom or sequela thereof, comprise miR-424-5p, or miR-16-2-3p, or both. In some embodiments, the methods further comprise observing or measuring a reduction in number of coronavirus virions, or portions thereof; number of exosomes associated with the coronavirus infection, or the symptom or sequela thereof; or measuring the level or amount of IL-1, TL-6, IL-10, IL-15, CXCL10, CCL2, Myeloperoxidase, VCAM-1, TNF alpha, C-reactive protein (CRP), D-dimer, or Troponin-T or any combination thereof in a biological sample such as blood or plasma from the patient before or after the therapy or both. In some embodiments, the methods further comprise observing an improvement in the coronavirus infection, or the symptom or sequela thereof, in the patient following (b) or (c) or both. In some embodiments, observing the improvement in the coronavirus infection, or the symptom or sequela thereof, comprises determining an improvement in early ALI, early ARDS, respiratory frequency, blood oxygen saturation, partial pressure of arterial oxygen to fraction of inspired oxygen ratio, lung infiltrates, respiratory failure, ferritin, lactate, LDH, ALC, platelet count, PT/INR, septic shock, or multiple organ dysfunction or failure, or any combination thereof, in the patient. In some embodiments, observing the improvement in the coronavirus infection, or the symptom or sequela thereof, comprises observing a reduction in number of coronavirus virions, or portions thereof; exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a biological sample such as blood or plasma from the patient before or after the therapy or both. In some embodiments, the COVID-19 is caused by a SARS-CoV-2 variant. In some embodiments, the variant is selected from 20I/501Y.V1 (B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429). In some embodiments, the extracorporeal device is primed with an anticoagulant, preferably heparin, to prevent clotting of blood prior to (a). In some embodiments, the blood is flowed at a rate of about 50 to about 600 mL/min, preferably about 200 to about 400 mL/min, more preferably about 200 to about 240 mL/min or 200 to 240 mL/min, or 240 mL/min through said extracorporeal device. In some embodiments, the flow of blood is started at an initial flow rate of 100 ml/min and increased gradually to 200 ml/min (e.g., in a stepwise increase over a five-minute period). In some embodiments, reintroducing the blood back to the patient comprises flushing the extracorporeal device with saline. In some embodiments, the blood or plasma is contacted with the extracorporeal device for 0.1, 0.2, 0.3, 0.4, 0.5, 0.6, 0.7, 0.8, 0.9, 1, 2, 3, 4, 5, 6, 7, 8, 9, or 10 hours, or any amount of time within a range defined by any two of the aforementioned times. In some embodiments, steps (a), (b), (c), and optionally (d) is repeated every day for 1, 2, 3, 4, 5, 6, 7, 8, 9, 10, 11, 12, 13, 14, or 15 days. In some embodiments, the methods further comprise administering an additional antiviral therapy to the patient. In some embodiments, the additional antiviral therapy comprises favipiravir, favilavir, remdesivir, tocilizumab, galidesivir, sarilumab, lopinavir, ritonavir, darunavir, ribavirin, interferon-α, pegylated interferon-α, interferon alfa-2b, convalescent serum, or any combination thereof.

Also disclosed herein in some embodiments are methods for reducing circulating interleukin 6 (IL-6) levels or amounts in a subject e.g., a COVID-19 patient, as compared to a healthy patient or a patient not experiencing inflammation or COVID-19 infection or a sequela associated therewith. In some embodiments, the methods comprise (a) introducing blood or plasma from a patient infected with COVID-19 into an extracorporeal device comprising a lectin (e.g., *Galanthus nivalis* agglutinin (GNA), *Narcissus pseudonarcissus* agglutinin (NPA) or *Nostoc ellipsosporum* cyanovirin) that binds to SARS-CoV-2 virions or fragments thereof or exosomes comprising a COVID-19 antigen; (b) contacting the blood or plasma from the patient with the lectin in the extracorporeal device for a time sufficient to allow the SARS-CoV-2 virions or fragments thereof or the exosomes comprising the COVID-19 antigen to bind to said lectin; (c) reintroducing the blood or plasma obtained after (b) into said patient, wherein the blood or plasma obtained after (b) has a reduced amount of the SARS-CoV-2 virions or fragments thereof, or the exosomes comprising the COVID-19 antigen, as compared to the blood or plasma of said patient prior to (b); and (d) optionally, measuring the level or amount of IL-6 in a sample from said patient, such as a blood or plasma sample, prior to (a) or after (b) or both and, optionally selecting or identifying a patient having COVID-19 to receive a therapy that reduces IL-6 levels or amount in a plasma or blood sample, as compared to a control level or amount (e.g., a level or amount found in a blood or plasma sample from a healthy patient or a patient not experiencing inflammation or COVID-19 infection or a sequela associated therewith). In some embodiments, the patient does not comprise a coronavirus infection prior to step (a) but exhibits symptoms or sequela of the coronavirus infection. In some embodiments, the patient has cleared the coronavirus infection prior to step (a), but the patient still exhibits symptoms or sequela of the coronavirus infection. In some embodiments, the blood or plasma of the patient does not comprise the coronavirus prior to step (a), but the patient still exhibits symptoms or sequela of the coronavirus infection. In some embodiments, the methods further comprise determining whether the patient has early acute lung injury (ALI), early acute respiratory distress syndrome (ARDS), dyspnea, respiratory frequency ≥30 breaths/min, blood oxygen saturation ≤93%, partial pressure of arterial oxygen to fraction of inspired oxygen ratio of <300, lung infiltrates >50%, respiratory failure within 24-48 hours, septic shock, or multiple organ dysfunction or failure, or any combination thereof prior to (a) or after (b) or both. In some embodiments, the methods further comprise determining whether the patient has an elevated IL-6 level or amount in a blood or plasma sample, as compared to a control level or amount (e.g., a level or amount found in a blood or plasma sample from a healthy patient or a patient not experiencing inflammation or COVID-19 infection or a sequela associated therewith), either before (a) or after (b) or both. In some embodiments, the elevated serum IL-6 level is greater than equal to 2 pg/mL. In some embodiments, the methods further comprise determining whether the patient has an elevated D-dimer level or amount in a blood or plasma sample, as compared to a control level or amount (e.g., a level or amount found in a blood or plasma sample from a healthy patient or a patient not experiencing inflammation or COVID-19 infection or a sequela associated therewith), either before (a) or after (b) or both. In some embodiments, the elevated serum D-Dimer level is greater than or equal to 500 mg/mL. In some embodiments, the methods further comprise determining whether the patient has an elevated Troponin T level or amount in a blood or plasma sample, as compared to a control level or amount (e.g., a level or amount found in a blood or plasma sample from a healthy patient or a patient not experiencing inflammation or COVID-19 infection or a sequela associated therewith), either before (a) or after (b) or both. In some embodiments, the elevated serum Troponin T level is greater than or equal to 15 ng/L. In some preferred embodiments, the lectin is *Galanthus nivalis* agglutinin (GNA). In some embodiments, the extracorporeal device comprises a hollow fiber cartridge comprising the lectin and wherein the blood or plasma flows through hollow fibers of the hollow fiber cartridge. In some embodiments, the hollow fibers of the hollow fiber cartridge comprise a pore size that excludes cellular components of the blood or plasma from contacting the lectin. In some embodiments, the pore size is 20-500 nm or about 20-500 nm. In some embodiments, the pore size is 200 nm or about 200 nm. In some embodiments, the lectin is immobilized or adsorbed on to a solid support, and the hollow fiber cartridge comprises the lectin immobilized or adsorbed on the solid support. In some embodiments, the solid support comprises agarose, diatomaceous earth, or aminocelite. In some embodiments, the solid support comprises diatomaceous earth. In some embodiments, the methods further comprise isolating coronavirus virions, or portions thereof, bound to the lectin of the extracorporeal device. In some embodiments, the methods further comprise isolating exosomes associated with the coronavirus infection, or the symptom or sequela thereof, bound to the lectin of the extracorporeal device. In some embodiments, the methods further comprise determining the contents of the isolated exosomes. In some embodiments, the exosomes associated with the coronavirus infection, or the symptom or sequela thereof, comprises miR-424-5p, or miR-16-2-3p, or both. In some embodiments, the methods further comprise observing or measuring a reduction in number of coronavirus virions, or portions thereof-; number of exosomes associated with the coronavirus infection, or the symptom or sequela thereof, or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a biological sample such as blood from the patient before or after the therapy or both. In some embodiments, the methods further comprise observing an improvement in the coronavirus infection, or the symptom or sequela thereof, in the patient following (b) or (c) or both. In some embodiments, observing the improvement in the coronavirus infection, or the symptom or sequela thereof, comprises determining an improvement in early ALI, early ARDS, respiratory frequency, blood oxygen saturation, partial pressure of arterial oxygen to fraction of inspired oxygen ratio, lung infiltrates, respiratory failure, septic shock, or multiple organ dysfunction or failure, or any combination thereof, in the patient. In some embodiments, observing the improvement in the coronavirus infection, or the symptom or sequela thereof, comprises observing a reduction in number of coronavirus virions, or portions thereof; exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a biological sample such as blood or plasma from the patient before or after the therapy or both. In some embodiments, the COVID-19 is caused by a SARS-CoV-2 variant. In some embodiments, the variant is selected from 20I/501Y.V1 (B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429). In some embodiments, the extracorporeal device is primed with an anticoagulant, preferably heparin, to prevent clotting of blood prior to (a). In some embodiments, the blood is flowed at a rate of about 50 to about 600 mL/min, preferably about 200 to about 400 mL/min or 200 to 240 mL/min or most preferably 240 mL/min through said extracorporeal device. In some embodiments, the flow of blood is started at an initial flow rate of 100 ml/min and increased gradually to 200 ml/min (e.g., in a stepwise increase over a five-minute period). In some embodiments, reintroducing the blood back to the patient comprises flushing the extracorporeal device with saline. In some embodiments, the blood or plasma is contacted with the extracorporeal device for 0.1, 0.2, 0.3, 0.4, 0.5, 0.6, 0.7, 0.8, 0.9, 1, 2, 3, 4, 5, 6, 7, 8, 9, or 10 hours, or any amount of time within a range defined by any two of the aforementioned times. In some embodiments, steps (a), (b), (c), and optionally (d) is repeated every day for 1, 2, 3, 4, 5, 6, 7, 8, 9, 10, 11, 12, 13, 14, or 15 days. In some embodiments, the methods further comprise administering an additional antiviral therapy to the patient. In some embodiments, the additional antiviral therapy comprises favipiravir, favilavir, remdesivir, tocilizumab, galidesivir, sarilumab, lopinavir, ritonavir, darunavir, ribavirin, interferon-α, pegylated interferon-α, interferon alfa-2b, convalescent serum, or any combination thereof.

Also disclosed herein in some embodiments are methods for reducing the level or amount of circulating D-dimer in a subject e.g., a COVID-19 patient, as compared to a healthy patient or a patient not experiencing inflammation or COVID-19 infection or a sequela associated therewith. In some embodiments, the methods comprise (a) introducing blood or plasma from a patient infected with COVID-19 into an extracorporeal device comprising a lectin (e.g., *Galanthus nivalis* agglutinin (GNA), *Narcissus pseudonarcissus* agglutinin (NPA) or *Nostoc ellipsosporum* cyanovirin) that binds to SARS-CoV-2 virions or fragments thereof or exosomes comprising a COVID-19 antigen; (b) contacting the blood or plasma from the patient with the lectin in the extracorporeal device for a time sufficient to allow the SARS-CoV-2 virions or fragments thereof or the exosomes comprising the COVID-19 antigen to bind to said lectin; (c) reintroducing the blood or plasma obtained after (b) into said patient, wherein the blood or plasma obtained after (b) has a reduced amount of the SARS-CoV-2 virions or fragments thereof or the exosomes comprising the COVID-19 antigen, as compared to the blood or plasma of said patient prior to (b); and (d) optionally, measuring the level or amount of D-dimer in a sample from said patient, such as a blood or plasma sample, prior to (a) or after (b) or both and, optionally selecting or identifying a patient having COVID-19 to receive a therapy that reduces the level or amount of D-dimer in a blood or plasma sample, as compared to a control level or amount (e.g., a level or amount found in a blood or plasma sample from a healthy patient or a patient not experiencing inflammation or COVID-19 infection or a sequela associated therewith). In some embodiments, the patient does not comprise a coronavirus infection prior to step (a) but exhibits symptoms or sequela of the coronavirus infection. In some embodiments, the patient has cleared the coronavirus infection prior to step (a), but the patient still exhibits symptoms or sequela of the coronavirus infection. In some embodiments, the blood or plasma of the patient does not comprise the coronavirus prior to step (a), but the patient still exhibits symptoms or sequela of the coronavirus infection. In some embodiments, the methods further comprise determining whether the patient has early acute lung injury (ALI), early acute respiratory distress syndrome (ARDS), dyspnea, respiratory frequency ≥30 breaths/min, blood oxygen saturation ≤93%, partial pressure of arterial oxygen to fraction of inspired oxygen ratio of <300, lung infiltrates >50%, respiratory failure within 24-48 hours, elevated ferritin, elevated lactate, elevated lactate dehydrogenase (LDH), low absolute lymphocyte count (ALC), low platelet count, elevated prothrombin time/international normalized ratio (PT/INR), septic shock, or multiple organ dysfunction or failure, or any combination thereof prior to (a) or after (b) or both. In some embodiments, the methods further comprise determining whether the patient has an elevated IL-6 level or amount in a blood or plasma sample, as compared to a control level or amount (e.g., a level or amount found in a blood or plasma sample from a healthy patient or a patient not experiencing inflammation or COVID-19 infection or a sequela associated therewith) either before (a) or after (b) or both. In some embodiments, the elevated serum IL-6 level is greater than equal to 2 pg/mL. In some embodiments, the methods further comprise determining whether the patient has an elevated D-dimer level or amount in a blood or plasma sample, as compared to a control level or amount (e.g., a level or amount found in a blood or plasma sample from a healthy patient or a patient not experiencing inflammation or COVID-19 infection or a sequela associated therewith) either before (a) or after (b) or both. In some embodiments, the elevated serum D-Dimer level is greater than or equal to 500 ng/mL. In some embodiments, the methods further comprise determining whether the patient has an elevated Troponin T level or amount in a blood or plasma sample, as compared to a control level or amount (e.g., a level or amount found in a blood or plasma sample from a healthy patient or a patient not experiencing inflammation or COVID-19 infection or a sequela associated therewith) either before (a) or after (b) or both. In some embodiments, the elevated serum Troponin T level is greater than or equal to 15 ng/L. In some preferred embodiments, the lectin is *Galanthus nivalis* agglutinin (GNA). In some embodiments, the extracorporeal device comprises a hollow fiber cartridge comprising the lectin and wherein the blood or plasma flows through hollow fibers of the hollow fiber cartridge. In some embodiments, the hollow fibers of the hollow fiber cartridge comprise a pore size that excludes cellular components of the blood or plasma from contacting the lectin. In some embodiments, the pore size is 20-500 nm or about 20-500 nm. In some embodiments, the pore size is 200 nm or about 200 nm. In some embodiments, the lectin is immobilized or adsorbed on to a solid support, and the hollow fiber cartridge comprises the lectin immobilized or adsorbed on the solid support. In some embodiments, the solid support comprises agarose, diatomaceous earth, or aminocelite. In some embodiments, the solid support comprises diatomaceous earth. In some embodiments, the methods further comprise isolating coronavirus virions, or portions thereof, bound to the lectin of the extracorporeal device. In some embodiments, the methods further comprise isolating exosomes associated with the coronavirus infection, or the symptom or sequela thereof, bound to the lectin of the extracorporeal device. In some embodiments, the methods further comprise determining the contents of the isolated exosomes. In some embodiments, the exosomes associated with the coronavirus infection, or the symptom or sequela thereof, comprises miR-424-5p, or miR-16-2-3p, or both. In some embodiments, the methods further comprise observing or measuring a reduction in number of coronavirus virions, or portions thereof; number of exosomes associated with the coronavirus infection, or the symptom or sequela thereof, or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a biological sample such as blood from the patient before or after the therapy or both. In some embodiments, the methods further comprise observing an improvement in the coronavirus infection, or the symptom or sequela thereof, in the patient following (b) or (c) or both. In some embodiments, observing the improvement in the coronavirus infection, or the symptom or sequela thereof, comprises determining an improvement in early ALI, early ARDS, respiratory frequency, blood oxygen saturation, partial pressure of arterial oxygen to fraction of inspired oxygen ratio, lung infiltrates, respiratory failure, ferritin, lactate, LDH, ALC, platelet count, PT/INR, septic shock, or multiple organ dysfunction or failure, or any combination thereof, in the patient. In some embodiments, observing the improvement in the coronavirus infection, or the symptom or sequela thereof, comprises observing a reduction in number of coronavirus virions, or portions thereof; exosomes associated with the coronavirus infection, or the symptom or sequela thereof, or measuring the level or amount of IL-1, TL-6, IL-10, IL-15, CXCL10, CCL2, Myeloperoxidase, VCAM-1, TNF alpha, C-reactive protein (CRP), D-dimer, or Troponin-T or any combination thereof in a biological sample such as blood from the patient before or after the therapy or both. In some embodiments, the COVID-19 is caused by a SARS-CoV-2 variant. In some embodiments, the variant is selected from 20I/501Y.V1 (B.1.1.7), 20H/501 Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429). In some embodiments, the extracorporeal device is primed with an anticoagulant, preferably heparin, to prevent clotting of blood prior to (a). In some embodiments, the blood is flowed at a rate of about 50 to about 600 mL/min, preferably about 200 to about 400 mL/min, preferably about 200 to about 240 mL/min or 200 to 240 mL/min, most preferably 240 mL/min, through said extracorporeal device. In some embodiments, the flow of blood is started at an initial flow rate of 100 ml/min and increased gradually to 200 mL/min (e.g., in a stepwise increase over a five-minute period). In some embodiments, reintroducing the blood back to the patient comprises flushing the extracorporeal device with saline. In some embodiments, the blood or plasma is contacted with the extracorporeal device for 0.1, 0.2, 0.3, 0.4, 0.5, 0.6, 0.7, 0.8, 0.9, 1, 2, 3, 4, 5, 6, 7, 8, 9, or 10 hours, or any amount of time within a range defined by any two of the aforementioned times. In some embodiments, steps (a), (b), (c), and optionally (d) is repeated every day for 1, 2, 3, 4, 5, 6, 7, 8, 9, 10, 11, 12, 13, 14, or 15 days. In some embodiments, the methods further comprise administering an additional antiviral therapy to the patient. In some embodiments, the additional antiviral therapy comprises favipiravir, favilavir, remdesivir, tocilizumab, galidesivir, sarilumab, lopinavir, ritonavir, darunavir, ribavirin, interferon-α, pegylated interferon-α, interferon alfa-2b, convalescent serum, or any combination thereof.

Also disclosed herein in some embodiments are methods for reducing the level or amount of circulating Troponin T in a COVID-19 patient, as compared to a healthy patient or a patient not experiencing inflammation or COVID-19 infection or a sequela associated therewith. In some embodiments, the methods comprise (a) introducing blood or plasma from a patient infected with COVID-19 into an extracorporeal device comprising a lectin (e.g., *Galanthus nivalis* agglutinin (GNA), *Narcissus pseudonarcissus* agglutinin (NPA) or *Nostoc ellipsosporum* cyanovirin) that binds to SARS-CoV-2 virions or fragments thereof or exosomes comprising a COVID-19 antigen; (b) contacting the blood or plasma from the patient with the lectin in the extracorporeal device for a time sufficient to allow the SARS-CoV-2 virions or fragments thereof or the exosomes comprising the COVID-19 antigen to bind to said lectin; (c) reintroducing the blood or plasma obtained after (b) into said patient, wherein the blood or plasma obtained after (b) has a reduced amount of the SARS-CoV-2 virions or fragments thereof or the exosomes comprising the COVID-19 antigen, as compared to the blood or plasma of said patient prior to (b); and (d) optionally, measuring the level or amount of Troponin T in a sample from said patient, such as a blood or plasma sample, prior to (a) or after (b) or both and, optionally selecting or identifying a patient having COVID-19 to receive a therapy that reduces Troponin T levels or amount in a blood or plasma sample, as compared to a control level or amount (e.g., a level or amount found in a blood or plasma sample from a healthy patient or a patient not experiencing inflammation or COVID-19 infection or a sequela associated therewith). In some embodiments, the patient does not comprise a coronavirus infection prior to step (a) but exhibits symptoms or sequela of the coronavirus infection. In some embodiments, the patient has cleared the coronavirus infection prior to step (a), but the patient still exhibits symptoms or sequela of the coronavirus infection. In some embodiments, the blood or plasma of the patient does not comprise the coronavirus prior to step (a), but the patient still exhibits symptoms or sequela of the coronavirus infection. In some embodiments, the methods further comprise determining whether the patient has early acute lung injury (ALI), early acute respiratory distress syndrome (ARDS), dyspnea, respiratory frequency ≥30 breaths/min, blood oxygen saturation ≤93%, partial pressure of arterial oxygen to fraction of inspired oxygen ratio of <300, lung infiltrates >50%, respiratory failure within 24-48 hours, septic shock, or multiple organ dysfunction or failure, or any combination thereof prior to (a) or after (b) or both. In some embodiments, the methods further comprise determining whether the patient has an elevated IL-6 level or amount in a blood or plasma sample either before (a) or after (b) or both, as compared to a control level or amount (e.g., a level or amount found in a blood or plasma sample from a healthy patient or a patient not experiencing inflammation or COVID-19 infection or a sequela associated therewith). In some embodiments, the elevated serum IL-6 level is greater than equal to 2 pg/mL. In some embodiments, the methods further comprise determining whether the patient has an elevated D-dimer level or amount in a blood or plasma sample either before (a) or after (b) or both. In some embodiments, the elevated serum D-Dimer level is greater than or equal to 500 ng/mL. In some embodiments, the methods further comprise determining whether the patient has an elevated Troponin T level or amount in a blood or plasma sample either before (a) or after (b) or both. In some embodiments, the elevated serum Troponin T level is greater than or equal to 15 ng/L. In some preferred embodiments, the lectin is *Galanthus nivalis* agglutinin (GNA). In some embodiments, the extracorporeal device comprises a hollow fiber cartridge comprising the lectin and wherein the blood or plasma flows through hollow fibers of the hollow fiber cartridge. In some embodiments, the hollow fibers of the hollow fiber cartridge comprise a pore size that excludes cellular components of the blood or plasma from contacting the lectin. In some embodiments, the pore size is 20-500 nm or about 20-500 nm. In some embodiments, the pore size is 200 nm or about 200 nm. In some embodiments, the lectin is immobilized or adsorbed on to a solid support, and the hollow fiber cartridge comprises the lectin immobilized or adsorbed on the solid support. In some embodiments, the solid support comprises agarose, diatomaceous earth, or aminocelite. In some embodiments, the solid support comprises diatomaceous earth. In some embodiments, the methods further comprise isolating coronavirus virions, or portions thereof, bound to the lectin of the extracorporeal device. In some embodiments, the methods further comprise isolating exosomes associated with the coronavirus infection, or the symptom or sequela thereof, bound to the lectin of the extracorporeal device. In some embodiments, the methods further comprise determining the contents of the isolated exosomes. In some embodiments, the exosomes associated with the coronavirus infection, or the symptom or sequela thereof, comprises miR-424-5p, or miR-16-2-3p or both. In some embodiments, the methods further comprise observing or measuring a reduction in number of coronavirus virions, or portions thereof; number of exosomes associated with the coronavirus infection, or the symptom or sequela thereof or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a biological sample such as blood or plasma from the patient before or after the therapy or both. In some embodiments, the methods further comprise observing an improvement in the coronavirus infection, or the symptom or sequela thereof, in the patient following (b) or (c) or both. In some embodiments, observing the improvement in the coronavirus infection, or the symptom or sequela thereof, comprises determining an improvement in early ALI, early ARDS, respiratory frequency, blood oxygen saturation, partial pressure of arterial oxygen to fraction of inspired oxygen ratio, lung infiltrates, respiratory failure, septic shock, or multiple organ dysfunction or failure, or any combination thereof, in the patient. In some embodiments, observing the improvement in the coronavirus infection, or the symptom or sequela thereof, comprises observing a reduction in number of coronavirus virions, or portions thereof; exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a biological sample such as blood or plasma from the patient before or after the therapy or both. In some embodiments, the COVID-19 is caused by a SARS-CoV-2 variant. In some embodiments, the variant is selected from 20I/501Y.V1 (B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429). In some embodiments, the extracorporeal device is primed with an anticoagulant, preferably heparin, to prevent clotting of blood prior to (a). In some embodiments, the blood is flowed at a rate of about 50 to about 600 mL/min, preferably about 200 to about 400 mL/min or 200 mL/min to 240 mL/min, most preferably 240 mL/min through said extracorporeal device. In some embodiments, the flow of blood is started at an initial flow rate of 100 ml/min and increased gradually to 200 mL/min (e.g., in a stepwise increase over a five-minute period). In some embodiments, reintroducing the blood back to the patient comprises flushing the extracorporeal device with saline. In some embodiments, the blood or plasma is contacted with the extracorporeal device for 0.1, 0.2, 0.3, 0.4, 0.5, 0.6, 0.7, 0.8, 0.9, 1, 2, 3, 4, 5, 6, 7, 8, 9, or 10 hours, or any amount of time within a range defined by any two of the aforementioned times. In some embodiments, steps (a), (b), (c), and optionally (d) is repeated every day for 1, 2, 3, 4, 5, 6, 7, 8, 9, 10, 11, 12, 13, 14, or 15 days. In some embodiments, the methods further comprise administering an additional antiviral therapy to the patient. In some embodiments, the additional antiviral therapy comprises favipiravir, favilavir, remdesivir, tocilizumab, galidesivir, sarilumab, lopinavir, ritonavir, darunavir, ribavirin, interferon-α, pegylated interferon-α, interferon alfa-2b, convalescent serum, or any combination thereof.

Also disclosed herein in some embodiments are methods for treating or inhibiting a coronavirus infection, or a symptom or sequela thereof, in a patient in need thereof. In some embodiments, the methods comprise (a) introducing blood or plasma comprising coronavirus or a portion thereof from a patient having a coronavirus infection, or a symptom or sequela thereof, into an extracorporeal device comprising a lectin that binds to said coronavirus or a portion thereof (e.g., *Galanthus nivalis* agglutinin (GNA), *Narcissus pseudonarcissus* agglutinin (NPA) or *Nostoc ellipsosporum* cyanovirin); (b) contacting the blood or plasma from the patient with the lectin in the extracorporeal device for a time sufficient to allow the coronavirus or a portion thereof present in the blood or plasma, to bind to said lectin; (c) reintroducing the blood or plasma obtained after (b) into said patient, wherein the blood or plasma obtained after (b) has a reduced amount of the coronavirus, or portion thereof, as compared to the blood or plasma of said patient prior to (b); and (d) optionally, detecting or identifying the coronavirus or portions thereof in a sample from said patient, such as a nasal (e.g., a nasal swab isolate), blood or plasma sample, prior to (a) or after (b) or both and/or, optionally selecting or identifying a patient having a coronavirus infection, or a symptom or sequela, thereof to receive a therapy that reduces said coronavirus or a portion thereof. In some embodiments, the patient does not comprise a coronavirus infection prior to step (a) but exhibits symptoms or sequela of the coronavirus infection. In some embodiments, the patient has cleared the coronavirus infection prior to step (a), but the patient still exhibits symptoms or sequela of the coronavirus infection. In some embodiments, the blood or plasma of the patient does not comprise the coronavirus prior to step (a), but the patient still exhibits symptoms or sequela of the coronavirus infection. In some embodiments, the methods further comprise determining whether the patient has early acute lung injury (ALI), early acute respiratory distress syndrome (ARDS), dyspnea, respiratory frequency ≥30 breaths/min, blood oxygen saturation ≤93%, partial pressure of arterial oxygen to fraction of inspired oxygen ratio of <300, lung infiltrates >50%, respiratory failure within 24-48 hours, elevated ferritin, elevated lactate, elevated lactate dehydrogenase (LDH), low absolute lymphocyte count (ALC), low platelet count, elevated prothrombin time/international normalized ratio (PT/INR), septic shock, or multiple organ dysfunction or failure, or any combination thereof prior to (a) or after (b) or both. In some embodiments, the methods further comprise determining whether the patient has an elevated IL-6 level or amount in a blood or plasma sample either before (a) or after (b) or both, as compared to a control level or amount (e.g., a level or amount found in a blood or plasma sample from a healthy patient or a patient not experiencing inflammation or COVID-19 infection or a sequela associated therewith). In some embodiments, the elevated serum IL-6 level is greater than equal to 2 pg/mL. In some embodiments, the methods further comprise determining whether the patient has an elevated serum D-dimer level or amount in a blood or plasma sample either before (a) or after (b) or both, as compared to a control level or amount (e.g., a level or amount found in a blood or plasma sample from a healthy patient or a patient not experiencing inflammation or COVID-19 infection or a sequela associated therewith). In some embodiments, the elevated serum D-Dimer level is greater than or equal to 500 ng/mL. In some embodiments, the methods further comprise determining whether the patient has an elevated Troponin T level or amount in a blood or plasma sample either before (a) or after (b) or both, as compared to a control level or amount (e.g., a level or amount found in a blood or plasma sample from a healthy patient or a patient not experiencing inflammation or COVID-19 infection or a sequela associated therewith). In some embodiments, the elevated serum Troponin T level is greater than or equal to 15 ng/L. In some preferred embodiments, the lectin is *Galanthus nivalis* agglutinin (GNA). In some embodiments, the extracorporeal device comprises a hollow fiber cartridge comprising the lectin and wherein the blood or plasma flows through hollow fibers of the hollow fiber cartridge. In some embodiments, the hollow fibers of the hollow fiber cartridge comprise a pore size that excludes cellular components of the blood or plasma from contacting the lectin. In some embodiments, the pore size is 20-500 nm or about 20-500 nm. In some embodiments, the pore size is 200 nm or about 200 nm. In some embodiments, the lectin is immobilized or adsorbed on to a solid support, and the hollow fiber cartridge comprises the lectin immobilized or adsorbed on the solid support. In some embodiments, the solid support comprises agarose, diatomaceous earth, or aminocelite. In some embodiments, the solid support comprises diatomaceous earth. In some embodiments, the methods further comprise isolating coronavirus virions, or portions thereof, bound to the lectin of the extracorporeal device. In some embodiments, the methods further comprise isolating exosomes associated with the coronavirus infection, or the symptom or sequela thereof, bound to the lectin of the extracorporeal device. In some embodiments, the methods further comprise determining the contents of the isolated exosomes. In some embodiments, the exosomes associated with the coronavirus infection, or the symptom or sequela thereof, comprises miR-424-5p, or miR-16-2-3p, or both. In some embodiments, the methods further comprise observing or measuring a reduction in number of coronavirus virions, or portions thereof; number of exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof, in a sample of the patient's blood or plasma taken after (b) relative to a sample of the patient's blood or plasma taken before (b). In some embodiments, the methods further comprise observing an improvement in the coronavirus infection, or the symptom or sequela thereof, in the patient following (b) or (c) or both, as compared to a control level or amount (e.g., a level or amount found in a blood or plasma sample from a healthy patient or a patient not experiencing inflammation or COVID-19 infection or a sequela associated therewith). In some embodiments, observing the improvement in the coronavirus infection, or the symptom or sequela thereof, comprises determining an improvement in early ALI, early ARDS, respiratory frequency, blood oxygen saturation, partial pressure of arterial oxygen to fraction of inspired oxygen ratio, lung infiltrates, respiratory failure, ferritin, lactate, LDH, ALC, platelet count, PT/INR, septic shock, or multiple organ dysfunction or failure, or any combination thereof, in the patient. In some embodiments, observing the improvement in the coronavirus infection, or the symptom or sequela thereof, comprises observing a reduction in number of coronavirus virions, or portions thereof; exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a biological sample such as blood or plasma from the patient before or after the therapy or both. In some embodiments, the coronavirus infection is caused by a coronavirus selected from SARS-CoV-2, SARS-CoV-1, MERS-CoV, HCoV-229E, HCoV-OC43, HCoV NL63, or HCoV-HKU1. In some embodiments, the SARS-CoV-2 is a SARS-CoV-2 variant. In some embodiments, the variant is selected from 20I/501Y.V1 (B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429). In some embodiments, the extracorporeal device is primed with an anticoagulant, preferably heparin, to prevent clotting of blood prior to (a). In some embodiments, the blood is flowed at a rate of about 50 to about 600 mL/min, preferably about 200 to about 400 mL/min, preferably about 200 to about 240 mL/min or 200 mL/min to 240 mL/min, most preferably 240 mL/min, through said extracorporeal device. In some embodiments, reintroducing the blood back to the patient comprises flushing the extracorporeal device with saline. In some embodiments, the blood or plasma is contacted with the extracorporeal device for 0.1, 0.2, 0.3, 0.4, 0.5, 0.6, 0.7, 0.8, 0.9, 1, 2, 3, 4, 5, 6, 7, 8, 9, or 10 hours, or any amount of time within a range defined by any two of the aforementioned times. In some embodiments, steps (a), (b), (c), and optionally (d) is repeated every day for 1, 2, 3, 4, 5, 6, 7, 8, 9, 10, 11, 12, 13, 14, or 15 days. In some embodiments, the methods further comprise administering an additional antiviral therapy to the patient. In some embodiments, the additional antiviral therapy comprises favipiravir, favilavir, remdesivir, tocilizumab, galidesivir, sarilumab, lopinavir, ritonavir, darunavir, ribavirin, interferon-α, pegylated interferon-α, interferon alfa-2b, convalescent serum, or any combination thereof.

Also disclosed herein in some embodiments are methods for treating or inhibiting a coronavirus infection, or a symptom or sequela thereof, in a patient in need thereof. In some embodiments, the methods comprise (a) introducing blood or plasma comprising exosomes associated with the coronavirus infection, or the symptom or sequela thereof, from a patient having a coronavirus infection, or a symptom or sequela thereof, into an extracorporeal device comprising a lectin that binds to said exosomes; (b) contacting the blood or plasma from the patient with the lectin in the extracorporeal device for a time sufficient to allow the exosomes present in the blood or plasma to bind to said lectin; (c) reintroducing the blood or plasma obtained after (b) into said patient, wherein the blood or plasma obtained after (b) has a reduced amount of the exosomes as compared to the blood or plasma of said patient prior to (b): and (d) optionally, detecting or identifying the exosomes in a sample from said patient, such as a nasal (e.g., isolated from a nasal swab), blood or plasma sample, prior to (a) or after (b) or both and/or, optionally selecting or identifying a patient having a coronavirus infection, or a symptom or sequela thereof, to receive a therapy that reduces said exosomes. In some embodiments, the patient does not comprise a coronavirus infection prior to step (a) but exhibits symptoms or sequela of the coronavirus infection. In some embodiments, the patient has cleared the coronavirus infection prior to step (a), but the patient still exhibits symptoms or sequela of the coronavirus infection. In some embodiments, the blood or plasma of the patient does not comprise the coronavirus prior to step (a), but the patient still exhibits symptoms or sequela of the coronavirus infection. In some embodiments, the methods further comprise determining whether the patient has early acute lung injury (ALI), early acute respiratory distress syndrome (ARDS), dyspnea, respiratory frequency ≥30 breaths/min, blood oxygen saturation ≤93%, partial pressure of arterial oxygen to fraction of inspired oxygen ratio of <300, lung infiltrates >50%, respiratory failure, elevated ferritin, elevated lactate, elevated lactate dehydrogenase (LDH), low absolute lymphocyte count (ALC), low platelet count, elevated prothrombin time/international normalized ratio (PT/INR), septic shock, or multiple organ dysfunction or failure, or any combination thereof prior to (a) or after (b) or both. In some embodiments, the methods further comprise determining whether the patient has an elevated IL-6 level or amount in a blood or plasma sample either before (a) or after (b) or both, as compared to a control level or amount (e.g., a level or amount found in a blood or plasma sample from a healthy patient or a patient not experiencing inflammation or COVID-19 infection or a sequela associated therewith). In some embodiments, the elevated serum IL-6 level is greater than equal to 2 pg/mL. In some embodiments, the methods further comprise determining whether the patient has an elevated D-dimer level or amount in a blood or plasma sample either before (a) or after (b) or both, as compared to a control level or amount (e.g., a level or amount found in a blood or plasma sample from a healthy patient or a patient not experiencing inflammation or COVID-19 infection or a sequela associated therewith). In some embodiments, the elevated serum D-Dimer level is greater than or equal to 500 ng/mL. In some embodiments, the methods further comprise determining whether the patient has an elevated Troponin T level or amount in a blood or plasma sample either before (a) or after (b) or both, as compared to a control level or amount (e.g., a level or amount found in a blood or plasma sample from a healthy patient or a patient not experiencing inflammation or COVID-19 infection or a sequela associated therewith). In some embodiments, the elevated serum Troponin T level is greater than or equal to 15 ng/L. In some preferred embodiments, the lectin is *Galanthus nivalis* agglutinin (GNA). In some embodiments, the extracorporeal device comprises a hollow fiber cartridge comprising the lectin and wherein the blood or plasma flows through hollow fibers of the hollow fiber cartridge. In some embodiments, the hollow fibers of the hollow fiber cartridge comprise a pore size that excludes cellular components of the blood or plasma from contacting the lectin. In some embodiments, the pore size is 20-500 nm or about 20-500 nm. In some embodiments, the pore size is 200 nm or about 200 nm. In some embodiments, the lectin is immobilized or adsorbed on to a solid support, and the hollow fiber cartridge comprises the lectin immobilized or adsorbed on the solid support. In some embodiments, the solid support comprises agarose, diatomaceous earth, or aminocelite. In some embodiments, the solid support comprises diatomaceous earth. In some embodiments, the methods further comprise isolating coronavirus virions, or portions thereof, bound to the lectin of the extracorporeal device. In some embodiments, the methods further comprise isolating exosomes associated with the coronavirus infection, or the symptom or sequela thereof, bound to the lectin of the extracorporeal device. In some embodiments, the methods further comprise determining the contents of the isolated exosomes. In some embodiments, the exosomes associated with the coronavirus infection, or the symptom or sequela thereof, comprises miR-424-5p, or miR-16-2-3p, or both. In some embodiments, the methods further comprise observing or measuring a reduction in number of coronavirus virions, or portions thereof; number of exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T, or any combination thereof, in a sample of the patient's blood or plasma taken after (b) relative to a sample of the patient's blood taken before (b). In some embodiments, the methods further comprise observing an improvement in the coronavirus infection, or the symptom or sequela thereof, in the patient following (b) or (c) or both. In some embodiments, observing the improvement in the coronavirus infection, or the symptom or sequela thereof, comprises determining an improvement in early ALI, early ARDS, respiratory frequency, blood oxygen saturation, partial pressure of arterial oxygen to fraction of inspired oxygen ratio, lung infiltrates, respiratory failure, ferritin, lactate, LDH, ALC, platelet count. PT/INR, septic shock, or multiple organ dysfunction or failure, or any combination thereof, in the patient. In some embodiments, observing the improvement in the coronavirus infection, or the symptom or sequela thereof, comprises observing a reduction in number of coronavirus virions, or portions thereof; exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T, or any combination thereof in the patient relative to before the treatment. In some embodiments, the coronavirus infection is caused by a coronavirus selected from SARS-CoV-2, SARS-CoV-1, MERS-CoV, HCoV-229E, HCoV-OC43, HCoV NL63, or HCoV-HKU1. In some embodiments, the SARS-CoV-2 is a SARS-CoV-2 variant. In some embodiments, the variant is selected from 20I/501Y.V1 (B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429). In some embodiments, the extracorporeal device is primed with an anticoagulant, preferably heparin, to prevent clotting of blood prior to (a). In some embodiments, the blood is flowed at a rate of about 50 to about 600 mL/min, preferably about 200 to about 400 mL/min, preferably about 200 to about 240 mL/min or 20 mL/min to 240 mL/min, most preferably 240 mL/min, through said extracorporeal device. In some embodiments, reintroducing the blood back to the patient comprises flushing the extracorporeal device with saline. In some embodiments, the blood or plasma is contacted with the extracorporeal device for 0.1, 0.2, 0.3, 0.4, 0.5, 0.6, 0.7, 0.8, 0.9, 1, 2, 3, 4, 5, 6, 7, 8, 9, or 10 hours, or any amount of time within a range defined by any two of the aforementioned times. In some embodiments, steps (a), (b), (c), and optionally (d) is repeated every day for 1, 2, 3, 4, 5, 6, 7, 8, 9, 10, 11, 12, 13, 14, or 15 days. In some embodiments, the methods further comprise administering an additional antiviral therapy to the patient. In some embodiments, the additional antiviral therapy comprises favipiravir, favilavir, remdesivir, tocilizumab, galidesivir, sarilumab, lopinavir, ritonavir, darunavir, ribavirin, interferon-α, pegylated interferon-α, interferon alfa-2b, convalescent serum, or any combination thereof.

Also disclosed herein in some embodiments are methods for treating or inhibiting a coronavirus infection, or a symptom or sequela thereof, in a patient in need thereof, wherein the symptom or sequela thereof comprises COVID-19-associated coagulopathy (CAC). In some embodiments, the methods are more generally for treating or inhibiting a coagulopathy (CAC) in a patient in need thereof. In some embodiments, the methods comprise (a) introducing blood or plasma comprising exosomes associated with a viral or bacterial infection (e.g., COVID-19), or the symptom or sequela thereof, such as CAC, from a patient having a viral or bacterial infection (e.g., COVID-19), or a symptom or sequela thereof, such as CAC, into an extracorporeal device comprising a lectin (e.g., GNA, NPA, or cyanovirin) that binds to said exosomes; (b) contacting the blood or plasma from the patient with the lectin in the extracorporeal device for a time sufficient to allow the exosomes present in the blood or plasma to bind to said lectin; (c) reintroducing the blood or plasma obtained after (b) into said patient, wherein the blood or plasma obtained after (b) has a reduced amount of the exosomes as compared to the blood or plasma of said patient prior to (b); and (d) optionally, detecting or identifying the exosomes in a sample from said patient, such as a nasal (e.g., isolated from a nasal swab), blood or plasma sample, prior to (a) or after (b) or both and/or, optionally selecting or identifying a patient having a viral or bacterial infection (e.g., COVID-19), or a symptom or sequela thereof, such as CAC, to receive a therapy that reduces said exosomes. In some embodiments, the patient does not comprise a viral or bacterial infection (e.g., COVID-19) prior to step (a) but exhibits symptoms or sequela of the infection, such as CAC. In some embodiments, the patient has cleared the infection prior to step (a), but the patient still exhibits symptoms or sequela of the infection, such as CAC. In some embodiments, the blood or plasma of the patient does not comprise the virus or bacteria (e.g., COVID-19)

prior to step (a), but the patient still exhibits symptoms or sequela of the infection, such as CAC. In some embodiments, the methods further comprise determining whether the patient has CAC, early acute lung injury (ALI), early acute respiratory distress syndrome (ARDS), dyspnea, respiratory frequency ≥30 breaths/min, blood oxygen saturation ≤93%, partial pressure of arterial oxygen to fraction of inspired oxygen ratio of <300, lung infiltrates >50%, respiratory failure within 24 to 48 hours, elevated ferritin, elevated lactate, elevated lactate dehydrogenase (LDH), low absolute lymphocyte count (ALC), low platelet count, elevated prothrombin time/international normalized ratio (PT/INR), septic shock, or multiple organ dysfunction or failure, or any combination thereof prior to (a) or after (b) or both. In some embodiments, the methods further comprise determining whether the patient has CAC prior to (a) or after (b), or both. In some embodiments, the methods further comprise determining whether the patient has an elevated IL-6 level or amount in a blood or plasma sample either before (a) or after (b) or both, as compared to a control level or amount (e.g., a level or amount found in a blood or plasma sample from a healthy patient or a patient not experiencing inflammation or COVID-19 infection or a sequela associated therewith). In some embodiments, the elevated serum IL-6 level is greater than equal to 2 pg/mL. In some embodiments, the methods further comprise determining whether the patient has an elevated D-dimer level or amount in a blood or plasma sample either before (a) or after (b) or both, as compared to a control level or amount (e.g., a level or amount found in a blood or plasma sample from a healthy patient or a patient not experiencing inflammation or COVID-19 infection or a sequela associated therewith). In some embodiments, the elevated serum D-Dimer level is greater than or equal to 500 ng/mL. In some embodiments, the methods further comprise determining whether the patient has an elevated Troponin T level or amount in a blood or plasma sample either before (a) or after (b) or both, as compared to a control level or amount (e.g., a level or amount found in a blood or plasma sample from a healthy patient or a patient not experiencing inflammation or COVID-19 infection or a sequela associated therewith). In some embodiments, the elevated serum Troponin T level is greater than or equal to 15 ng/L. In some preferred embodiments, the lectin is *Galanthus nivalis* agglutinin (GNA). In some embodiments, the extracorporeal device comprises a hollow fiber cartridge comprising the lectin and wherein the blood or plasma flows through hollow fibers of the hollow fiber cartridge. In some embodiments, the hollow fibers of the hollow fiber cartridge comprise a pore size that excludes cellular components of the blood or plasma from contacting the lectin. In some embodiments, the pore size is 20-500 nm or about 20-500 nm. In some embodiments, the pore size is 200 nm or about 200 nm. In some embodiments, the lectin is immobilized or adsorbed on to a solid support, and the hollow fiber cartridge comprises the lectin immobilized or adsorbed on the solid support. In some embodiments, the solid support comprises agarose, diatomaceous earth, or aminocelite. In some embodiments, the solid support comprises diatomaceous earth. In some embodiments, the methods further comprise isolating coronavirus virions, or portions thereof, bound to the lectin of the extracorporeal device. In some embodiments, the methods further comprise isolating exosomes associated with the coronavirus infection, or the symptom or sequela thereof, such as CAC, bound to the lectin of the extracorporeal device. In some embodiments, the methods further comprise determining the contents of the isolated exosomes. In some embodiments, the exosomes associated with the coronavirus infection, or the symptom or sequela thereof, such as CAC, comprises miR-424-5p, or miR-16-2-3p, or both. In some embodiments, the methods further comprise observing or measuring a reduction in number of coronavirus virions, or portions thereof; number of exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T, or any combination thereof, in a sample of the patient's blood or plasma taken after (b) relative to a sample of the patient's blood taken before (b). In some embodiments, the methods further comprise observing an improvement in the coronavirus infection, or the symptom or sequela thereof, such as CAC, in the patient following (b) or (c) or both. In some embodiments, observing the improvement in the coronavirus infection, or the symptom or sequela thereof, such as CAC, comprises determining an improvement in the CAC, early ALI, early ARDS, respiratory frequency, blood oxygen saturation, partial pressure of arterial oxygen to fraction of inspired oxygen ratio, lung infiltrates, respiratory failure, ferritin, lactate, LDH, ALC, platelet count, PT/INR, septic shock, or multiple organ dysfunction or failure, or any combination thereof, in the patient. In some embodiments, observing the improvement in the coronavirus infection, or the symptom or sequela thereof, such as CAC, comprises observing a reduction in number of coronavirus virions, or portions thereof; exosomes associated with the coronavirus infection, or the symptom or sequela thereof; or measuring the level or amount of IL-1, IL-6, IL-10, IL-15, CXCL10, CCL2, Myeloperoxidase, VCAM-1, TNF alpha, C-reactive protein (CRP), D-dimer, or Troponin-T, or any combination thereof in the patient relative to before the treatment. In some embodiments, the coronavirus infection is caused by a coronavirus selected from SARS-CoV-2, SARS-CoV-1, MERS-CoV, HCoV-229E, HCoV-OC43, HCoV NL63, or HCoV-HKU1. In some embodiments, the SARS-CoV-2 is a SARS-CoV-2 variant. In some embodiments, the variant is selected from 20I/501Y.V1 (B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429). In some embodiments, the extracorporeal device is primed with an anticoagulant, preferably heparin, to prevent clotting of blood prior to (a). In some embodiments, the blood is flowed at a rate of about 50 to about 600 mL/min, preferably about 200 to about 400 mL/min, preferably about 200 to about 240 mL/min or 200 mL/min to 240 mL/min, most preferably 240 mL/min, through said extracorporeal device. In some embodiments, reintroducing the blood back to the patient comprises flushing the extracorporeal device with saline. In some embodiments, the blood or plasma is contacted with the extracorporeal device for 0.1, 0.2, 0.3, 0.4, 0.5, 0.6, 0.7, 0.8, 0.9, 1, 2, 3, 4, 5, 6, 7, 8, 9, or 10 hours, or any amount of time within a range defined by any two of the aforementioned times. In some embodiments, steps (a), (b), (c), and optionally (d) is repeated every day for 1, 2, 3, 4, 5, 6, 7, 8, 9, 10, 11, 12, 13, 14, or 15 days. In some embodiments, the methods further comprise administering an additional antiviral therapy to the patient. In some embodiments, the additional antiviral therapy comprises favipiravir, favilavir, remdesivir, tocilizumab, galidesivir, sarilumab, lopinavir, ritonavir, darunavir, ribavirin, interferon-α, pegylated interferon-α, interferon alfa-2b, convalescent serum, or any combination thereof.

Also disclosed herein are methods for reducing the amount of SARS-CoV-2 virions, or fragments thereof, in a COVID-19 patient. In some embodiments, the methods comprise (a) providing an extracorporeal device comprising a hollow fiber cartridge comprising a lectin that selectively binds to the outer surfaces of SARS-CoV-2 virions, or fragments thereof; (b) removing blood from a COVID-19 patient; (c) processing the blood from the hollow fiber cartridge such that the lectin is in contact with the blood; (d) reducing at least a portion of SARS-CoV-2 virions, or fragments thereof such that said portion of SARS-CoV-2 virions, or fragments thereof is retained in the hollow fiber cartridge; and (e) reintroducing the blood without said portion of SARS-CoV-2 virions, or fragments thereof to the patient. In some embodiments, the lectin is GNA.

Also disclosed herein are methods for reducing the amount of COVID-19 mediating nanoparticles in a COVID-19 patient. In some embodiments, the methods comprise (a) providing an extracorporeal device comprising a hollow fiber cartridge comprising a lectin that selectively binds to the outer surfaces of COVID-19 mediating nanoparticles; (b) removing blood from a COVID-19 patient; (c) processing the blood from the hollow fiber cartridge such that the lectin is in contact with the blood; (d) reducing at least a portion of COVID-19 mediating nanoparticles such that said portion of COVID-19 mediating nanoparticles is retained in the hollow fiber cartridge; and (e) reintroducing the blood without said portion of COVID-19 mediating nanoparticles to the patient. In some embodiments, the lectin is GNA.

Also disclosed herein are methods for reducing the amount of COVID-19 mediating exosomes in a COVID-19 patient. In some embodiments, the methods comprise (a) providing an extracorporeal device comprising a hollow fiber cartridge comprising a lectin that selectively binds to the outer surfaces of COVID-19 mediating exosomes; (b) removing blood from a COVID-19 patient; (c) processing the blood from the hollow fiber cartridge such that the lectin is in contact with the blood; (d) reducing at least a portion of COVID-19 mediating exosomes such that said portion of COVID-19 mediating exosomes is retained in the hollow fiber cartridge; and (e) reintroducing the blood without said portion of COVID-19 mediating exosomes to the patient. In some embodiments, the lectin is GNA.

Also disclosed herein are methods for reducing the amount of IL-6 in a COVID-19 patient. In some embodiments, the methods comprise (a) providing an extracorporeal device comprising a hollow fiber cartridge comprising a lectin that selectively binds to the outer surfaces SARS-CoV-2 virions or fragments thereof or COVID-19 mediating exosomes; (b) removing blood from a COVID-19 patient; (c) measuring the levels of IL-6 in the blood; (d) processing the blood from the hollow fiber cartridge such that the lectin is in contact with the blood; (e) reducing at least a portion of COVID-19 mediating exosomes such that said portion of SARS-CoV-2 virions or fragments thereof or COVID-19 mediating exosomes is retained in the hollow fiber cartridge; (f) measuring the levels of IL-6 in the blood; and (g) reintroducing the blood without said portion of surfaces SARS-CoV-2 virions or fragments thereof or COVID-19 mediating exosomes to the patient. In some embodiments, the lectin is GNA.

Also disclosed herein are methods for reducing the amount of D-dimer in a COVID-19 patient. In some embodiments, the methods comprise (a) providing an extracorporeal device comprising a hollow fiber cartridge comprising a lectin that selectively binds to the outer surfaces SARS-CoV-2 virions or fragments thereof or COVID-19 mediating exosomes; (b) removing blood from a COVID-19 patient; (c) measuring the levels of D-dimer in the blood; (d) processing the blood from the hollow fiber cartridge such that the lectin is in contact with the blood; (e) reducing at least a portion of COVID-19 mediating exosomes such that said portion of SARS-CoV-2 virions or fragments thereof or COVID-19 mediating exosomes is retained in the hollow fiber cartridge; (f) measuring the levels of D-dimer in the blood; and (g) reintroducing the blood without said portion of surfaces SARS-CoV-2 virions or fragments thereof or COVID-19 mediating exosomes to the patient. In some embodiments, the lectin is GNA.

Also disclosed herein are methods for reducing the amount of Troponin T in a COVID-19 patient. In some embodiments, the methods comprise (a) providing an extracorporeal device comprising a hollow fiber cartridge comprising a lectin that selectively binds to the outer surfaces SARS-CoV-2 virions or fragments thereof or COVID-19 mediating exosomes; (b) removing blood from a COVID-19 patient; (c) measuring the levels of Troponin T in the blood; (d) processing the blood from the hollow fiber cartridge such that the lectin is in contact with the blood; (e) reducing at least a portion of COVID-19 mediating exosomes such that said portion of SARS-CoV-2 virions or fragments thereof or COVID-19 mediating exosomes is retained in the hollow fiber cartridge; (f) measuring the levels of Troponin T in the blood; and (g) reintroducing the blood without said portion of surfaces SARS-CoV-2 virions or fragments thereof or COVID-19 mediating exosomes to the patient. In some embodiments, the lectin is GNA.

Also disclosed herein are extracorporeal devices comprising a lectin for use in the treatment or inhibition of a coronavirus infection, or a symptom or sequela thereof, or to reduce the levels or amounts of IL-1, IL-6, IL-10, IL-15, CXCL10, CCL2, Myeloperoxidase, VCAM-1, TNF alpha, C-reactive protein (CRP), D-dimer, or Troponin-T or any combination thereof in a patient in need thereof. Also disclosed herein are extracorporeal devices comprising a lectin for use in the treatment or inhibition of COVID-19-associated coagulopathy in a patient in need thereof. Also disclosed herein are extracorporeal devices comprising a lectin for use in a method of treating or inhibiting a coronavirus infection, or a symptom or sequela thereof, in a patient in need thereof, the method comprising flowing blood from the patient through the extracorporeal device such that the blood comes in contact with the lectin, thereby resulting in processed blood; and reintroducing the processed blood back to the patient. In some preferred embodiments, the lectin is *Galantus nivalis* agglutinin. In some embodiments, the extracorporeal device comprises a hollow fiber cartridge comprising the lectin, wherein the blood of the patient flows through hollow fibers of the hollow fiber cartridge. In some embodiments, the lectin is immobilized or adsorbed onto a solid support, and the hollow fiber cartridge comprises the lectin immobilized or adsorbed on the solid support. In some embodiments, the solid support is agarose, diatomaceous earth, or aminocelite. In some embodiments, the solid support is diatomaceous earth. In some embodiments, the lectin selectively binds to coronavirus virions, or portions thereof, exosomes associated with the coronavirus infection, or the symptoms or sequela thereof, or any combination thereof. In some embodiments, the coronavirus infection is caused by a coronavirus selected from SARS-CoV-2, SARS-CoV-1, MERS-CoV, HCoV-229E, HCoV-OC43, HCoV NL63, or HCoV-HKU1. In some embodiments, the SARS-CoV-2 is a SARS-CoV-2 variant. In some embodiments, the SARS-CoV-2 variant is selected from 20I/501Y.V1 (B.1.1.7), 20H/501Y.V2 (B.1.351), 20J/501Y.V3 (P.1), B.1.1.207, VUI-202102/03 (B.1.525), VUI-202101/01 (P.2), VUI-202102/01 (A.23.1), VUI 202102/04 (B.1.1.318), VUI 202103/01 (B.1.324.1), or CAL.20C (B.1.429). In some embodiments, the extracorporeal device is used for 0.1, 0.2, 0.3, 0.4, 0.5, 0.6, 0.7, 0.8, 0.9, 1, 2, 3, 4, 5, 6, 7, 8, 9, or 10 hours at a time, or any amount of time within a range defined by any two of the aforementioned times. In some embodiments, the extracorporeal device is used every day for 1, 2, 3, 4, 5, 6, 7, 8, 9, 10, 11, 12, 13, 14, or 15 days. In some embodiments, the extracorporeal device is used with an additional antiviral therapy. In some embodiments, the additional antiviral therapy comprises favipiravir, favilavir, remdesivir, tocilizumab, galidesivir, sarilumab, lopinavir, ritonavir, darunavir, ribavirin, interferon-α, pegylated interferon-α, interferon alfa-2b, convalescent serum, or any combination thereof.

The invention is generally disclosed herein using affirmative language to describe the numerous embodiments. The invention also includes embodiments in which subject matter is excluded, in full or in part, such as substances or materials, method steps and conditions, protocols, or procedures.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention, as it is described herein above and in the claims.

Example 1: Preparation of an Exemplary Lectin Agarose Affinity Matrix

This example demonstrates the preparation of an affinity matrix using GNA covalently coupled to Agarose using Cyanogen Bromide. Cyanogen bromide (CNBr) activated agarose was used for direct coupling essentially according to Cuatrecasas, et al (Cuatracasas et al. Proc Natl Acad Sci USA 61(2): 636-643, 1968). In brief, 1 ml of GNA at a concentration of 10 mg/ml in 0.1M NaHCO$_3$ pH 9.5 is added to 1 ml CNBr activated agarose (Sigma, St. Louis, Mo.) and allowed to react overnight in the cold. When the reaction is complete, unreacted materials are aspirated and the lectin coupled agarose washed extensively with sterile cold PBS. The lectin agarose affinity matrix is then stored cold until ready for use. Alternatively, GNA agarose is available commercially from Vector Labs (Burlingame, Calif.).

Example 2: Preparation of an Exemplary Lectin Silica Affinity Matrix

This example demonstrates preparation of the lectin affinity matrix using GNA covalently coupled to glass beads via Schiff's base and reduction with cyanoborohydride. The lectin silica affinity matrix was prepared by a modification of the method of Hermanson (Hermanson. Bioconjugate Techniques: 785, 1996). GNA lectin was dissolved to a final protein concentration of 10 mg/ml in 0.1M sodium borate pH 9.5 and added to aldehyde derivatized silica glass beads (BioConnexant, Austin Tex.). The reaction is most efficient at alkaline pH but will go at pH 7-9 and is normally done at a 2-4 fold excess of GNA over coupling sites. To this mixture was added 10 μl 5M NaCNBH$_3$ in 1N NaOH (Aldrich, St Louis, Mo.) per ml of coupling reaction and the mixture allowed to react for 2 hours at room temperature. At the end of the reaction, remaining unreacted aldehyde on the glass surfaces are capped with 20 μl 3M ethanolamine pH 9.5 per ml of reaction. After 15 minutes at room temperature, the reaction solution was decanted and the unbound proteins and reagents removed by washing extensively in PBS. The matrix was the stored in the refrigerator until ready for use.

Example 3: Preparation of an Exemplary Lectin Aminocelite Affinity Matrix

This example demonstrates preparation of GNA covalently coupled to aminocelite using glutaraldehyde. Aminocelite was prepared by reaction of celite (silicate containing diatomaceous earth) by overnight reaction in a 5% aqueous solution of aminopropyl triethoxysilane. The aminated celite was washed free of excess reagent with water and ethanol and dried overnight to yield an off-white powder. One gram of the powder was then suspended in 5 ml 5% glutaraldehyde (Sigma) for 30 minutes. Excess glutaraldehyde was then removed by filtration and washing with water until no detectable aldehyde remained in the wash using Schiff's reagent. The filter cake was then resuspended in 5 ml of Sigma borohydride coupling buffer containing 2-3 mg/ml GNA and the reaction allowed to proceed overnight at room temperature. At the end of the reaction, unreacted GNA was washed off and the unreacted aldehyde aminated with ethanolamine as described. After final washing in sterile PBS, the material was stored cold until ready for use.

Example 4: Preparation of an Exemplary Lectin Diatomaceous Earth Affinity Matrix A lectin affinity viral hemodialysis device is made by pouring a dry powder consisting of GNA immobilized on diatomaceous earth (CHROMOSORB GAW 60/80; Celite Corp, Lompoc, Calif.) into the outside compartment of a hollow-fiber plasmapheresis column (PLASMART 60; Medica, srl, Medollo Italy) using a funnel attached to the outlet ports of the column. The powder (40 grams) is introduced under gravity flow with shaking to fill the available extrafiber space. For therapeutic use, the cartridges containing the affinity resin is heat sealed in TYVEK shipping pouches and sterilized with 25-40 kGy gamma irradiation. Samples of the product are then tested for sterility and endotoxin and found to meet FDA standards. The finished product can be stored for at least 6 months at room temperature in a cool dry place until ready for use.

Example 5: Preparation of an Exemplary Lectin Affinity Matrix Cartridge

This example demonstrates preparation of a GNA lectin affinity hemodialysis device. The viral device was made by pumping a slurry of particulate immobilized GNA on agarose beads or celite in sterile PBS buffer into the outside compartment of a hollow-fiber dialysis column using a syringe. For blood samples up to 15 mls, Microkros polyethersulfone hollow-fiber dialysis cartridge equipped with Luer fittings (200 μm ID, 240 μm OD, pore diameter 200-500 nm, approximately 0.5 ml internal volume) obtained from Spectrum Labs (Rancho Dominguez, Calif.) were used. Cartridges containing the affinity resin were equilibrated with 5-10 column volumes sterile PBS.

Example 6: The Lectin GNA Binds to SARS-CoV-2 Spike Protein

Figure 4:
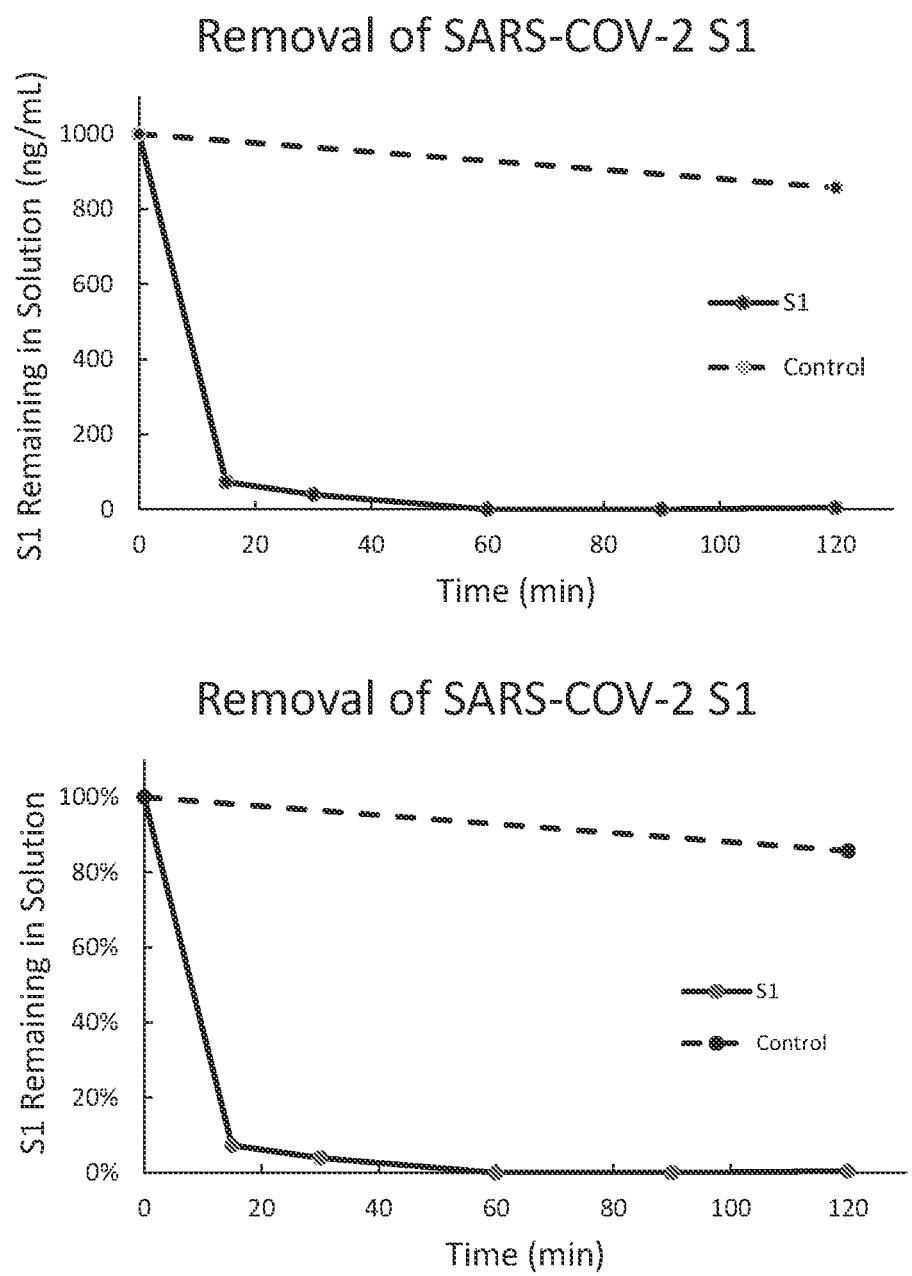
FIG. 4 is a graphical representation of the capture of SARS-CoV-2 spike 1 (S1) glycoproteins with a lectin affinity cartridge. In vitro experiments were performed by continuously circulating a solution spiked with S1 glycoprotein of SARS-COV-2 over a porous hollow fiber membrane device, wherein lectin molecules consisting of *Galanthus nivalis* agglutinin (GNA) were immobilized within the porous exterior portion of the membrane. Briefly, 10 mL of a 1 microgram/mL solution of SARS-COV-2 S1 in phosphate buffered saline was circulated over a device containing 0.7 g of GNA affinity resin at a flow rate of 50 mL/min. The rate of viral S1 capture, expressed as a percentage of S1 remaining in solution vs. time, was established by removing fluid samples at defined time intervals. The control consisted of S1 kept on the benchtop (i.e., not run through the device). The results show the clearance of SARS-CoV-2 glycoprotein from the solution by the lectin affinity capture device.
Figure 5:
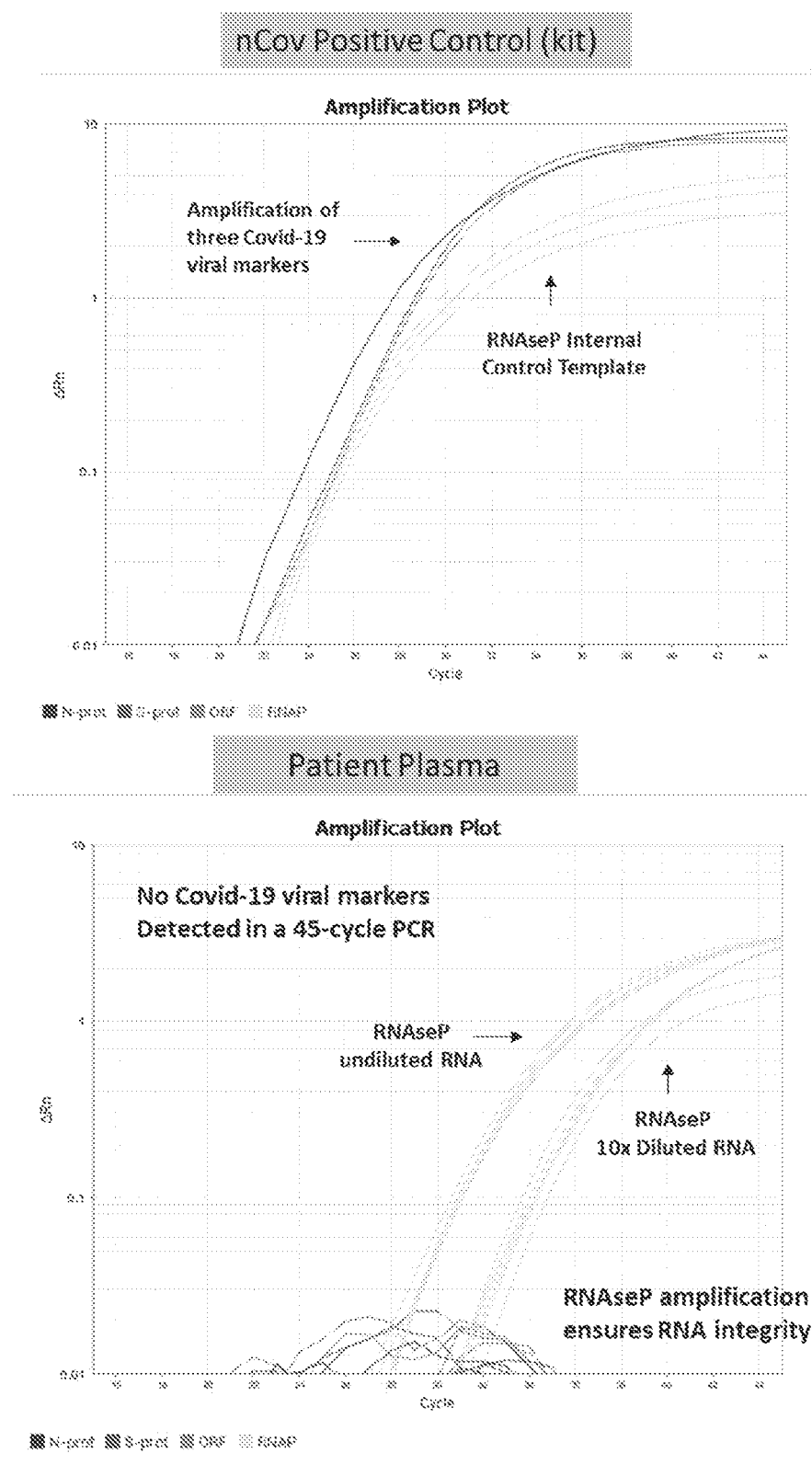
FIG. 5 depicts the absence of detectable SARS-CoV-2 RNA in a patient. A positive control PCR using SARS-CoV-2 nucleic acid templates demonstrates amplification of the SARS-CoV-2 spike (S) protein, nucleocapsid (N) protein, and ORF1ab sequences. The same reaction performed with a plasma sample from the patient resulted in no amplification for any of the three SARS-CoV-2 genes. Concurrent amplification of an RNAse P control gene (either as part of the control template or as RNA isolated from the plasma sample) confirmed nucleic acid integrity of the constituent RNA in the samples before and during the reaction. Accordingly, this patient did not have circulating COVID-19 viral particles.

The devices and methods of the present invention capture SARS-CoV-2 spike 1 (S1) glycoproteins and deplete them from a sample. Experiments were performed by continuously circulating a solution spiked with S1 glycoprotein of SARS-COV-2 over the mini-device column in vitro. Briefly, 10 mL of a 1 µg/mL solution of SARS-COV-2 S1 (i.e., SARS-CoV-2 (2019-nCoV) Spike S1-His Recombinant Protein (HPLC-verified) Sino Biological Catalog Number: 40591-V08H) in phosphate buffered saline was circulated over a Hemopurifier® containing 0.7 g of affinity resin (comprising GNA and CHROMOSORB GAW 60/80) at a flow rate of 50 mL/min. The rate of viral S1 capture, expressed as a percentage of S1 remaining in solution vs. time, was established by removing fluid samples at defined time intervals. The control consisted of S1 kept on the benchtop (i.e., not run through the device). As seen in FIG. 4, over 90% of the S1 protein in the test sample is depleted by the first time point at 15 minutes, and no S1 is detected following 60 minutes of flow through the column.

Example 7: Treatment of COVID-19 with a GNA Lectin Affinity Hemofiltration Device This example pertains to methods of use of a clinical hemofiltration device for treatment of COVID-19. A clinical study will be performed to evaluate the use of an extracorporeal lectin affinity hemofiltration device to capture and remove COVID-19 mediating nanoparticles for the treatment of SARS-CoV-2 Virus Disease (COVID-19).

The device of the present invention is a single-use hollow-fiber plasmapheresis cartridge that is modified to contain an affinity matrix consisting of the lectin *Galanthus nivalis* agglutinin (GNA), which is incorporated between hollow fibers running the length of the cartridge. As blood enters the device, enveloped viruses in the blood are transported via convection and diffusion through pores in the hollow fibers having nominal pore sizes of 200 nm where they contact the affinity matrix. The viruses are captured by GNA and prevented from re-entry into the circulation. Meanwhile, the cellular components of the blood remain within the lumen of the fibers and are excluded from contact with the affinity matrix. The device is operated by establishing access to a subject's circulatory system with a dual lumen central catheter and utilizing standard dialysis infrastructure to achieve hemofiltration.

The objectives of the study will be as follows: Assessment of safety of the hemofiltration device. Evaluating the changes in circulating viral load in blood by RT-PCR. Elution of viral particles from used hemofiltration cartridges and measuring viral load. Evaluating clinical outcomes include assessing survival rate, time on ventilator, incidence of multiorgan systems failure, and measuring markers of inflammation, coagulation, and tissue damage.

The following subjects will be enrolled in the study: Subjects who have been diagnosed with COVID-19 with any of the following disease characteristics: Early acute lung injury (ALI)/early acute respiratory distress syndrome (ARDS); and/or severe COVID-19 disease or at risk for severe COVID-19 disease as defined as: dyspnea, respiratory frequency ≥30/min, blood oxygen saturation ≤93%, partial pressure of arterial oxygen to fraction of inspired oxygen ratio of <300 and/or lung infiltrates >50% within 24 to 48 hours; and/or Life-threatening disease, defined as: respiratory failure, septic shock, and/or multiple organ dysfunction or failure.

Procedures for patients prior to treatment with the hemofiltration device: Blood samples will be collected for pre-treatment assessment of cytokines/inflammatory and coagulation markers and other blood biomarkers of organ damage, as well as for blood cell counts. Also, a pre-treatment blood sample will be used for detection of viral material. For example, SARS-CoV-2 RNA may be evaluated by RT-PCR. An additional blood sample may be used for evaluation of exosomes present in the patient's circulatory system prior to treatment for later comparison to the post-treatment exosomes. In preparation for treatment, a hemodialysis catheter will be placed into the patient.

Preparation of the Device for Hemopurification:
  The extracorporeal circuit is to be connected;
  The extracorporeal circuit is primed and rinsed with a minimum of two liters of priming solution;
  An anticoagulant such as heparin will be added per liter of priming solution if needed to prevent clotting of the blood circuit;
  The initial flow rate for priming will be 200-250 mL/min and up to 400-500 ml/min for several minutes to increase the shear forces inside the fibers to encourage the dislodgement of microbubbles. During this procedure, all bubbles are removed from the tubing and the cartridge by gentle tapping.

Therapy:
  For use on a patient with established vascular access, the patient will be connected to the dialysis machine, which pumps blood from the patient through the cartridge and returns the purified blood to the patient. Blood flow rates are typically maintained at 200 to 400 ml/min at the discretion of the attending physician. Heparin injections are most often used to prevent blood clotting. Typical treatment times are up to 4 hours for dialysis patients. Longer times may be used to increase the effectiveness of the treatment. At the end of the treatment, the blood in the tubing and cartridge is washed back into the patient using sterile saline. The machine is then disconnected from the patient and the contaminated cartridge and blood tubing properly disposed.

During the therapy with the device, testing will be performed to measure the activated clotting times (ACT) for monitoring anticoagulation.

Procedures after Therapy:
  The used hemofiltration device will be removed from the circuit, flushed with physiologic saline and as much of the fluid from the cartridge as possible will be evacuated.

The used hemofiltration device should be placed into a clear plastic pouch and sealed after which it should be stored in a freezer until being shipped to the appropriate laboratory facility for analysis.

Blood sample will be collected from the patient for post-treatment assessment of cytokines/inflammatory markers, other blood biomarkers of organ damage, and blood cell counts.

Results:
  Pre- and post-treatment blood samples from a COVID-19 patient that will receive the therapy above will have a significantly reduced load of viral RNA in the blood post-therapy. SARS-CoV-2 may be detected based on viral RNA using RT-PCR. Enzyme-linked immunosorbent assays (ELISA) may be used to detect and/or quantify viral proteins (for example, the spike ("S") glycoproteins or the nucleocapsid protein). Serological assays to detect viral proteins may utilize antibodies that exhibit specificity for one or more conserved epitopes on SARS-CoV-2.

For analysis of viral material captured by the hemofiltration device, one of the abovementioned techniques for measurement of viral material (e.g. RNA by RT-PCR) will be performed to detect SARS-CoV-2 that was removed from the patient's circulatory system.

The results of analysis of the used hemofiltration device will show the capture of SARS-CoV-2 from the circulation by the hemofiltration device.

Blood samples collected from a COVID-19 patient at various intervals after treatment with a hemofiltration device will show reduced levels of D-dimer, a fibrin degradation product.

Blood samples collected from a COVID-19 patient at various intervals after therapy with a hemofiltration device will show reduced levels of Troponin T after treatment with the hemofiltration device vs. pre-treatment.

Laboratory analysis of pre-therapy blood samples may show evidence of lymphopenia and, specifically, may show the presence of abnormally low concentrations of T cells and NK cells in the peripheral blood. Post-therapy blood samples will show a partial or full restoration of the concentrations of total lymphocytes, T cells, and NK cells in the days and weeks following treatment with the device.

Serum samples will be subjected to laboratory analysis using ELISA to quantify concentrations of markers such as IL-6, IL-10, IL-15, CXCL-10, and/or CCL-2. Laboratory evaluations will include the following: complete blood count with differential; comprehensive metabolic panel including LDH, ferritin, and C-reactive protein (CRP); concentrations of inflammatory cytokines and chemokines (IL-6, IL-10, IL-15, CXCL10, CCL2; Myeloperoxidase; VCAM-1; LDH; D-dimer and PT-INR; nasopharyngeal sample for SARS-CoV-2; viral (SARS-CoV-2) RNA quantification from plasma; viral (SARS-CoV-2) RNA quantification from post-treatment Hemopurifier® cartridges. A COVID-19 patient will demonstrate reduced IL-6, IL-10, IL-15, CXCL-10, and/or CCL-2 concentrations in serum following treatment with the hemofiltration device.

Serum samples will be subjected to laboratory analysis using ELISA to quantify C-reactive protein (CRP) concentrations. A COVID-19 patient will present with reduced CRP concentrations in serum following treatment with the hemofiltration device.

Clinical outcomes in COVID-19 patients that received the aforementioned therapy with the hemofiltration device will show improvements in clinical parameters, which may include a reduction or resolution in pulmonary lesions based on chest CT scans and reduced time spent on a ventilator and improvement of multi-organ failure.

The devices and methods of the present invention can be used to reduce the time spent on mechanical ventilators, reduce the likelihood of acute respiratory distress syndrome, reduce the likelihood of cardiac complications including arrhythmias and heart failure, reduce the likelihood of multi-organ failure, reduce the likelihood of acute kidney disease, sepsis and/or other complications. For example, for severely affected COVID-19 patients with systemic inflammation, the devices and methods of the present invention can suppress or reduce the production or presence of cytokines such as IL-6.

The devices and methods of the present invention can be used to improve coagulopathy in patients with COVID-19, as indicated by, the reduction in D-dimer levels in blood, shortening of the prothrombin time and international normalized ratio (PT/INR), and increase in the platelet count.

Example 8. Hemofiltration of a Post-Infection Patient with a Lectin Affinity Matrix Resulted in Significant Improvement in Clinical Status A patient presented with severe persistent respiratory decline and an O2 saturation of 40%-50% following a COVID-19 infection. However, the patient displayed no improvement in condition, and remained on 100% O2 ventilation. Emergency use of the GNA lectin affinity matrix cartridge disclosed herein (using a CHROMOSORB GAW 60/80 support) was authorized for the patient. The patient underwent whole blood hemodialysis with the lectin cartridge at a flow rate of 200 mL/min for 6 hours a day for a total of 8 days, using a fresh cartridge every day. Pre-therapy and post-therapy blood draw samples were taken. Pre-therapy blood draw samples collected on day 1 did not contain any detectable circulating COVID-19 viremia as tested by qPCR of patient plasma (FIG. 5). On day 1, the therapy was interrupted due to blood clotting issues, but no issues arose in the remaining days. After the hemofiltration therapy, the patient made a remarkable recovery, exhibiting partial pressure of oxygen (PaO2) of 105 mmHg and no longer requiring pure oxygen.

Specimens of the patient blood draws and the contents of the Hemopurifier® cartridges were examined to determine the components that were isolated from the patient by hemodialysis. 700 μL each of 8 pre-treatment and 8 post-treatment plasma samples (with EDTA anticoagulant) were processed in buffer AVL (Qiagen) to isolate nucleic acids for detection of viral genome and miRNA. An additional 1 mL each of 8 pre-therapy and 8 post-therapy plasma samples (with EDTA anticoagulant) were stored unprocessed for detection of intact exosomes and exosome cargo (including protein and miRNA). Used Hemopurifiers® were processed with 1) 1 M alpha-methylmannoside (a-MM; a lectin binding competitor) and subsequently 2) TRIzol® reagent (Thermo Fisher) (to liberate remaining nucleic acids) to elute blood components bound to the GNA lectin. Approximately 200 mL of eluate was obtained from each step and for each of the 4 Hemopurifiers®.

An overview of the outcome of the patient and results of the analysis of exosomes from patient samples is provided in this example. Additional information regarding the exosome analysis is provided in Examples 9-10. Table 1 summarizes this overview.

1) 8 days prior to therapy (Jul. 30, 2020), the patient had evidence of tissue injury with an LDH of 2370 U/L, and evidence of systemic inflammation with ferritin of 3599.5 ng/ml.
2) On Aug. 1, 2020 (6 days prior to therapy), the patient had evidence of endothelial damage/coagulopathy with a D-dimer >7650 ng/ml.
3) On Aug. 3, 2020 (4 days prior to therapy), the patient had evidence of tissue hypoxia with a lactate of 3.6 mmol/L.
4) Total exosomal concentration decreased pre- to post-therapy over days 2-4 after the therapy was given.
5) Exosomal miRNA miR-424 and miR-16 decreased over the first 4 days after therapy was given.
6) On Aug. 7, 2020 (Day #1, the first day of HP treatment), the patient had ongoing evidence of endothelial damage/coagulopathy with a platelet count that was low at 115,000/mcl, as well as a prolonged PT-INR at 1.2 (13.6 seconds). The patient had evidence of ARDS with a PaO2/FIO2 ratio of 93 (PaO2 65 mmHg on an FIO2 of 0.70). The patient also had evidence of systemic inflammation with an IL-6 level of 641.7 pg/ml, total WBC of 15,500/mcl and lymphopenia with an absolute lymphocyte count of 780/mcl.
7) On Aug. 8, 2020 (Day #2, the second day of HP treatment), the PaO2/FIO2 ratio was 98 (PaO2 98 mmHg on an FIO2 of 1.0). The patient's lactate has decreased to 2.3 mmol/l.

8) On Aug. 9, 2020 (Day #3, the third day of HP treatment), the PaO2/FIO2 was 75.5 (PaO2 of 68 mmHg with an FIO2 of 0.90).
9) On Aug. 10, 2020 (Day #4, the fourth day of HP treatment), PaO2/FIO2 was 88.57 (PaO2 of 62 mmHg with an FIO2 of 0.70).
10) On Aug. 12, 2020, prior to Day #5 of treatment, the patient had evidence of improvement in COVID-19 induced coagulopathy with D-dimer decreasing to 3703 ng/ml, PT dropping to 11.3 seconds (PT-INR 1.0) and platelet count improving to 162,000/mcl. The decrease in exosomal miR-424 by the Hemopurifier® is thought to have played a role in this improvement, as miR-424 levels have been increased in thrombosis associated with COVID-19. The patient also had an improvement in pulmonary function with the PaO2/FIO2 rising to 136.25 (PaO2 of 109 mmHg with FIO2 requirement of 0.80). Increased miR-16 has been associated with LPS-induced acute lung injury and increased miR-424 has been associated with ARDS. Decreases in these two exosomal miRNAs by the therapy is thought to have played a role in the patient's improvement in oxygenation. Systemic inflammation had improved with ferritin decreasing to 622.4 ng/ml and lymphopenia resolved with an ALC up to 1180/mcl. Tissue injury had improved with LDH decrease to 978 U/L. Tissue hypoxia improved with lactate that was normal at 0.8 mmol/L.
11) Level of exosomal miR-424 and miR-16 decreased by Aug. 12, 2020.
12) Total exosomal concentration went up pre- to post-therapy.
13) Over post-therapy days 6-8 (Aug. 13-Aug. 15, 2020), a change in PaO2/FIO2 ratio was not observed, with it being 117.14, 126.6, and 120, respectively with the patient remaining on an FIO2 of 0.70 on Aug. 15, 2020.
14) Levels of exosomal miRNAs decreased post-therapy on Day #8, eight days after the therapy was given.
15) On Aug. 19, 2020, the PaO2/FIO2 ratio was up to 149.23 (PaO2 of 92 mmHg on FIO2 of 0.65).
16) On Aug. 20, 2020, the PaO2/FIO2 ratio had risen to 175 (PaO2 of 105 mmHG on FIO2 of 0.60).
17) Labs on Aug. 24, 2020 indicated the presence of significant inflammation with ferritin back up to 1583.8 ng/ml and a CRP>270 mg/L. Additionally, the coagulopathy had again worsened with a D-dimer of 5595 ng/ml and a PT-INR of 1.3. Of note, the patient's Procalcitonin had risen to 2.11 ng/ml on this day after having been normal at 0.19 ng/ml on Aug. 12, 2020. This raised the possibility of a bacterial superinfection being present and explains the patient's clinical worsening.

TABLE 1

Summary of COVID-19 patient data

| Date | D-dimer (ng/ml) | Platelet (cells/mcl) | PT/INR | Ferritin (ng/ml) | Lactate (mmol/l) | PaO2/FIO2 ratio | ALC (absolute lymphocyte count) (cells/mcl) | LDH (U/L) |
| --- | --- | --- | --- | --- | --- | --- | --- | --- |
| Jul. 30, 2020 (8 days prior to therapy) | | | | 3599.5 (systemic inflammation) | | | | 2370 (tissue injury) |
| Aug. 1 (6 days prior to therapy) | >7650 | | | | | | | |
| Aug. 3 (4 days prior to therapy) | | 115,000 | | | 3.6 (tissue hypoxia) | | | |
| Aug. 7 (Day 1 therapy) | | | 1.2 (13.6 sec, prolonged) | | | 93 | 780 (lymphopenia) | |
| Aug. 8 (Day 2 therapy) | | | | | 2.3 | 98 | | |
| Aug. 9 (Day 3 therapy) | | | | | | 75.5 | | |
| Aug. 10 (Day 4 therapy) | | | | | | 88.57 | | |
| Aug. 12 (Day 5 of therapy) | 3703 | 162,000 | 1.0 (11.3 sec, improved) | 622.4 | 0.8 (normal) | 136.25 | 1180 | 978 (improved) |
| Aug. 13-Aug. 15 (Days 6-8 of therapy) | | | | | | >117 | | |
| Aug. 20, 2020 (5 Days after completion of therapy) | | | | | | 175 | | |

Example 9: Exosomes were Depleted from the Patient by Hemofiltration

The effects of Hemopurifier® treatments on circulating exosome quantities and cargo in the COVID-19 patient treated for 8 days (6 hours/treatment) of Example 8 was determined. The analysis was done on patient plasma sets collected on days 1-4 of therapy. Pre-therapy plasma was collected before Hemopurifier® therapy. Post-therapy plasma was collected after the 6 hour Hemopurifier® treatment. On day 1, Hemopurifier® therapy was interrupted due to blood clotting issues, and more than 13 hours lapse between pre- and post-treatment blood draws. To briefly summarize the methods, after an initial particle characterization analysis of the unprocessed plasma, isolated exosomes are purified from the rest of the plasma components using a mini-size exclusion column (mini-SEC) procedure that removes other similarly sized particles and abundant protein contaminants. Using the mini-SEC methodology, purified exosome samples are collected in the Fraction #4 eluent and used for comparative analysis. Results presented represent yields from 1 mL of the COVID-19 patient plasma. Table 2 depicts the COVID-19 clinical samples that were collected.

Level of 12 and a Detection Threshold of 3. Three 30 second capture videos of different segments of the homogenous exosome sample were evaluated with the NTA 3.3 software in order to determine particle quantification and sizing measurements.

TABLE 2

Summary of COVID-19 plasma samples collected

| | Pre-treatment (t = 0) | Post-treatment (t = 6 hours) | Time lapse | Comments |
|---|---|---|---|---|
| Day 1 | 1 mL (10 AM) | 0.5 mL (11:30 PM) | 13 hr, 30 min | Initial 25 mm treatment. Blood clot problems. Clot reducing therapy needed. A second Hemopurifier ® cartridge was used to re-initiate the 6 hour treatment at 4 PM. |
| Day 2 | 0.8 mL (11 AM) | 0.8 mL (6:10 PM) | 7 hr, 10 min | No known issues |
| Day 3 | 1 mL (10:30 AM) | 1 mL (5:45 PM) | 7 hr, 30 min | No known issues |
| Day 4 | 1 mL (10:30 AM) | 1 mL (5:45 PM) | 7 hr, 15 min | No known issues |
| Day 5 | 0.8 mL (2:45 PM) | 0.4 mL (8:45 PM) | 6 hr, 0 min | No known issues |
| Day 6 | 0.8 mL (11:30 AM) | 0.8 mL (7:00 PM) | 7 hr, 30 min | No known issues |
| Day 7 | 1 mL (11:00 AM) | 0.8 mL (8:00 PM) | 9 hr, 0 min | Patient received a blood transfusion during therapy. A second Hemopurifier ® cartridge was used to complete the therapy. |
| Day 8 | 0.75 mL (11:45 AM) | 0.6 mL (6:15 PM) | 6 hr, 30 min | No known issues |

Isolation of Exosomes from Patient Plasma: Exosomes were purified from patient plasma using an established methodology in the art (Ludwig et al. *Curr. Protoc. Immunol.* (2019) 127:e91, which is hereby expressly incorporated by reference in its entirety). 1 mL of patient plasma was precleared through a two-step centrifugation process to remove larger plasma particles, then filtered through a 0.22 µM PES membrane, and loaded onto a 10 mL Sepharose® column. Exosomes were isolated from the rest of the plasma components through size exclusion chromatography by adding 1 mL increments of PBS to the Sepharose® column until the Fraction #4 eluent, containing plasma exosomes, is collected.

Figure 6A:
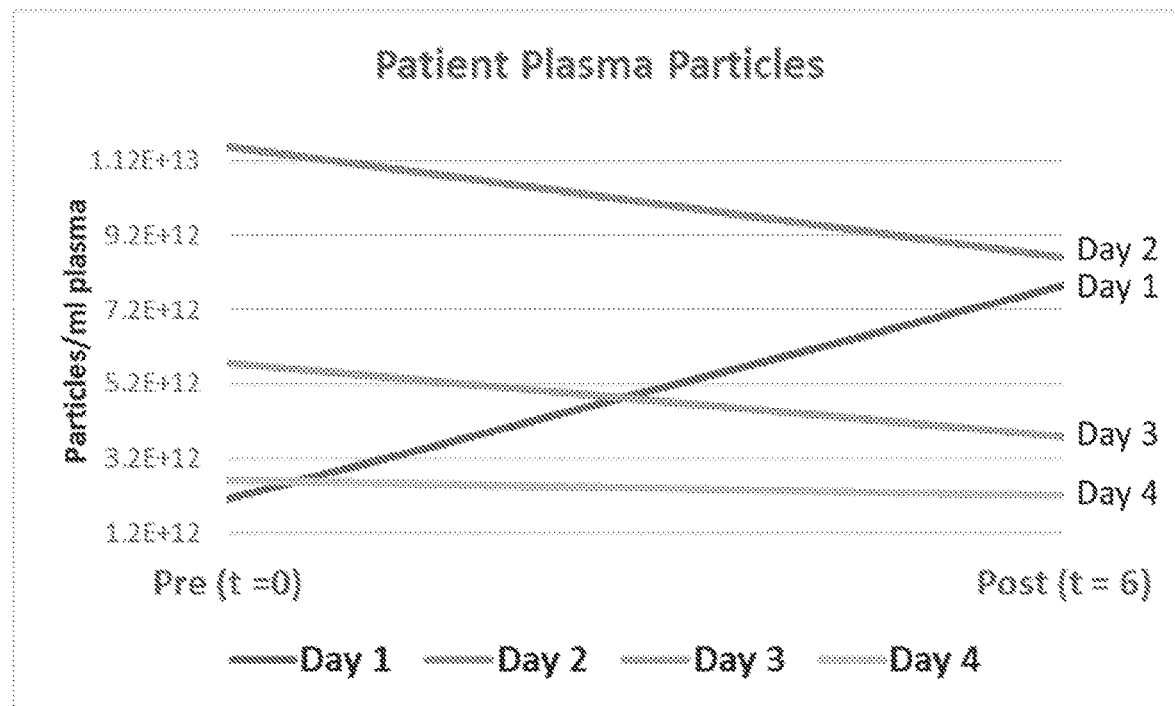
FIG. 6A depicts the decrease in nanoparticle concentration in unprocessed patient plasma after Hemopurifier® therapy. Pre (t=0) represents sample measurements before therapy, and Post (t=6) represents sample measurements after therapy.
Figure 6B:
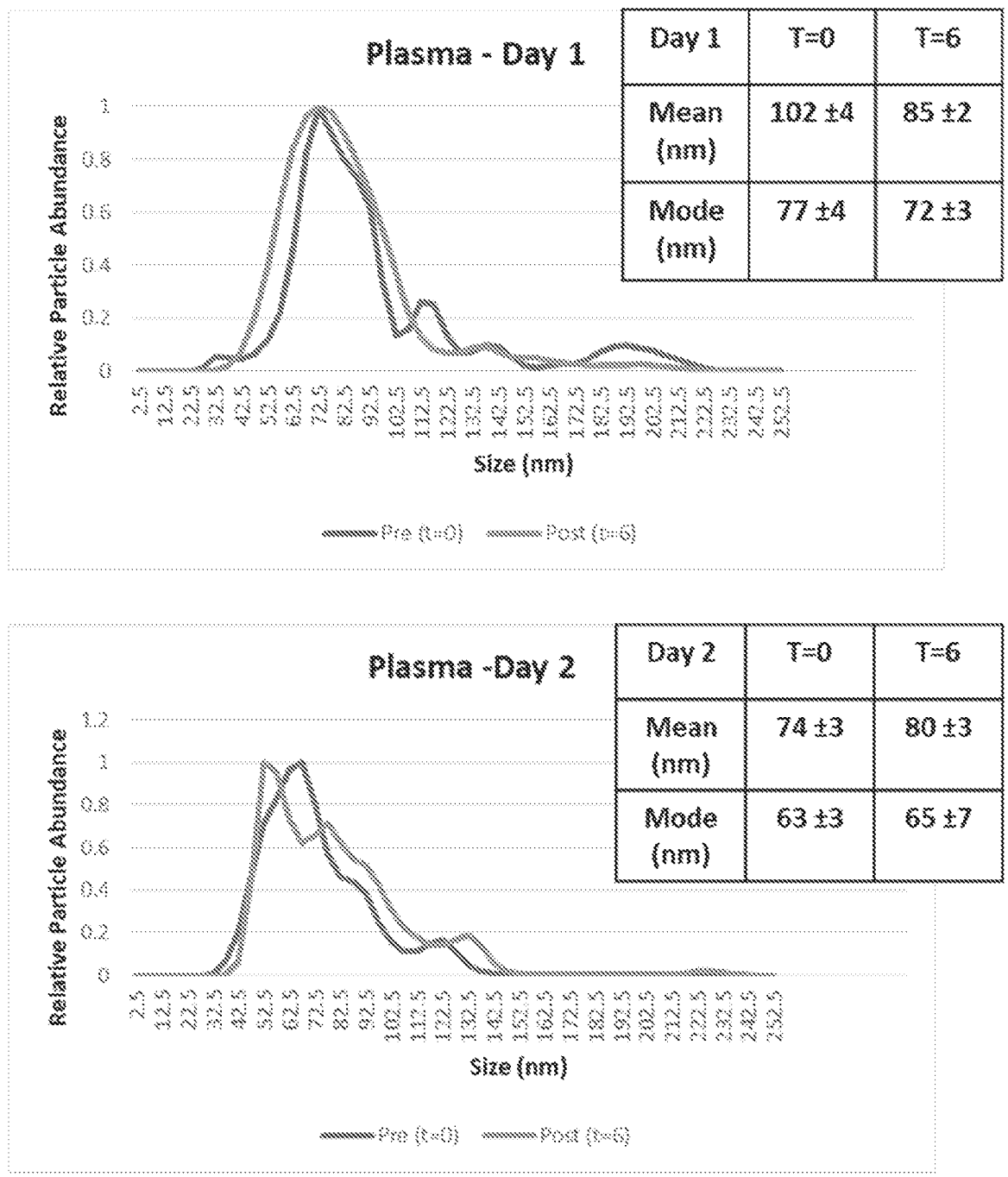
FIG. 6B depicts particle size populations in unprocessed patient plasma, which are generally unchanged after Hemopurifier® therapy. Pre (t=0) represents sample measurements before therapy, and Post (t=6) represents sample measurements after therapy.
Figure 6B:
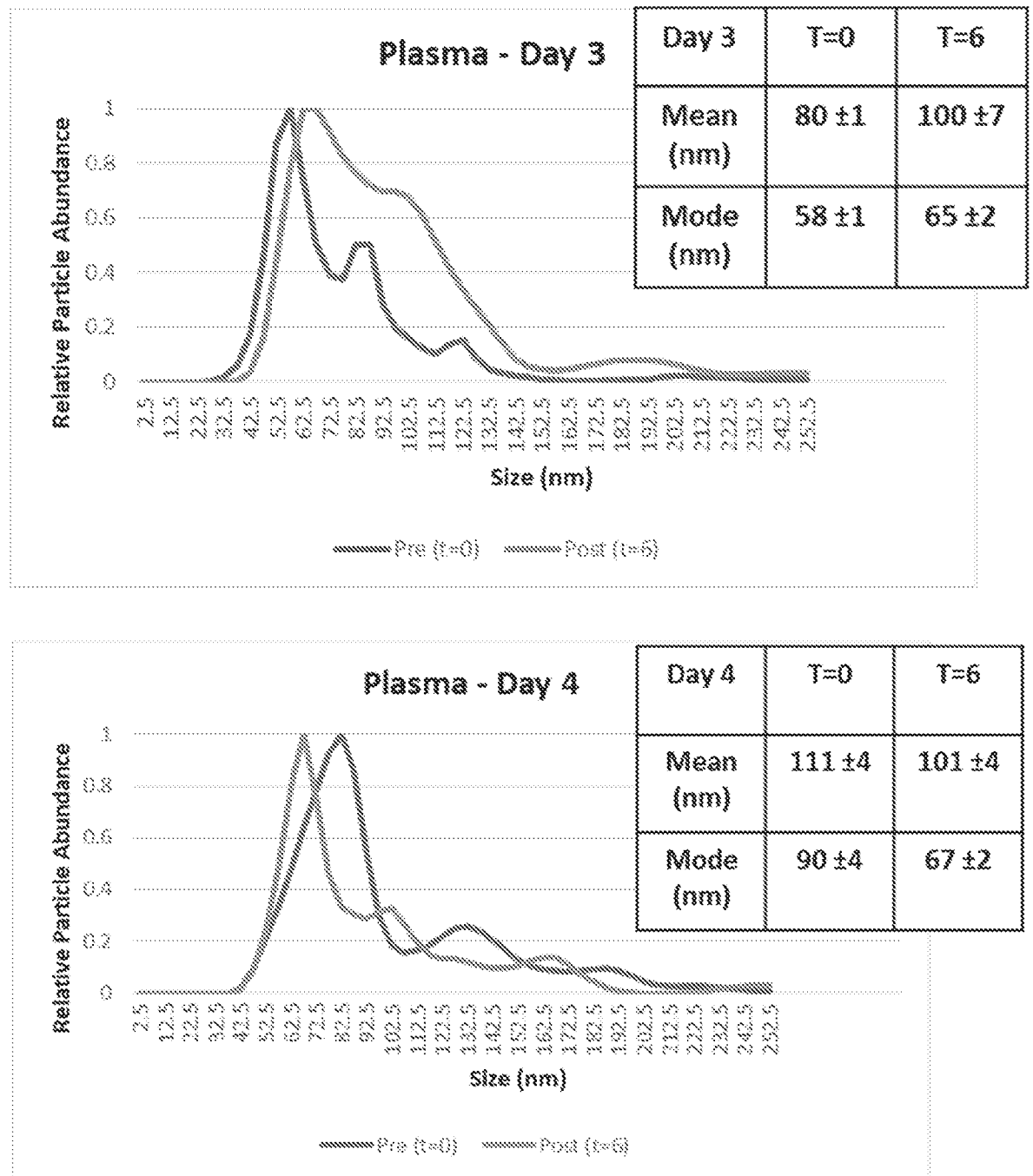

In order to obtain reliable quantification measurements, plasma exosome samples had to be diluted in 0.22 µM filtered PBS to a concentration of approximately $10^8$-$10^9$ exosomes/mL. Approximately 20-100 particles could be observed in the Nanosight field of view once exosome samples had been diluted to the appropriate concentration range. To improve detection of any smaller exosome populations that may be present in the plasma sample, nanoparticle tracking measurements were collected using a Camera Nanoparticle counts in unprocessed patient plasma was assessed for each pre- and post-therapy samples. Typically, overall nanoparticle counts decreased after treatment (FIG. 6A). Day 1 was suspected to be an outlier due to therapy interruption. However, relative particle sizes in the unprocessed plasma samples were unchanged by treatment (FIG. 6B).

Plasma samples were processed by mini-SEC and eluted in 8 fractions. Table 3 depicts the relative protein concentration (mg/mL) of each fraction by BCA assay. Fraction 4 was considered to contain purified exosomes. Day 1 post-therapy plasma had a protein content greater than the typical 60-80 mg/mL reported in the art (Leeman et al. *Anal. Bioanal. Chem.* (2018); 410:4867-73). Fraction 4 isolated exosomes represent about 0.1% of the total plasma proteins, which is consistent with exosome protein quantities reported in the art (Shtam et al. *J. Hematol.* (2018); 7:149-53). This data suggests that Hemopurifier® therapy has only a minor effect on overall plasma protein levels.

TABLE 3

Protein content of mini-SEC fractions of patient plasma (mg of protein/mL of plasma)

| | Day 1 T0 | Day 1 T6 | Day 2 T0 | Day 2 T6 | Day 3 T0 | Day 3 T6 | Day 4 T0 | Day 4 T6 |
|---|---|---|---|---|---|---|---|---|
| Unprocessed plasma | 62.5 | 103 | 52.5 | 48.75 | 56 | 50 | 63 | 59 |
| Fraction 3 | 0.002 | 0.002 | 0 | 0 | 0.002 | 0 | 0.003 | 0.007 |
| Fraction 4 | 0.063 | 0.077 | 0.0575 | 0.04 | 0.047 | 0.046 | 0.067 | 0.051 |
| Fraction 5 | 0.335 | 0.354 | 0.2125 | 0.16375 | 0.28 | 0.275 | 0.341 | 0.31 |
| Fraction 6 | 1.5 | 1.38 | 1.025 | 0.6375 | 1.02 | 1.15 | 1.36 | 1.2 |
| Fraction 7 | 4.1 | 3.76 | 2.7 | 1.85 | 2.94 | 3.12 | 3.77 | 2.99 |
| Fraction 8 | 8.1 | 7.4 | 36.25 | 28.75 | 8.36 | 8.59 | 9.24 | 9.99 |

Figure 7A:
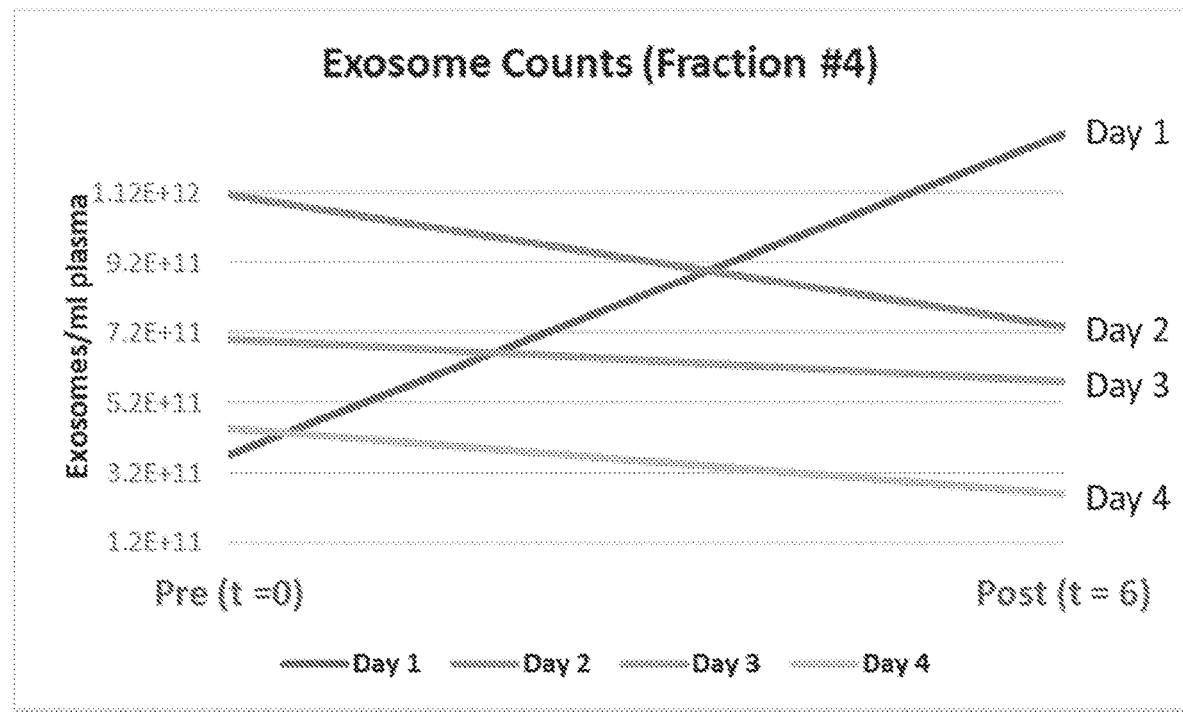
FIG. 7A depicts the decrease in circulating exosome concentration in a fractionated sample of patient plasma after Hemopurifier® therapy. Pre (t=0) represents sample measurements before therapy, and Post (t=6) represents sample measurements after therapy.

Exosome counts were quantified in Fraction 4 of each plasma sample. FIG. 7A shows that generally, exosome abundance remaining in the plasma was reduced following treatment. Day 1 was considered to be an outlier, possibly due to therapy interruption. This suggests that while Hemopurifier® therapy does not substantially reduce overall plasma protein content, it does deplete exosomes to a significant extent.

Figure 7B:
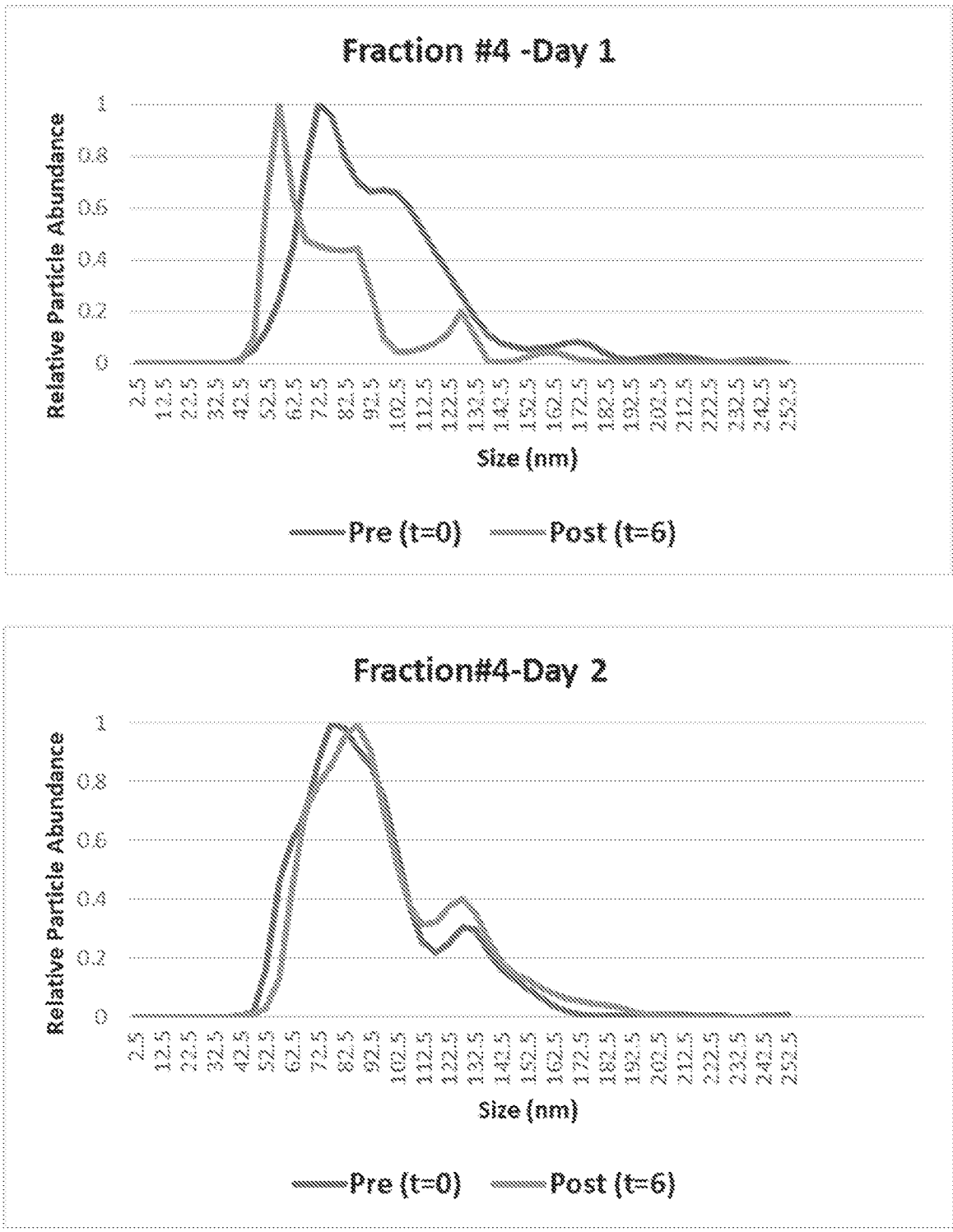
FIG. 7B depicts the size of exosome populations in a fractionated sample of patient plasma, which are generally unchanged after Hemopurifier® therapy. Pre (t=0) represents sample measurements before therapy, and Post (t=6) represents sample measurements after therapy.
Figure 7B:
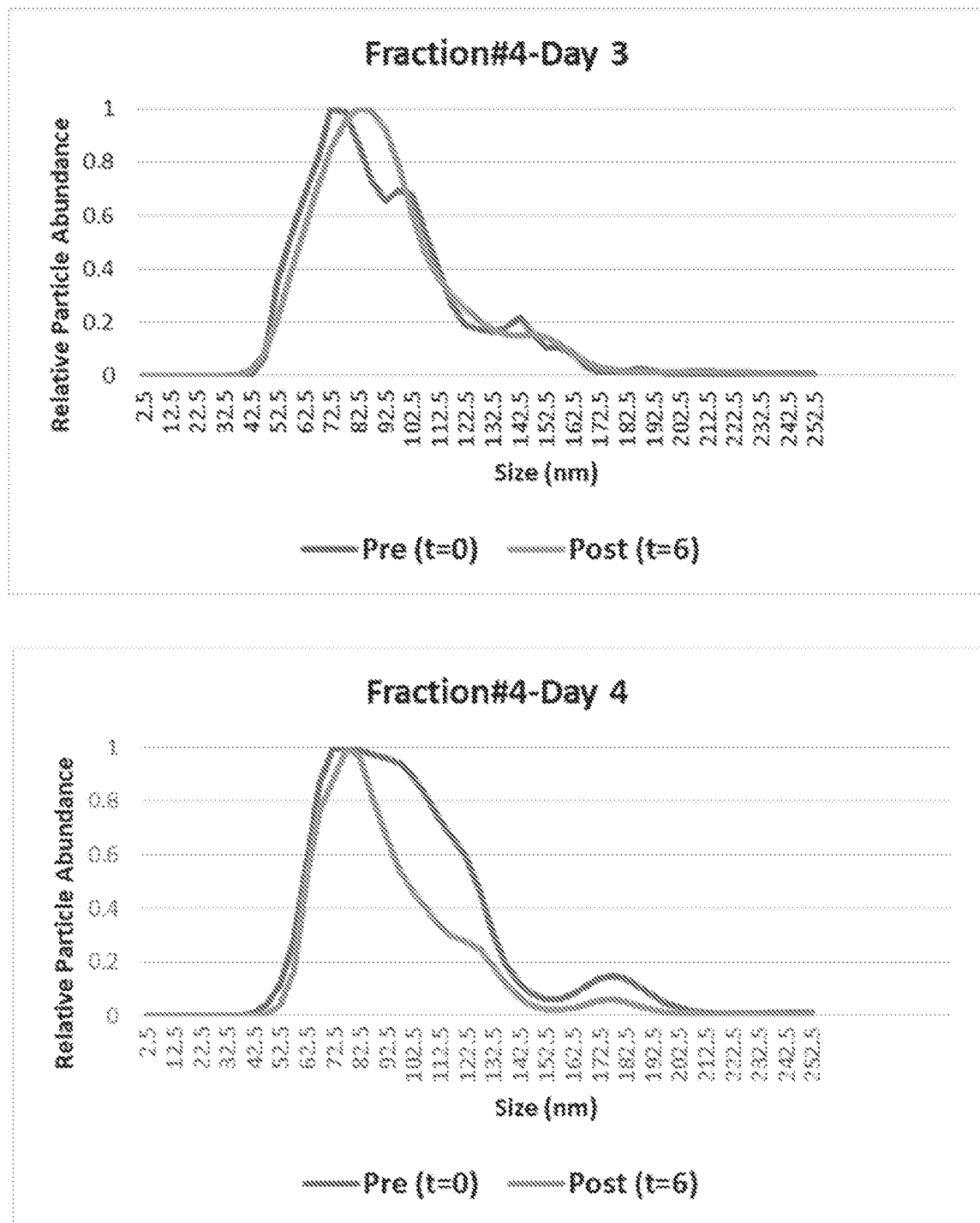

The relative sizes of the exosomes in Fraction 4 of each plasma sample was assessed. FIG. 7B demonstrates that the relative sizes of the circulating exosome populations are not altered by Hemopurifier® treatment.

Example 10: Purified Exosomes Contained miRNA that May be Associated with Disease Phenotypes As miRNAs are known to be associated with inflammation and disease, the miRNA content of the exosomes purified by mini-SEC from patient plasma samples (of Example 9) were assessed, both comparing pre- and post-therapy samples, as well as, to normal human plasma. The normal human plasma was processed in the same manner as the patient samples by mini-SEC and fraction 4 containing exosomes were analyzed. Table 4 identifies the miRNAs that were tested. miRNA was isolated from the plasma exosomes using a Qiagen miRNA easy isolation kit and incorporating an exogenous miRNA spike-in control. miRNA was reverse transcribed to a cDNA template using the TaqMan Advanced miRNA cDNA synthesis kit. Specific miRNA targets were amplified on a Quant 3 qPCR machine using specific TaqMan Advanced miRNA primer/probe sets (Thermo Fisher #A25576). Quantification of miRNA sequences was done by normalization to an exogenous spike-in cel-miR-39-3p miRNA control.

TABLE 4

Tested miRNAs (2 endogenous targets and 1 exogenous spike-in control)

| miRNA | Mature miRNA sequence | Comments |
|---|---|---|
| has-miR-424-5p | CAGCAGCAAUU CAUGUUUUGAA (SEQ ID NO: 1) | Inflammatory response, targets immune checkpoints, inversely associated with PD-L1 |
| hsa-miR-16-2-3p | CCAAUAUUACU GUGCUGCUUUA (SEQ ID NO: 2) | Upregulated in serum from patients with COVID-19 |
| cel-miR-39-3p (control) | UCACCGGGUGU AAAUCAGCUUG (SEQ ID NO: 3) | Spike-in exogenous normalization control |

Figure 8:
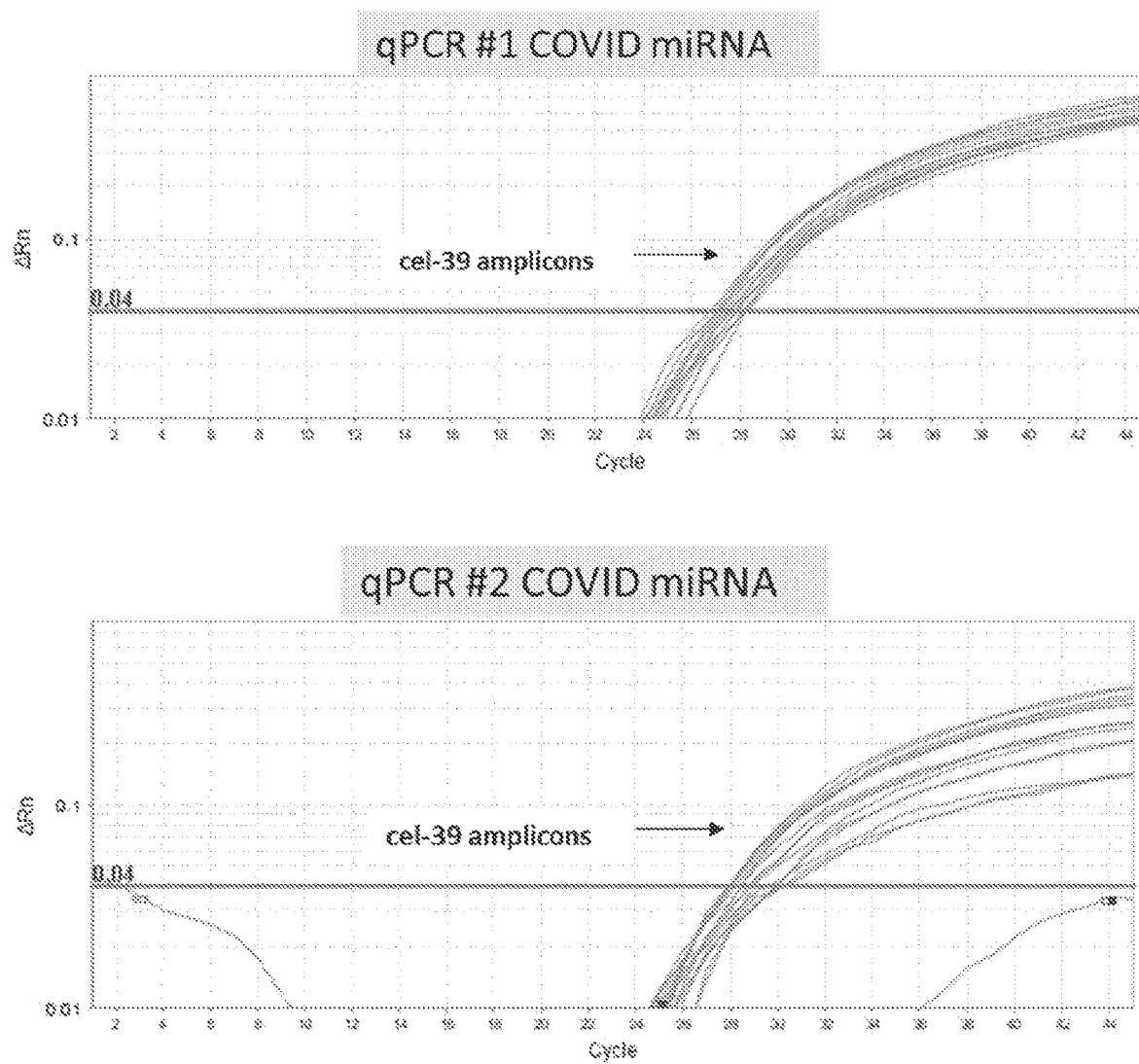
FIG. 8 depicts qRT-PCR amplification plots of *Caenorhabdits elegans* cel-miR-39-3p (cel-39) spiked into exosome fractions as a control.

Exogenous spike-in cel-miR-39-3p miRNA (cel-39) was added to every sample to control for variability introduced by the miRNA isolation process and subsequent synthesis of the cDNA template. The cel-39 control was used at $5.6 \times 10^8$ copies per sample. FIG. 8 shows the qRT-PCR amplification plots of the cel-39 spike-in control, and the limited range of inter-sample variability that must be controlled. Mean Ct value of all cel-39 amplicons was used to normalize the signal of the miRNA targets in each sample. The 2-ΔΔCt method (Livak & Schmittgen, Methods (2001) 25(4):402-8) was used to calculate the quantity of each miRNA relative to the spike-in cel-39 target. The quantity of miRNA measured in the exosomes was further normalized to reflect a starting sample volume of 1 mL of plasma.

Figure 9:
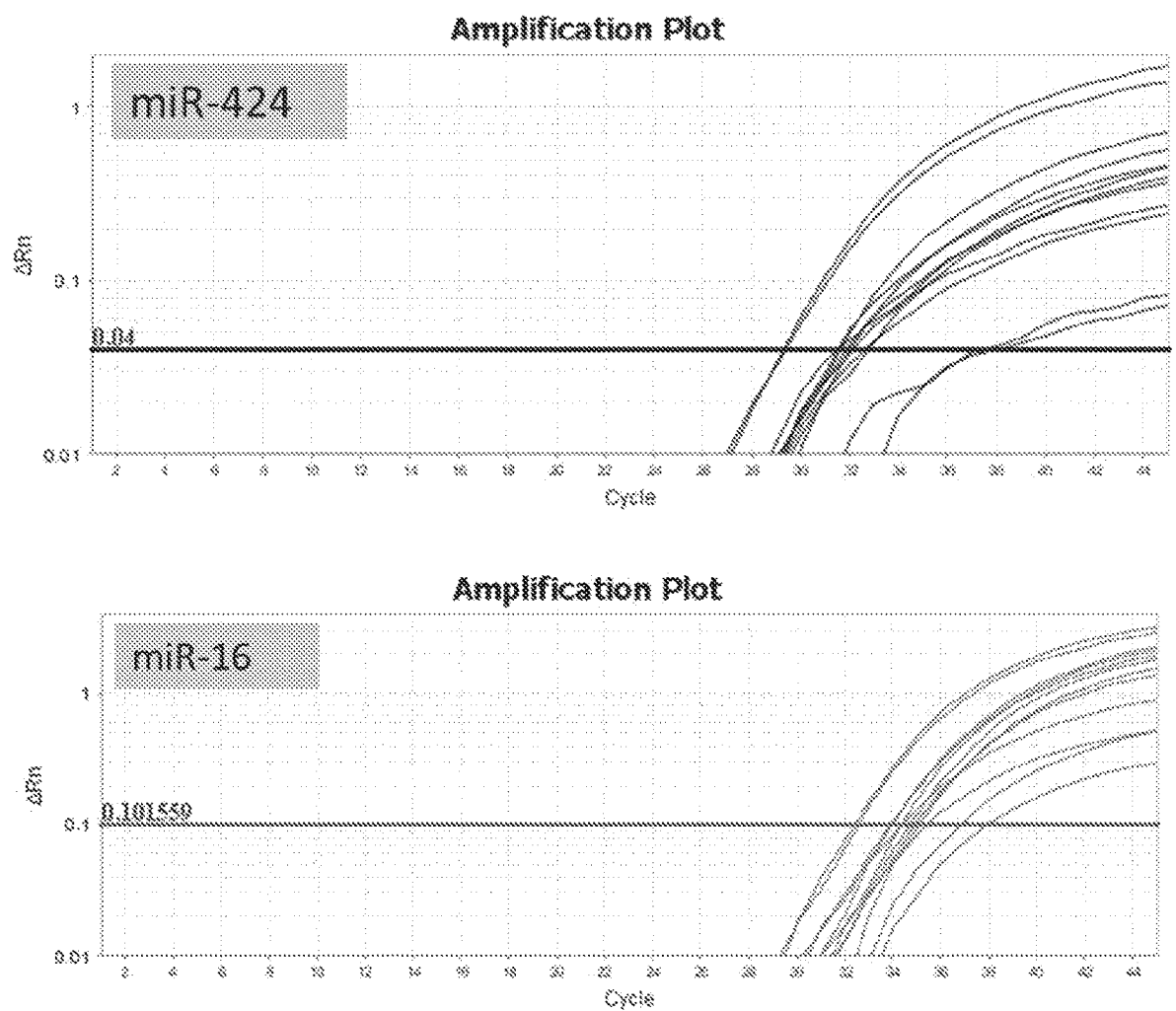
FIG. 9 depicts exemplary qRT-PCR amplification plots of the tested miRNA in exosome fractions of the patient plasma samples. The miRNA tested are human miR-424-5p (miR-424) and miR-16-2-3p (miR-16).
Figure 10:
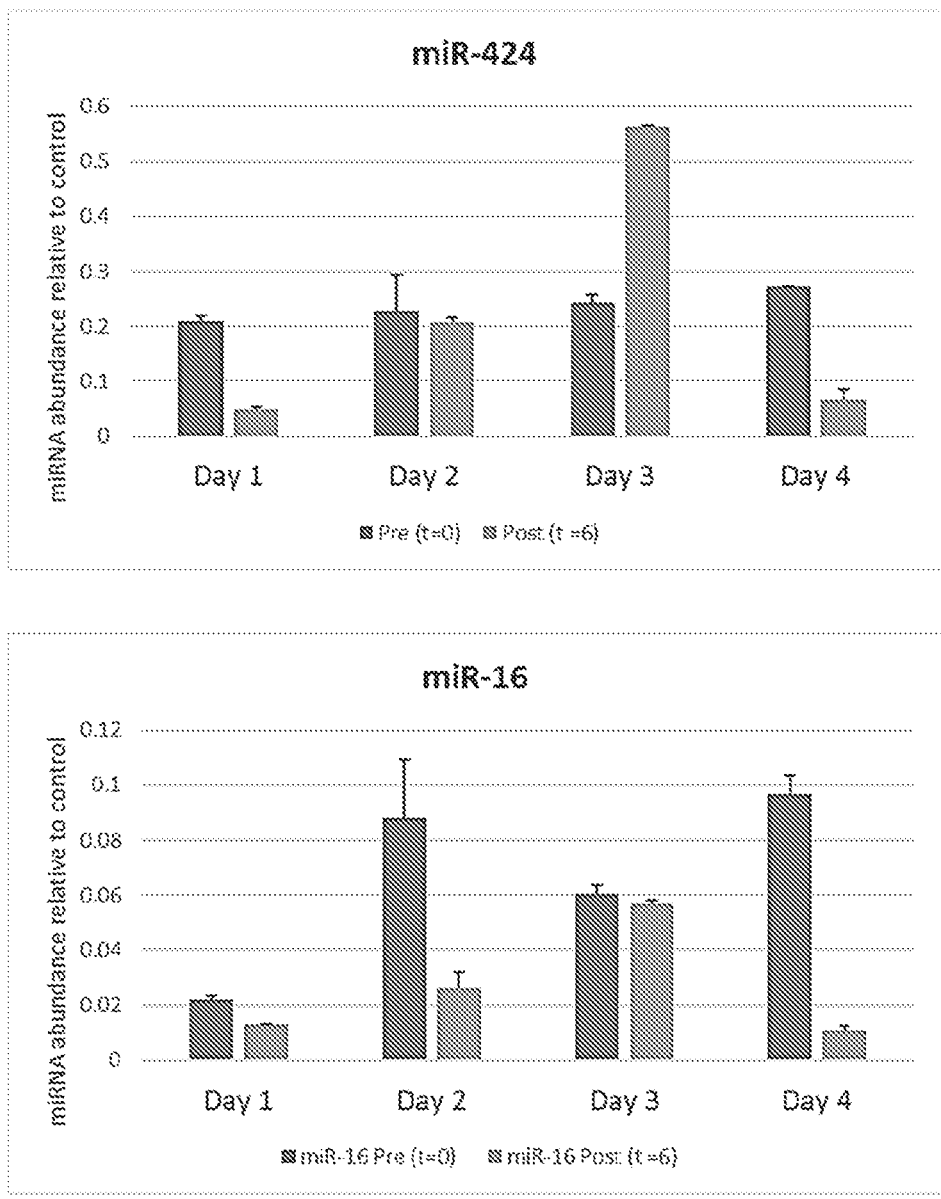
FIG. 10 depicts differences in miRNA abundance relative to control in exosome fractions of patient plasma samples before and after Hemopurifier® therapy.
Figure 11:
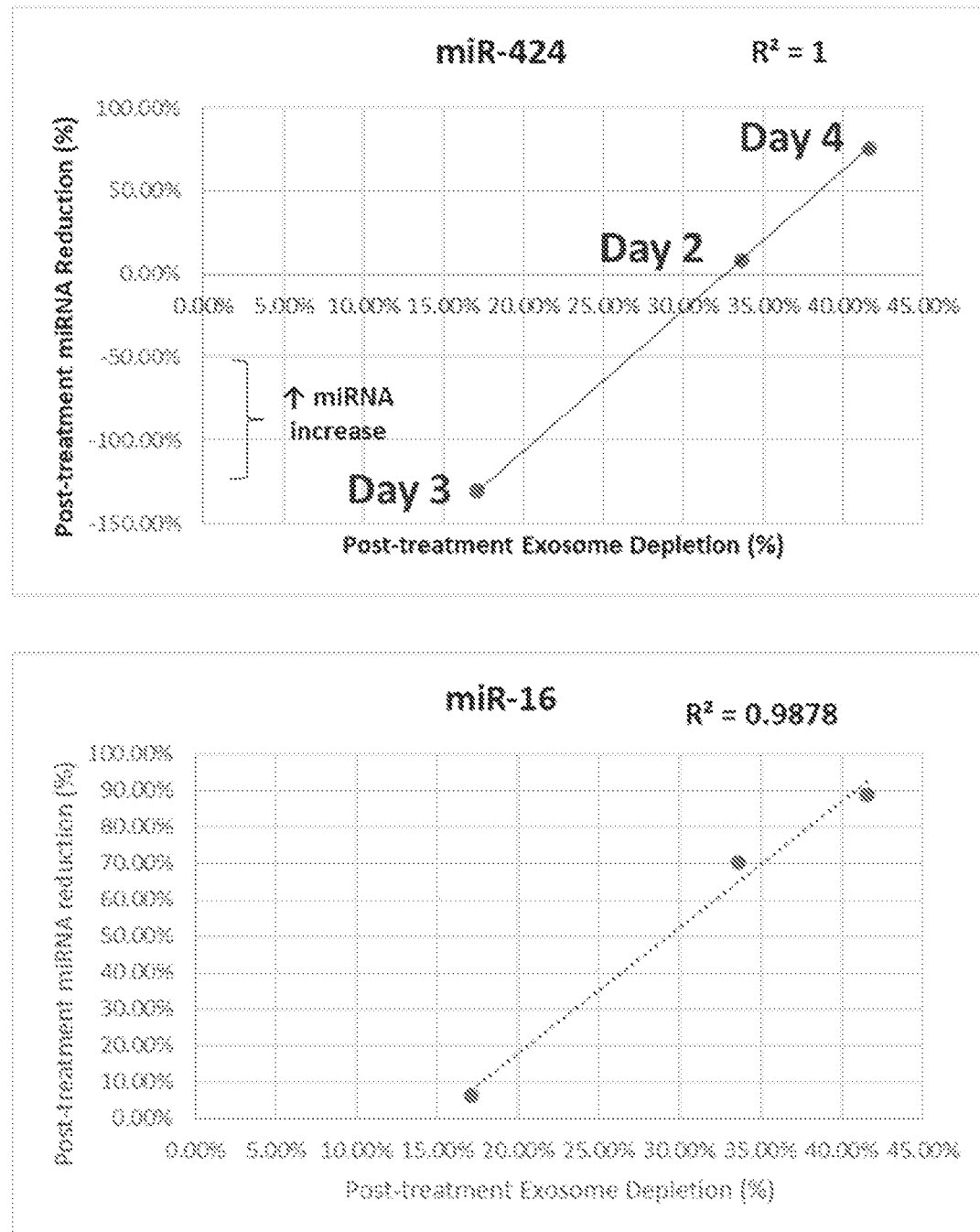
FIG. 11 depicts a correlation between therapy-associated exosome depletion and miRNA reduction (days 2-4 were tested).

Each of the tested miRNA in fraction 4 of the COVID-19 patient and human control plasma samples were quantified by qRT-PCR. FIG. 9 shows exemplary qRT-PCR amplification plots for the miRNA, and how their signal intensity reflecting abundance can vary in samples collected at distinct time points of the therapy. The relative abundance of the miRNA for samples of days 1-4 are shown in FIG. 10. In general, a decrease in abundance of the tested miRNA is observed in the post-treatment exosome samples relative to pre-treatment exosomes samples, suggesting that Hemopurifier® therapy depletes exosomes containing these miRNAs. FIG. 11 shows that miRNA abundance reduction is directly proportional to exosome depletion in the samples during some of the initial days of therapy.

Figure 12A:
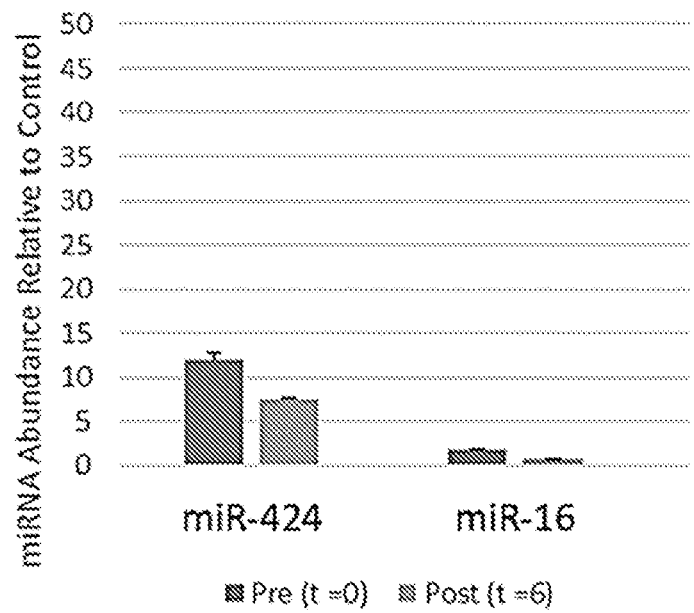
FIG. 12A depicts miRNA abundance relative to control in day 4 whole plasma samples from the COVID-19 patient.
Figure 12B:
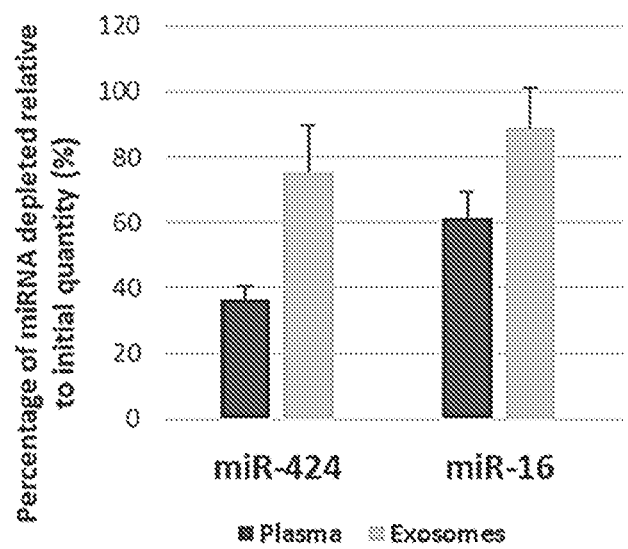
FIG. 12B depicts a proportional reduction of initial miRNA content that is larger in the processed exosome fraction compared to unprocessed plasma of the COVID-19 patient.

To compare the relative abundance and depletion of the tested miRNA in the exosome fractions and unprocessed plasma, miRNA of the day 4 whole plasma samples of the COVID-19 patient was quantified (FIG. 12A). Depletion of the miRNA was similarly observed in the post-treatment whole plasma samples, and both miR-424-5p and miR-16-2-3p were depleted to a greater extent in the exosome fraction compared to whole plasma (FIG. 12B). Overall, this indicates that miRNAs are found in various forms (e.g. as exosome cargo, associated with other biological structures, or as free floating nucleic acids) in plasma, and the Hemopurifier® cartridge with GNA lectin is able to deplete all types to an extent. Yet, the greater depletion observed in the exosome fraction indicates that these miRNAs are more selectively eliminated through the GNA lectin's ability to capture exosomes with pathological characteristics.

Figure 13A:
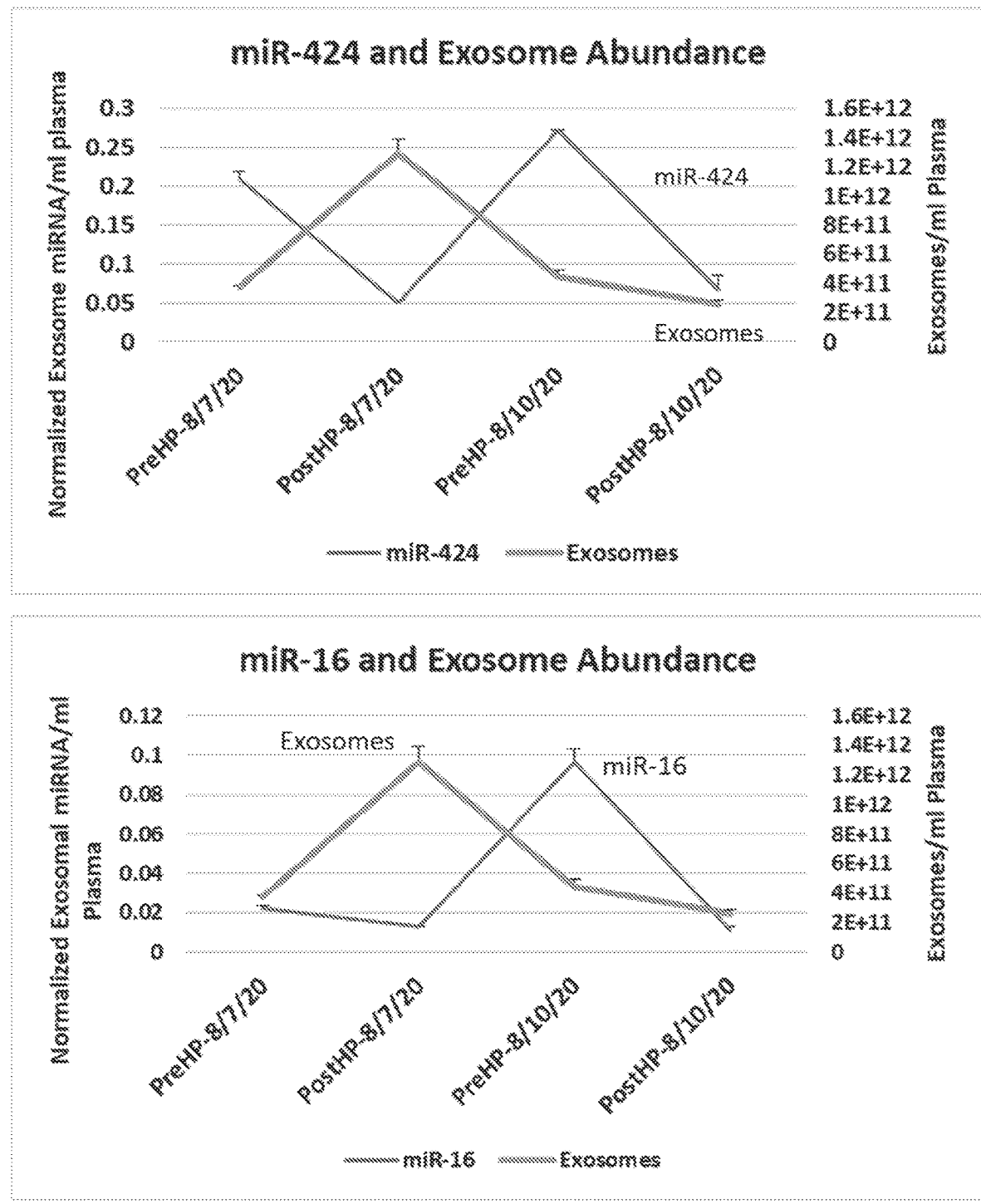
FIG. 13A depicts abundance of miRNAs miR-424 and miR-16, and exosome abundance in patient samples from days 1 and 4 of treatment.
Figure 13B:
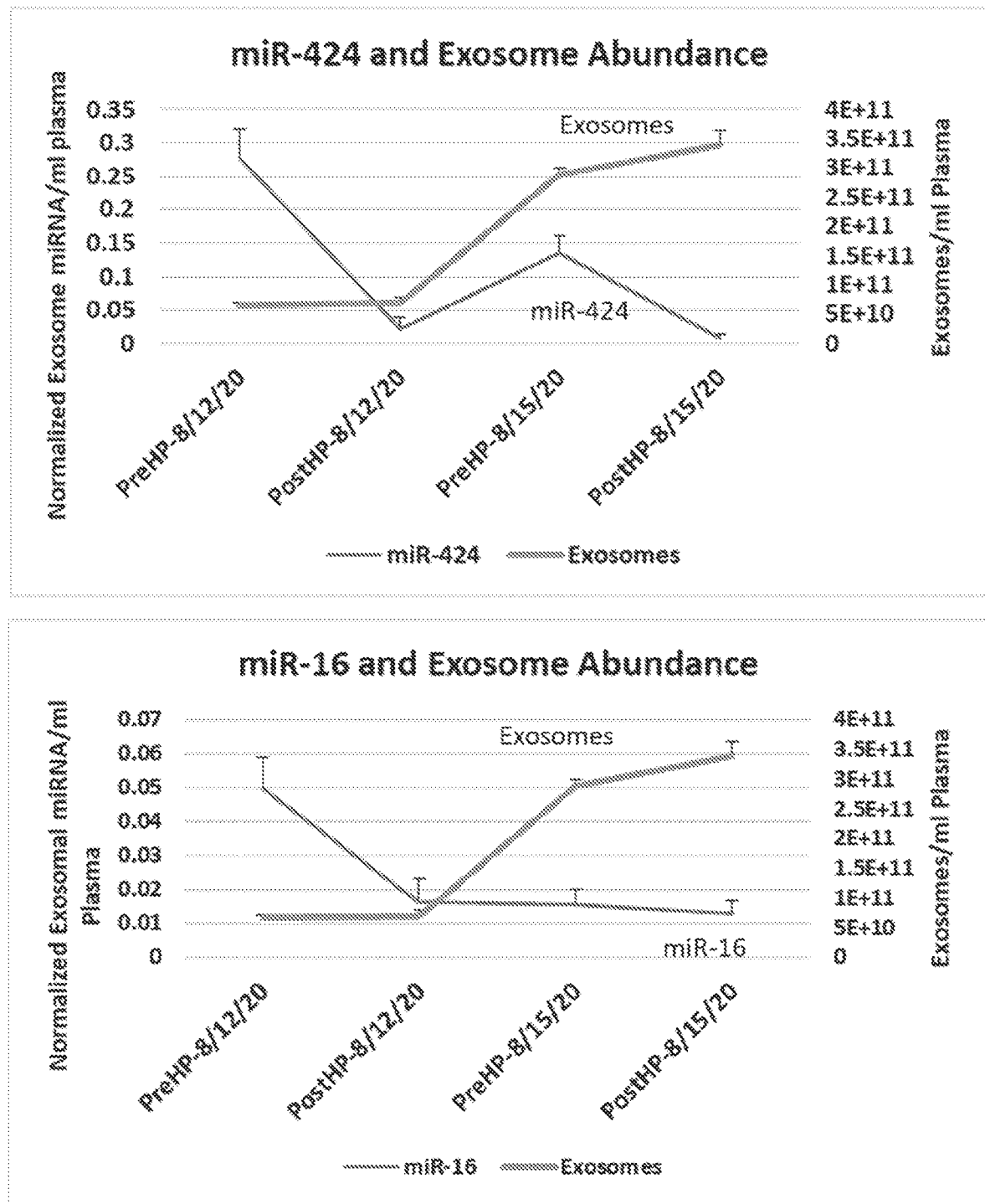
FIG. 13B depicts abundance of miRNAs miR-424 and miR-16, and exosome abundance in patient samples from days 5 and 8 of treatment.

After analysis of the days 1-4 samples, exosomes were isolated and analyzed for the day 5 and day 8 plasma samples, as well. There was a two day gap in between day 4 and day 5 of therapy during which a second emergency use authorization was obtained. FIG. 13A shows abundance of 1) miR-424 and miR-16 found in exosomes isolated from plasma, and 2) exosomes in plasma for the day 1 (Aug. 7, 2020) and day 4 (Aug. 10, 2020) plasma samples. FIG. 13B shows the same for the day 5 (Aug. 12, 2020) and day 8 (Aug. 15, 2020) plasma samples. A consistent decrease in miR-424 and miR-16 abundance is observed following Hemopurifier® therapy, as evident by the pre- and post-treatment samples from each day.

In summary, the Hemopurifier® device is capable of removing pathological miRNAs through the capture of disease promoting exosomes, regardless of the overall exosome counts pre- and post-treatment. The miRNAs miR-424 and miR-16, which have been associated with COVID-19-associated coagulopathy and acute lung injury, are able to be depleted from the circulating blood of a patient with acute COVID-19.

Example 11: Isolation of Bound Material from Hemopurifier® Cartridges

Disclosed in this example are additional details describing methods for eluting a Hemopurifier® cartridge of bound virus and exosomes, and extracting material such as proteins and nucleic acids following treatment of a human subject. In the case of viral genomic material, the samples can then be processed using qPCR to assess viral concentration.

Used Hemopurifiers® may be stored on ice or at −20° C. until processing. However, immediate shipping and processing is preferable. Devices are to be shipped and handled in a labeled biohazard bag that is inside a larger secondary bag. Upon receipt, the sealed devise should immediately be placed into refrigerated storage at 2° C. to 8° C.

When the Hemopurifier® is ready for processing, 250-300 mL of sterile saline or filtered PBS is prepared for rinsing fluid. The device is placed vertically into a clamp on a ring stand or other stabilizing apparatus. The top twist lock cap from the top blood port of the Hemopurifier® device is disconnected. MPC-850-16 and MPC-865 tubing is attached. A syringe is filled with the rinsing fluid and the syringe is connected to the open end of the MPC-865 tubing. The Hemopurifier® is then rotated so that the other end is facing up, and the twist lock cap is disconnected from the other blood port. MPC-875 tubing is attached. The open end of the MPC-875 tubing is placed into the proper biohazard waste receptacle, and the device is reoriented so that the open end of the tubing can remain in the waste receptacle while rinsing the device. The rinsing fluid is slowly pushed through the Hemopurifier® and into the waste receptacle. This is repeated 2-3 times. Fluid exiting the device should not be red but may still have a slight pink color. Then, the syringe is filled with air, which is pushed through the device, forcing residual fluid out of the Hemopurifier® and into the waste receptacle. Repeat 2-3 times to remove as much fluid as possible prior to storing the device. When finished, the tubing is disconnected and disposed in the proper biohazard container. The blood port caps are reattached and the device can be stored at −20° C.

Figure 14:
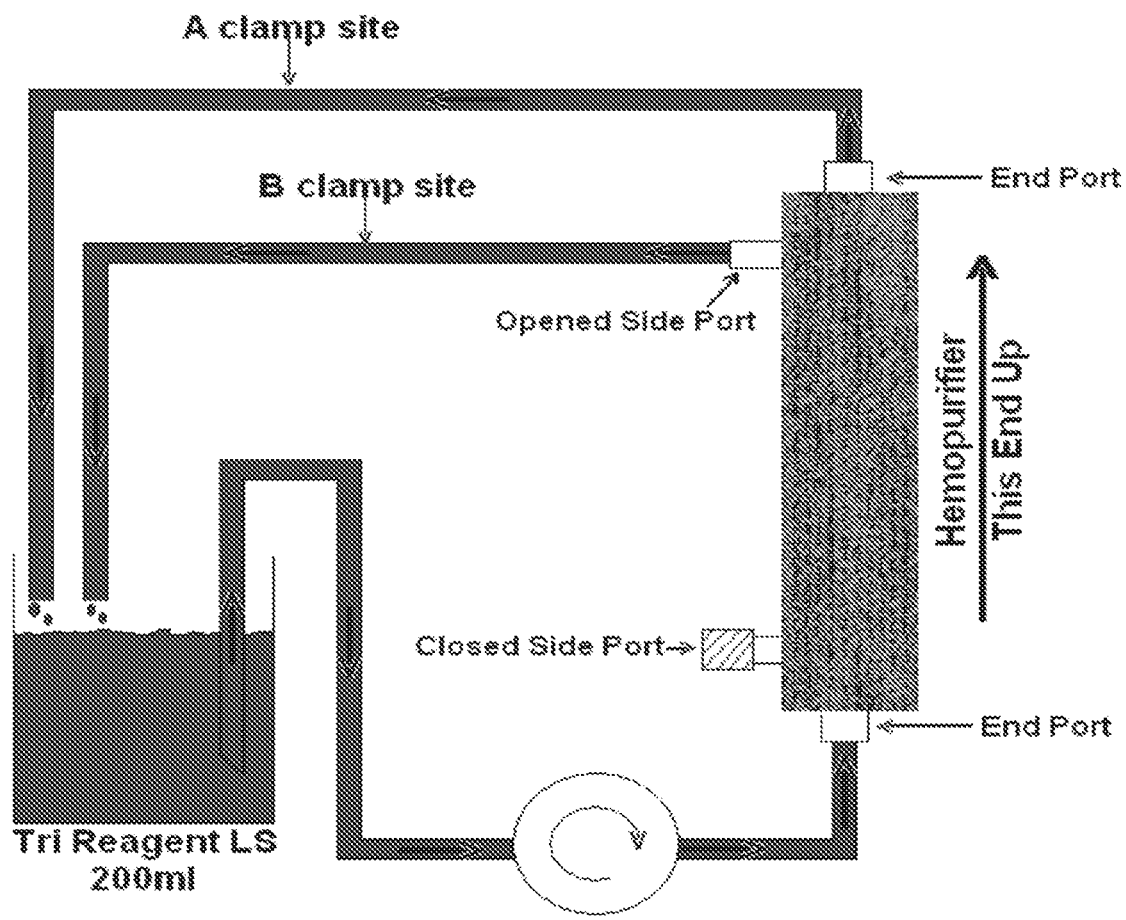
FIG. 14 depicts an exemplary schematic for eluting bound material from a Hemopurifier® device.

Elution circuit set-up: The Hemopurifier® is removed from the biohazard bag and placed on an adsorbent towel or pad. The device is allowed to equilibrate to room temperature (15-20 minutes). Both twist lock caps are unscrewed from the blood ports; one of the luer lock caps from the side dialysate ports is also unscrewed. All removed caps should be kept for reattachment following the elution procedure. Tubing with a twist lock is attached to the end port of the cartridge. The other end of this tubing is placed into a glass flask or bottle, making sure that the tube reaches near the bottom. Another piece of tubing with a twist lock is attached to the other end-port of the cartridge, placing its other tubing end in the glass container. A drain tube with a male luer fitting is attached to the open side-port of the device, placing the other tubing end in the glass container. Once all tubes are securely attached and in place, tube clamps or hemostats are attached to all of the tubing. The Hemopurifier® is then mounted in vertical position using a ring stand/holder, ensuring that the open side port is on top. See FIG. 14 for an exemplary schematic of this set up.

Alpha-methylmannoside (a-MM) elution: A 200 mL solution of 1M alpha-methylmannoside (a-MM) in 1×PBS is prepared. The a-MM solution is added to the glass container holding the tubing. A pump is started to flow the a-MM solution at a rate of 50 mL/min through the Hemopurifier® cartridge. The solution should drain out of one or both upper drain ports. Once the cartridge is filled with a-MM solution, the tubing attached to the outlet blood port is clamped ("A clamp site") and the a-MM solution is allowed to flow through the fibers and extra-lumen space of the cartridge for 20 minutes. After this, the clamp is removed, and the side port tubing is clamped ("B clamp site") to allow the a-MM solution to flow through the fiber lumen of the cartridge for 20 minutes. When the circulation is finished, the remaining a-MM solution is drained from both the fibers and extra-lumen space of the cartridge. The eluate can be quantified or stored frozen at −20° C. for later use.

TRI reagent/TRIzol® extraction: Immediately following the a-MM elution, all of the tubing ends are placed into a glass container containing 200 mL of TRI Reagent® or TRIzol®. This process should be performed in a fume hood or appropriate biosafely cabinet. Once all of the tubes are securely in place, a pump is started to flow the TRI Reagent® at a rate of 50 mL/min through the Hemopurifier® cartridge. The solution should drain out of one or both upper drain ports. Once the cartridge is filled with the solution, the lumen outlet drain tube is clamped ("A clamp site") and the solution is allowed to flow through the fibers and extra-lumen space of the cartridge for 20 minutes. The TRI® reagent solution will begin to melt the fibers in the cartridge, and some of the tubing connectors. The system should be observed frequently for leaks. The resin material can clog the tubing. Circulation should be checked often to ensure consistent flow throughout the system. The tubing path should be adjusted to avoid clogging of the inlet tubing. If a clog occurs, the pump should be stopped and the clog should be cleared, replacing the tubing if necessary. The A clamp site clamp can be removed, and the B clamp site can be clamped to allow the solution to flow through the lumen of the cartridge for 20 minutes. When circulation is finished, the remaining reagent should be drained from both the fibers and extra-lumen space of the cartridge. The eluate can be quantified or stored at −20° C. for later use.

Final rinse: Immediately following the TRI Reagent® step, all tubing ends are placed into a glass container containing 200 mL of fresh 1×PBS. This rinse is flowed through the cartridge at a rate of 50 mL/min for 5 minutes. When circulation is finished, the remaining buffer solution is drained from both the fibers and extra-lumen space of the cartridge. A sample of the rinse buffer is stored at −20° C. All tubing is removed and all ports of the cartridge are capped. Everything is discarded in an appropriate biohazard waste receptacle.

Example 12: Overview of Use of the Hemopurifier® for a Second Acute COVID-19 Patient On Jan. 14, 2021, the Hemopurifier® device was approved for a single patient under emergency use. The subject was a 67 year old male with a history of Tetralogy of Fallot repair, coronary artery disease, and newly diagnosed diabetes mellitus. He presented to the hospital with a 1 week history of cough and shortness of breath. He was found to be COVID-19 positive by PCR and was admitted to the hospital. The patient was also noted to have acute kidney injury. Despite treatment with remdesivir, dexamethasone, baricitinib, convalescent plasma, and full dose anticoagulation, the patient developed worsening multiple organ system failure. He was on mechanical ventilation with a fraction of inspired oxygen (FIO2) of 100% and positive end-expiratory pressure (PEEP) of 12 cmH2O, a single vasopressor for hypotension and CRRT for acute renal failure. Given the patient's deterioration, the Hemopurifier® device was approved for emergency use for "filtration of viral components as well as exosomes in the bloodstream".

The subject completed one 6 hour and 15 minute Hemopurifier® therapy. A total of 4 investigational devices were originally provided to the hospital. Of the 4 devices provided, 1 device was used and subsequently processed.

Figure 15A:
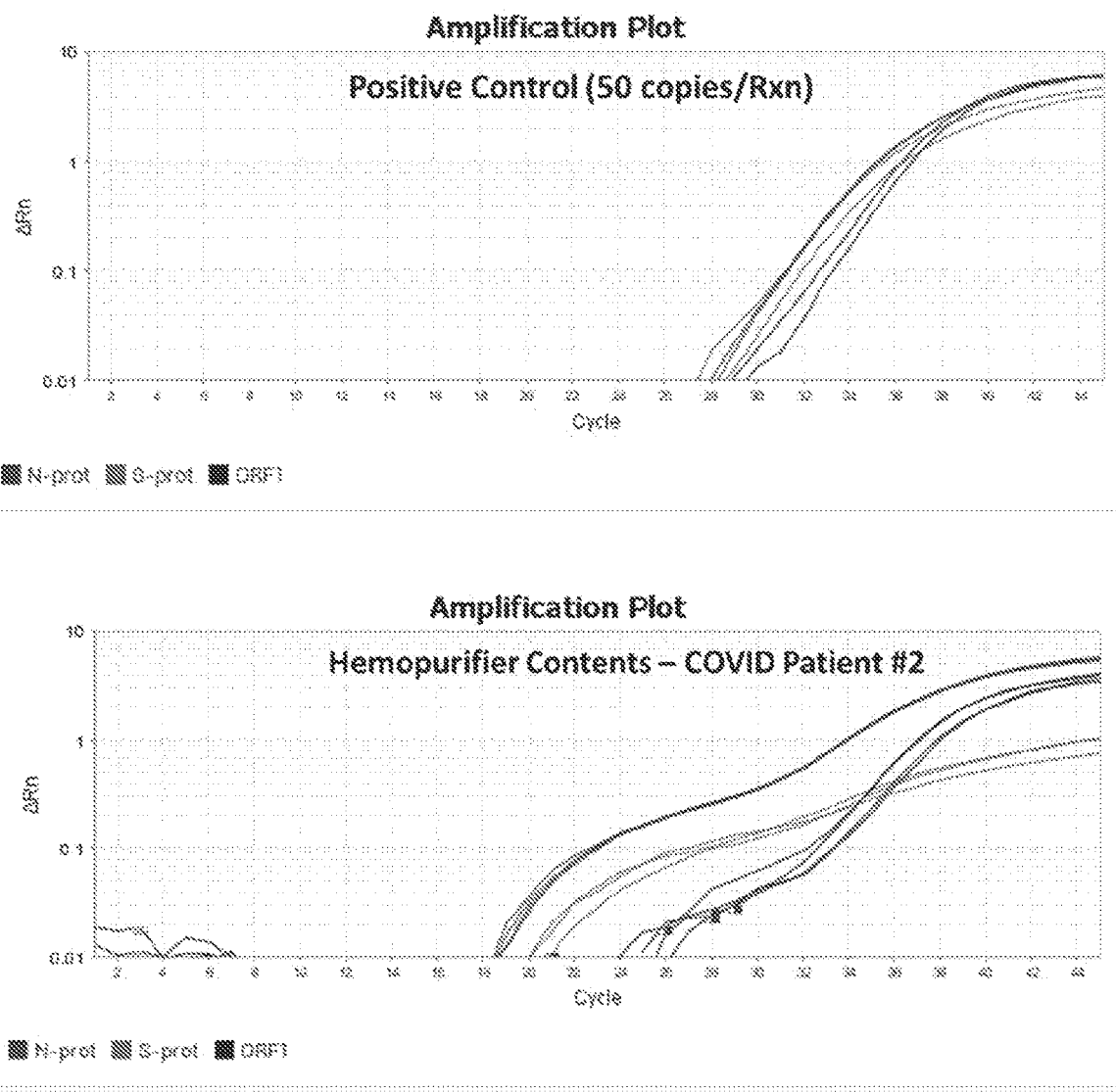
FIG. 15A depicts amplification of SARS-CoV-2 specific genetic targets from a template obtained from an eluate of a Hemopurifier® device used on a COVID-19 patient.

As shown in FIG. 15A, positive amplification of 3 distinct SARS-CoV-2 viral genomic regions is observed using the TRIzol® eluted Hemopurifier® contents. Table 5 shows the cycle threshold (Ct) quantification. Ct values <37 are considered positive for the presence of the SARS-CoV-2 virus.

TABLE 5

| | SARS-CoV-2 amplification Ct values | |
|---|---|---|
| Viral gene | Control (50 copies/ reaction) | Sample from Hemopurifier® after COVID patient treatment |
| N protein | 34.2 ± 0.07 | 32.4 ± 0.04 |
| S protein | 31.8 ± 0.48 | 28.8 ± 0.71 |
| ORF1ab | 34.9 ± 0.3 | 35.5 ± 0.51 |

Figure 15B:
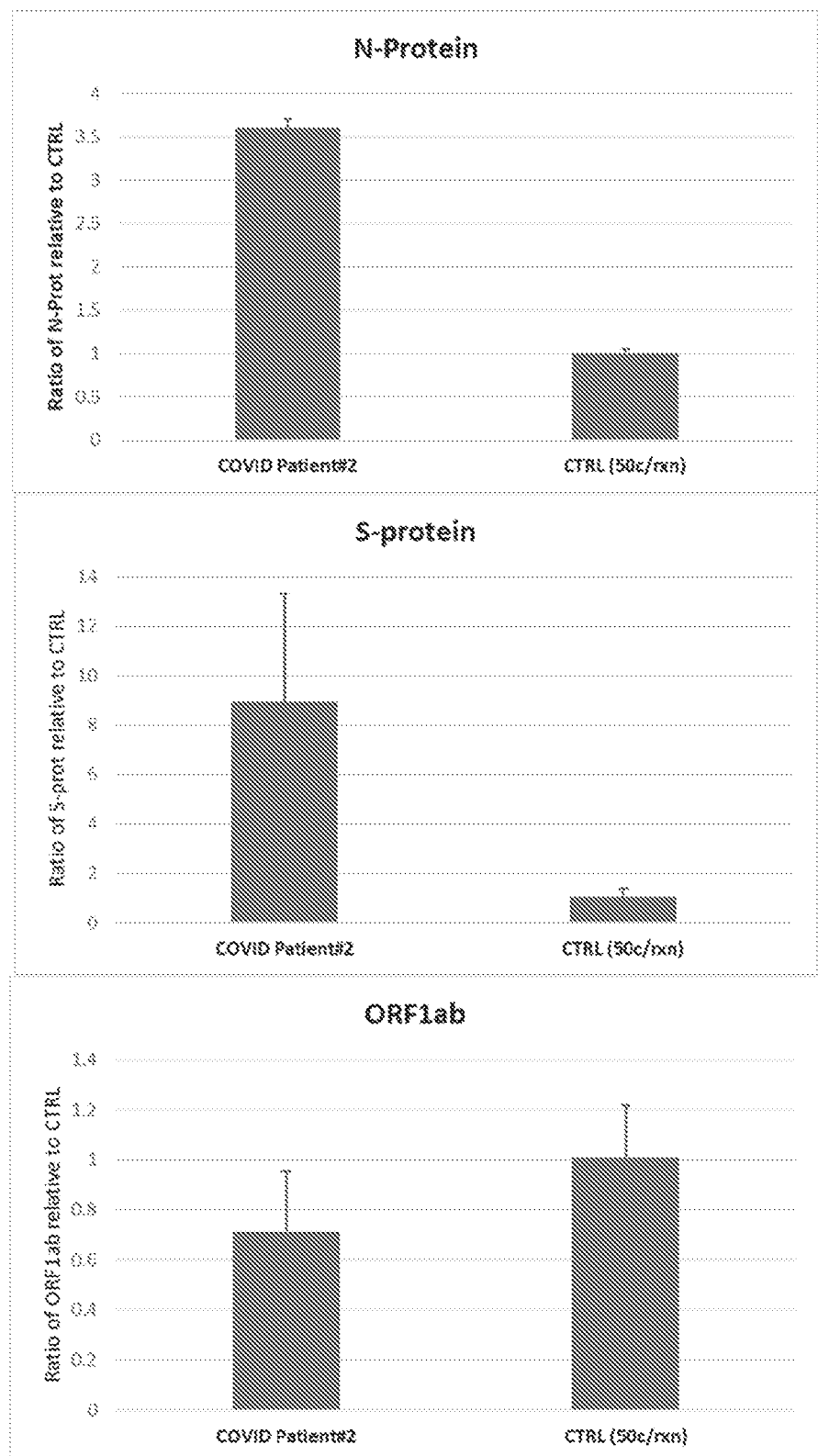
FIG. 15B depicts variability in amplification of three distinct SARS-CoV-2 genetic targets from the Hemopurifier® eluate target.

The 2-ΔΔCt method (Livak & Schmittgen, Methods (2001) 25(4):402-8) was used to calculate the quantity of each viral gene target relative to a positive control containing a known copy number. As shown in FIG. 15B, each of the three SARS-CoV-2 targets amplified from the Hemopurifier® eluate at different ratios relative to the control. While the N protein and S protein targets amplified at higher levels than the control, suggesting a higher abundance of these SARS-CoV-2 viral targets in the isolated sample, the ORF1ab target did not amplify as well.

In summary, the second COVID-19 patient described in this example may have had intact SARS-CoV-2 virions circulating through their blood stream based on the positive amplification of SARS-CoV-2 genes from samples eluted from the Hemopurifier® device used to treat the patient. This demonstrates that either SARS-CoV-2 viral particles, or fragments containing the RNA genetic material were adsorbed onto the GNA lectin affinity resin, and the TRIzol® flush eluted the captured contents. It was possible to detect the presence of the SARS-CoV-2 genome in RNA purified from 1 mL of the eluate. Distinct quantities of the three viral genomic targets detected in amplification could be result of viral or genomic fragmentation, capture of other circulating nanoparticles containing viral genomic contents, distinct GNA lectin adsorption or elution profiles, or the presence of PCR inhibitors in the purified RNA samples.

It is to be understood that this invention is not limited to particular formulations or process parameters, as these may, of course, vary. It is also to be understood that the terminology used herein is for the purpose of describing particular embodiments of the invention only, and is not intended to be limiting. Further, it is understood that a number of methods and materials similar or equivalent to those described herein can be used. Any feature or combination of features described herein are included within the scope of the present invention provided that the features included in any such combination are not mutually inconsistent as will be apparent from the context, this specification, and the knowledge of one of ordinary skill in the art. The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"), the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description or claims, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc.

As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

The contents of all cited references, including literature references, issued patents, published patent applications, and co-pending patent applications, cited throughout this application are hereby expressly incorporated by reference in their entirety. Those skilled in the art will recognize, or be able to ascertain using no more than routine experimentation, many equivalents to the specific embodiments of the invention described herein. Such equivalents are intended to be encompassed by the appended claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERENCES

Ambros V. microRNAs: tiny regulators with great potential. Cell 2001; 107(7): 823-6.

Brennecke J, Stark A, Russell R B, Cohen S M. Principles of microRNA-target recognition. PLoS Biol 2005; 3(3): e85.

Valadi H, Ekstrom K, Bossios A, Sjostrand M, Lee J J, Lotvall J O. Exosome-mediated transfer of mRNAs and microRNAs is a novel mechanism of genetic exchange between cells. Nat Cell Biol 2007; 9(6): 654-9.

Nik Mohamed Kamal N, Shahidan W N S. Non-Exosomal and Exosomal Circulatory MicroRNAs: Which Are More Valid as Biomarkers? Front Pharmacol 2019; 10: 1500.

Turchinovich A, Weiz L, Langheinz A, Burwinkel B. Characterization of extracellular circulating microRNA. Nucleic Acids Res 2011; 39(16): 7223-33.

Kosaka N, Yoshioka Y, Hagiwara K, Tominaga N, Katsuda T, Ochiya T. Trash or Treasure: extracellular microRNAs and cell-to-cell communication. Front Genet 2013; 4: 173.

Janas T, Janas M M, Sapon K, Janas T. Mechanisms of RNA loading into exosomes. FEBS Lett 2015; 589(13): 1391-8.

O'Neill L A, Sheedy F J, McCoy C E. MicroRNAs: the fine-tuners of Toll-like receptor signalling. Nat Rev Immunol 2011; 11(3): 163-75.

Cullen B R. MicroRNAs as mediators of viral evasion of the immune system. Nat Immunol 2013; 14(3): 205-10.

Trobaugh D W, Klimstra W B. MicroRNA Regulation of RNA Virus Replication and Pathogenesis. Trends Mol Med 2017; 23(1): 80-93.

Haasnoot J, Berkhout B. RNAi and cellular miRNAs in infections by mammalian viruses. Methods Mol Biol 2011; 721: 23-41.

Mishra R, Kumar A, Ingle H, Kumar H. The Interplay Between Viral-Derived miRNAs and Host Immunity During Infection. Front Immunol 2019; 10: 3079.

Alenquer M, Amorim M J. Exosome Biogenesis, Regulation, and Function in Viral Infection. Viruses 2015; 7(9): 5066-83.

Kouwaki T, Okamoto M, Tsukamoto H, Fukushima Y, Oshiumi H. Extracellular Vesicles Deliver Host and Virus RNA and Regulate Innate Immune Response. Int J Mol Sci 2017; 18(3).

Nomura S, Taniura T, Ito T. Extracellular Vesicle-Related Thrombosis in Viral Infection. Int J Gen Med 2020; 13: 559-68.

Gambardella J et al. Exosomal microRNAs drive thrombosis in COVID-19. medRxiv; 2020.

Li C, Hu X, Li L, Li J H. Differential microRNA expression in the peripheral blood from human patients with COVID-19. J Clin Lab Anal 2020: e23590.

Nersisyan S, Engibaryan N, Gorbonos A, Kirdey K, Makhonin A, Tonevitsky A. Potential role of cellular miRNAs in coronavirus-host interplay. PeerJ 2020; 8: e9994.

Xu S, Tao Z, Hai B, et al. miR-424(322) reverses chemoresistance via T-cell immune response activation by blocking the PD-L1 immune checkpoint. Nat Commun 2016; 7: 11406.

Richardsen E, Andersen S, Al-Saad S, et al. Low Expression of miR-424-3p is Highly Correlated with Clinical Failure in Prostate Cancer. Sci Rep 2019; 9(1): 10662.

Sherman Horev H, Rabinowitz K M, Elad H, et al. Increase in Processing Factors Is Involved in Skewed MicroRNA Expression in Patients with Ulcerative Colitis Who Develop Small Intestine Inflammation after Pouch Surgery. Inflamm Bowel Dis 2018; 24(5): 1045-54.

Jeon J S, Kim E, Bae Y U, et al. microRNA in Extracellular Vesicles Released by Damaged Podocytes Promote Apoptosis of Renal Tubular Epithelial Cells. Cells 2020; 9(6).

Ghosh G, Subramanian I V, Adhikari N, et al. Hypoxia-induced microRNA-424 expression in human endothelial cells regulates HIF-alpha isoforms and promotes angiogenesis. J Clin Invest 2010; 120(11): 4141-54.

Baptista R, Marques C, Catarino S, et al. MicroRNA-424 (322) as a new marker of disease progression in pulmonary arterial hypertension and its role in right ventricular hypertrophy by targeting SMURF1. Cardiovasc Res 2018; 114(1): 53-64.

Lodge R, Bellini N, Laporte M, et al. Interleukin-1beta Triggers p53-Mediated Downmodulation of CCR5 and HIV-1 Entry in Macrophages through MicroRNAs 103 and 107. mBio 2020; 11(5).

Guo Y, Huang N, Tian M, et al. Integrated Analysis of microRNA-mRNA Expression in Mouse Lungs Infected With H7N9 Influenza Virus: A Direct Comparison of Host-Adapting PB2 Mutants. Front Microbiol 2020; 11: 1762.

Yang M, Zhao L, Sun M. Diagnostic Value of miR-103 in Patients with Sepsis and Noninfectious SIRS and Its Regulatory Role in LPS-Induced Inflammatory Response by Targeting TLR4. Int J Genomics 2020; 2020: 2198308.

Wang Y, Song X, Li Z, et al. MicroRNA-103 Protects Coronary Artery Endothelial Cells against H2O2-Induced Oxidative Stress via BNIP3-Mediated End-Stage Autophagy and Antipyroptosis Pathways. Oxid Med Cell Longev 2020; 2020: 8351342.

Rech M, Kuhn A R, Lumens J, et al. AntagomiR-103 and -107 Treatment Affects Cardiac Function and Metabolism. Mol Ther Nucleic Acids 2019; 14: 424-37.

Qi H, Ren J, E M, et al. MiR-103 inhibiting cardiac hypertrophy through inactivation of myocardial cell autophagy via targeting TRPV3 channel in rat hearts. J Cell Mol Med 2019; 23(3): 1926-39.

Wang Q, Feng Q, Zhang Y, Zhou S, Chen H. Decreased microRNA 103 and microRNA 107 predict increased risks of acute respiratory distress syndrome and 28-day mortality in sepsis patients. Medicine (Baltimore) 2020; 99(25): e20729.

Cordes K R, Sheehy N T, White M P, et al. miR-145 and miR-143 regulate smooth muscle cell fate and plasticity. Nature 2009; 460(7256): 705-10.

Fichtlscherer S, De Rosa S, Fox H, et al. Circulating microRNAs in patients with coronary artery disease. Circ Res 2010; 107(5): 677-84.

Shimizu C, Kim J, Stepanowsky P, et al. Differential expression of miR-145 in children with Kawasaki disease. PLoS One 2013; 8(3): e58159.

Yuan Y, Liu X, Hao S, He Q, Shen Z. Plasma levels of miR-143 and miR-145 are associated with coronary in-stent restenosis within 1 year of follow-up after drug-eluting stent implantation. Ann Transl Med 2020; 8(12): 756.

Wang X, Chen Q Z, Zan Y X, et al. Exosomal miR-145-5p derived from orthohantavirus-infected endothelial cells inhibits HTNV infection. FASEB J 2020.

Zhang X, Gu H, Wang L, Huang F, Cai J. MiR-885-3p is down-regulated in peripheral blood mononuclear cells from TID patients and regulates the inflammatory response via targeting TLR4/NF-kappaB signaling. J Gene Med 2020; 22(1): e3145.

Zhang T, Guo J, Gu J, et al. Identifying the key genes and microRNAs in colorectal cancer liver metastasis by bioinformatics analysis and in vitro experiments. Oncol Rep 2019; 41(1): 279-91.

Goshua G, Pine A B, Meizlish M L, et al. Endotheliopathy in COVID-19-associated coagulopathy: evidence from a single-centre, cross-sectional study. Lancet Haematol 2020; 7(8): e575-e82.

Huang J, Sun Z, Yan W, et al. Identification of microRNA as sepsis biomarker based on miRNAs regulatory network analysis. Biomed Res Int 2014; 2014: 594350.

Wang H, Zhang P, Chen W, Feng D, Jia Y, Xie L. Serum microRNA signatures identified by Solexa sequencing predict sepsis patients' mortality: a prospective observational study. PLoS One 2012; 7(6): e38885.

Wang H, Zhang P, Chen W, Feng D, Jia Y, Xie L X. Evidence for serum miR-15a and miR-16 levels as biomarkers that distinguish sepsis from systemic inflammatory response syndrome in human subjects. Clin Chem Lab Med 2012; 50(8): 1423-8.

Chamorro-Jorganes A, Araldi E, Penalva L O, Sandhu D, Fernandez-Hernando C, Suarez Y. MicroRNA-16 and microRNA-424 regulate cell-autonomous angiogenic functions in endothelial cells via targeting vascular endothelial growth factor receptor-2 and fibroblast growth factor receptor-1. Arterioscler Thromb Vasc Biol 2011; 31(11): 2595-606.

Keller A, Leidinger P, Steinmeyer F, et al. Comprehensive analysis of microRNA profiles in multiple sclerosis including next-generation sequencing. Mult Scler 2014; 20(3): 295-303.

Zhu L, Zhou X, Li S, et al. miR1835p attenuates cerebral ischemia injury by negatively regulating PTEN. Mol Med Rep 2020; 22(5): 3944-54.

Wang Y, Song Y, Pang Y, et al. miR-183-5p alleviates early injury after intracerebral hemorrhage by inhibiting heme oxygenase-1 expression. Aging (Albany NY) 2020; 12(13): 12869-95.

Meng C, Guo Z, Li D, et al. miR-183 and miR-141 in lesion tissues are potential risk factors for poor prognosis in patients with infected abdominal aortic aneurysm. Exp Ther Med 2018; 16(6): 4695-9.

Singaravelu R, Ahmed N, Quan C, et al. A conserved miRNA-183 cluster regulates the innate antiviral response. J Biol Chem 2019; 294(51): 19785-94.

Sun B, Shan Z, Sun G, Wang X. MicroRNA-183-5p acts as a potential diagnostic biomarker for atherosclerosis and regulates the growth of vascular smooth muscle cell. J Chin Med Assoc 2020.

Zhao X, Jia Y, Chen H, Yao H, Guo W. Plasma-derived exosomal miR-183 associates with protein kinase activity and may serve as a novel predictive biomarker of myocardial ischemic injury. Exp Ther Med 2019; 18(1): 179-87.

McGowan K, Simpson K J, Petrik J. Expression Profiles of Exosomal MicroRNAs from HEV- and HCV-Infected Blood Donors and Patients: A Pilot Study. Viruses 2020; 12(8).

Sheraz M, Kanak M, Hasan M, et al. Use of Flaviviral genetic fragments as a potential prevention strategy for HIV-1 Silencing. J Infect Dev Ctries 2016; 10(8): 870-9.

Rosenberger C M, Podyminogin R L, Diercks A H, et al. miR-144 attenuates the host response to influenza virus by targeting the TRAF6-IRF7 signaling axis. PLoS Pathog 2017; 13(4): e1006305.

Guo L, Zhou L, Gao Q, et al. MicroRNA-144-3p inhibits autophagy activation and enhances Bacillus Calmette-Guerin infection by targeting ATG4a in RAW264.7 macrophage cells. PLoS One 2017; 12(6): e0179772.

Li R D, Shen C H, Tao Y F, et al. MicroRNA-144 suppresses the expression of cytokines through targeting RANKL in the matured immune cells. Cytokine 2018; 108: 197-204.

Hu Y W, Hu Y R, Zhao J Y, et al. An agomir of miR-144-3p accelerates plaque formation through impairing reverse cholesterol transport and promoting pro-inflammatory cytokine production. PLoS One 2014; 9(4): e94997.

Khan M A, Sany M R U, Islam M S, Islam A. Epigenetic Regulator miRNA Pattern Differences Among SARS-CoV, SARS-CoV-2, and SARS-CoV-2 World-Wide Isolates Delineated the Mystery Behind the Epic Pathogenicity and Distinct Clinical Characteristics of Pandemic COVID-19. Front Genet 2020; 11: 765.

Zhu Z, Qi Y, Ge A, et al. Comprehensive characterization of serum microRNA profile in response to the emerging avian influenza A (H7N9) virus infection in humans. Viruses 2014; 6(4): 1525-39.

Roderburg C, Benz F, Koch A, et al. A Combined Score of Circulating miRNAs Allows Outcome Prediction in Critically Ill Patients. J Clin Med 2019; 8(10).

Hukowska-Szematowicz B, Maciejak-Jastrzebska A, Blatkiewicz M, et al. Changes in MicroRNA Expression during Rabbit Hemorrhagic Disease Virus (RHDV) Infection. Viruses 2020; 12(9).

Diener C, Hart M, Kehl T, et al. Quantitative and time-resolved miRNA pattern of early human T cell activation. Nucleic Acids Res 2020; 48(18): 10164-83.

Barberis et al. Circulating Exosomes Are Strongly Involved in SARS-CoV-2 Infection. Front. Mol. Biosci. 2021; 8:632290.

Jin Q et al. Extracellular Vesicles: Novel Roles in Neurological Disorders. Stem Cells International. 2021: 6640836

Yao Y et al. D-dimer as a biomarker for disease severity and mortality in COVID-19 patients: a case control study. J. Intensive Care. 2020; 8(49).

Iba T et al. Proposal of the Definition for COVID-19-Associated Coagulopathy. J. Clin. Med. 2021; 10(191).

Ludwig N et al. Isolation and Analysis of Tumor-Derived Exosomes. Curr. Prot. Immunol. (2019) 127, e91.

Gardiner C et al. Extracellular vesicle sizing and enumeration by nanoparticle tracking analysis. J. Extracellular Vesicles (2013) 2:19671.

What is claimed is:

1. A method of treating or inhibiting sequelae associated with SARS-COV-2 in a long COVID patient, the method comprising:
   (a) introducing blood or plasma from the patient into an extracorporeal device comprising a lectin, wherein the patient is a previously SARS-COV-2 infected patient having a reduced or undetectable viral load and exhibiting SARS-COV-2 sequelae that continue for more than 12 weeks post SARS-COV-2 infection;
   (b) contacting the blood or plasma from the patient with the lectin in the extracorporeal device for a time sufficient to allow the portion of SARS-COV-2 present in the blood or plasma to bind to said lectin; and
   (c) reintroducing the blood or plasma obtained after (b) into said patient, wherein the blood or plasma obtained after (b) has a reduced amount of the portion of SARS-COV-2 as compared to the blood or plasma of said patient prior to (b) thereby treating or inhibiting the sequelae associated with SARS-COV-2 in the patient.

2. The method of claim 1, wherein the blood or plasma from the patient comprises a spike protein or S1 of SARS-COV-2.

3. The method of claim 2, further comprising measuring for the presence of the spike protein or S1 in a sample from said patient prior to (a) or after (b) or both.

4. The method of claim 1, wherein the lectin is *Galanthus nivalis* agglutinin (GNA).

5. The method of claim 1, wherein the lectin is immobilized or adsorbed on to a solid support.

6. The method of claim 5, wherein the solid support comprises diatomaceous earth.

7. The method of claim 1, wherein the extracorporeal device comprises a hollow fiber cartridge comprising the lectin and, wherein the blood or plasma flows through hollow fibers of the hollow fiber cartridge.

8. The method of claim 7, wherein the hollow fibers of the hollow fiber cartridge comprise a pore size that excludes cellular components of the blood or plasma from contacting the lectin.

9. The method of claim 8, wherein the pore size is 20-500 nm.

10. The method of claim 1, further comprising repeating steps (a), (b), and (c).

11. The method of claim 1, wherein steps a), (b), and (c) are repeated every day for 1, 2, 3, 4, 5, 6, 7, 8, 9, 10, 11, 12, 13, 14, or 15 days.

* * * * *